US007390787B2

(12) United States Patent
Fraser et al.

(10) Patent No.: US 7,390,787 B2
(45) Date of Patent: *Jun. 24, 2008

(54) COMPOSITIONS AND METHODS FOR TREATING INFECTIONS USING ANALOGUES OF INDOLICIDIN

(75) Inventors: Janet R. Fraser, Vancouver (CA); Michael H. P. West, Caledon East (CA); Timothy J. Krieger, Monrovia, CA (US); Robert Taylor, White Rock (CA); Douglas Erfle, Vancouver (CA)

(73) Assignee: Migenix Inc., Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 10/351,985

(22) Filed: Jan. 24, 2003

(65) Prior Publication Data

US 2004/0009910 A1   Jan. 15, 2004

Related U.S. Application Data

(63) Continuation of application No. 09/667,486, filed on Sep. 22, 2000, now Pat. No. 6,538,106, which is a continuation of application No. 08/915,314, filed on Aug. 20, 1997, now Pat. No. 6,180,604.

(60) Provisional application No. 60/034,949, filed on Jan. 13, 1997, provisional application No. 60/024,754, filed on Aug. 21, 1996.

(51) Int. Cl.
*A61K 38/00* (2006.01)
*A61K 49/00* (2006.01)
*C07K 7/00* (2006.01)

(52) U.S. Cl. .............. 514/14; 530/327; 424/9.1
(58) Field of Classification Search ........... 530/300, 530/324–327; 514/12–14; 424/9.1
See application file for complete search history.

(56) References Cited

U.S. PATENT DOCUMENTS

| 4,510,132 | A | 4/1985 | Vaara ............... 514/11 |
| 5,324,716 | A | 6/1994 | Selsted et al. ....... 514/14 |
| 5,359,030 | A | 10/1994 | Ekwuribe ........... 530/303 |
| 5,438,040 | A | 8/1995 | Ekwuribe ........... 514/3 |
| 5,523,288 | A | 6/1996 | Cohen et al. ........ 514/12 |
| 5,547,939 | A | 8/1996 | Selsted ............ 514/14 |
| 5,578,572 | A | 11/1996 | Horwitz et al. ...... 514/12 |
| 5,593,866 | A | 1/1997 | Hancock et al. ...... 435/69.7 |
| 6,180,604 | B1 | 1/2001 | Fraser et al. ....... 514/12 |
| 6,191,254 | B1 | 2/2001 | Falla et al. ........ 530/300 |

FOREIGN PATENT DOCUMENTS

| EP | 590 070 B1 | 4/1994 |
| WO | WO 91/12815 | 9/1991 |
| WO | WO 92/22308 | 12/1992 |
| WO | WO 95/22338 | 8/1995 |
| WO | WO 96/38473 | 12/1996 |
| WO | WO 97/04796 | 2/1997 |
| WO | WO 97/08199 | * 3/1997 |
| WO | WO 97/31942 | 9/1997 |
| WO | WO 98/07745 | 2/1998 |
| WO | WO 98/45319 | 10/1998 |
| WO | WO 99/43357 | 9/1999 |

OTHER PUBLICATIONS

Hancock, 2000, Cationic antimicrobial peptides: towards clinical applications, Expert Opinion on Investigational Drugs, 9(8): 1723-1729.*
Marr et al., 2006, Antibacterial peptides for therapeutic use: obstacles and realistic outlook, Current Opinion in Pharmacology, 6: 468-472.*
Biosequence Searching for the USPTO (STN International), May 1996, pp. 30-31.
Bunngaard, "Design of Prodrugs," Elsevier Publishing, New York, 1985, pp. 1-24.
Chalk et al., "Full Sequence and Characterization of Two Insect Defensins: Immune Peptides from the Mosquito *Aedes aegypti*," *Proc. R. Soc. London B*. 261(1361):217-221, 1995.
Chalk et al., "Purification of An Insect Defensin from the Mosquito, *Aedes aegypti*," *Insect Biochem. Molec. Biol.* 24(4):403-410, 1994.
Darveau et al., "β-Lactam Antibiotics Potentiate Magainin 2 Antimicrobial Activity In Vitro and In Vivo," *Antimicrobial Agents & Chemotherapy* 35(6):1153-1159, Jun. 1991.
Engström et al., "The Antibacterial Effect of Attacins from the Silk Moth *Hyalophora cecropia* is Directed Against the Outer Membrane of *Escherichia coli*," *EMBO J.* 3(13):3347-3351, 1984.
Falla and Hancock, "Improved Activity of a Synthetic Indolicidin Analog," *Antimicrobial Agents And Chemotherapy* 41(4):771-775, 1997.
Falla et al., "Mode of action of the antimicrobial peptide indolicidin," *Journal of Biological Chemistry* 271(32): 19298-19303, 1996.
Hancock, "The Role of Fundamental Research and Biotechnology in Finding Solutions to the Global Problem of Antibiotic Resistance," *Clin. Infectious Diseases* 24(Supp 1)S148-S150, 1997.
Ladokhin et al., "CD Spectra of Indolicidin Antimicrobial Peptides Suggest Turns, Not Polyproline Helix," *Biochemistry* 38:12313-12319, 1999.
Lawyer et al., "Antimicrobial Activity of a 13 Amino Acid Tryptophan-Rich Peptide Derived From a Putative Porcine Precursor Protein of a Novel Family of Antibacterial Peptides," *FEBS Letters* 390:95-98, 1996.

(Continued)

*Primary Examiner*—Jon D. Epperson
*Assistant Examiner*—Amber D. Steele
(74) *Attorney, Agent, or Firm*—Darby & Darby P.C.; Bruce E. Black

(57) ABSTRACT

Compositions and methods for treating infections, especially bacterial infections, are provided. Indolicidin peptide analogues containing at least two basic amino acids are prepared. The analogues are administered as modified peptides, preferably containing photo-oxidized solubilizer.

45 Claims, 18 Drawing Sheets

OTHER PUBLICATIONS

Piers et al., "Improvement of Outer Membrane-Permeabilizing and Lipopolysaccharide-Binding Activities of an Antimicrobial Cationic Peptide by C-Terminal Modification," *Antimicrobial Agents & Chemotherapy* 38(10):2311-2316, Oct. 1994.

Robinson, Jr. et al., "Anti-HIV-1 Activity of Indolicidin, an Antimicrobial Peptide from Neutrophils," *Journal of Leukocyte Biology* 63:94-100, 1998.

Selsted et al., "Indolicidin, a Novel Bactericidal Tridecapeptide Amide from Neutrophils," *The Journal of Biological Chemistry* 267(7):4292-4295, 1992.

Selsted et al., "Purification, Characterization, Synthesis and cDNA Cloning of Indolicidin: A Tryptophan-Rich Microbicidal Tridecapeptide from Neutrophils," *Proceedings of the 12th American Peptide Symposium*, Jun. 16-21, 1991, Cambridge, MA, 1991, pp. 905-907.

Subbalakshmi and Sitaram, "Mechanism of Antimicrobial Action of Indolicidin," *FEMS Microbiology Letters* 160:91-96, 1998.

Subbalakshmi et al., "Interaction of Indolicidin, a 13-Residue Peptide Rich in Tryptophan and Proline and its Analogues with Model Membranes," *J. Biosci.* 23(1):9-13, 1998.

Subbalakshmi et al., "Requirements for antibacterial and hemolytic activities in the bovine neutrophil derived 13-residue peptide indolicidin," *FEBS Letters* 395: 48-52, 1996.

Tanchak et al., "Tryptophanins: Isolation and Molecular Characterization of Oat cDNA Clones Encoding Proteins Structurally Related to Puroindoline and Wheat Grain Softness Proteins," *Plant Science* 137:173-184, 1998.

Uchida et al., "Antibacterial activity of the mammalian host defense peptide, indolicidin and its fragments," *Peptide Chemistry*, pp. 229-232, 1995.

Uchida et al., "Structure-Activity of Antibacterial Peptide Indolicidin and Analogs," *Peptide Science*, pp. 221-224, 1999.

Vaara and Porro, "Group of Peptides That Act Synergistically with Hydrophobic Antibiotics Against Gram-Negative Enteric Bacteria," *Antimicrobial Agents & Chemotherapy* 40(8):1801-1805, Aug. 1996.

Vaara and Vaara, "Ability of Cecropin B to Penetrate the Enterobacterial Outer Membrane," *Antimicrobial Agents & Chemotherapy* 38(10):2498-2501, Oct. 1994.

Vaara and Vaara, "Polycations Sensitize Enteric Bacteria to Antibiotics," *Antimicrobial Agents & Chemotherapy* 24(1):107-113, Jul. 1983.

Vaara and Vaara, "Sensitization of Gram-Negative Bacteria to Antibiotics and Complement by a Nontoxic Oligopeptide," *Nature* 303:526-528, Jun. 9, 1983.

Vaara, "Agents That Increase the Permeability of the Outer Membrane," *Microbiological Reviews* 56(3):395-411, Sep. 1992.

Vaara, "The Outer Membrane as the Penetration Barrier Against Mupirocin in Gram-Negative Enteric Bacteria," *J. Antimicrob. Chemother.* 29(2):221-222, Feb. 1992.

Van Abel et al., "Synthesis and Characterization of Indolicidin, a Tryptophan-Rich Antimicrobial Peptide from Bovine Neutrophils" *Int. J. Peptide Protein Res.* 45:401-409, 1995.

Wakabayashi et al., "N-Acylated and D Enantiomer Derivatives of a Nonamer Core Peptide of Lactoferricin B Showing Improved Antimicrobial Activity," *Antimicrobial Agents And Chemotherapy* 43(5):1267-1269, 1999.

\* cited by examiner

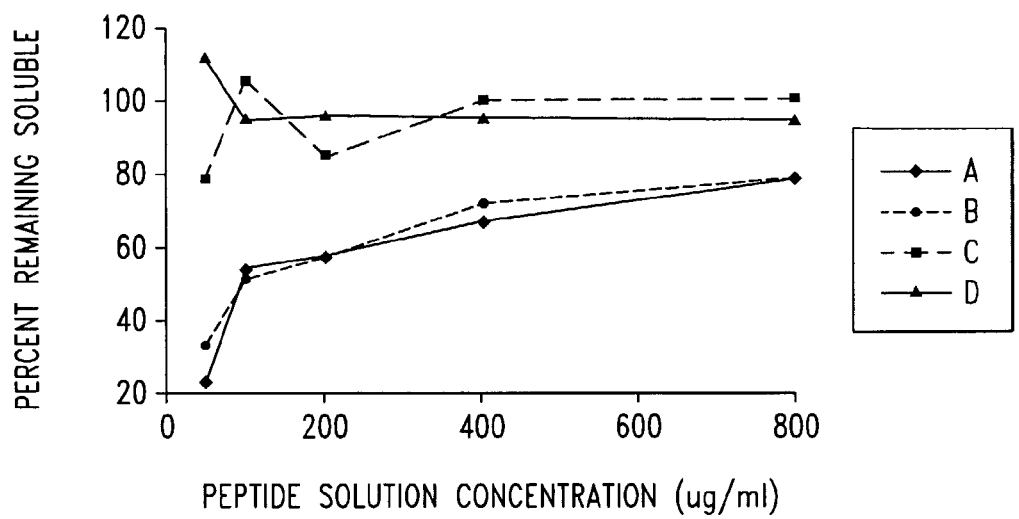
*Fig. 4*
MBI 10B in Formulations C1 and D
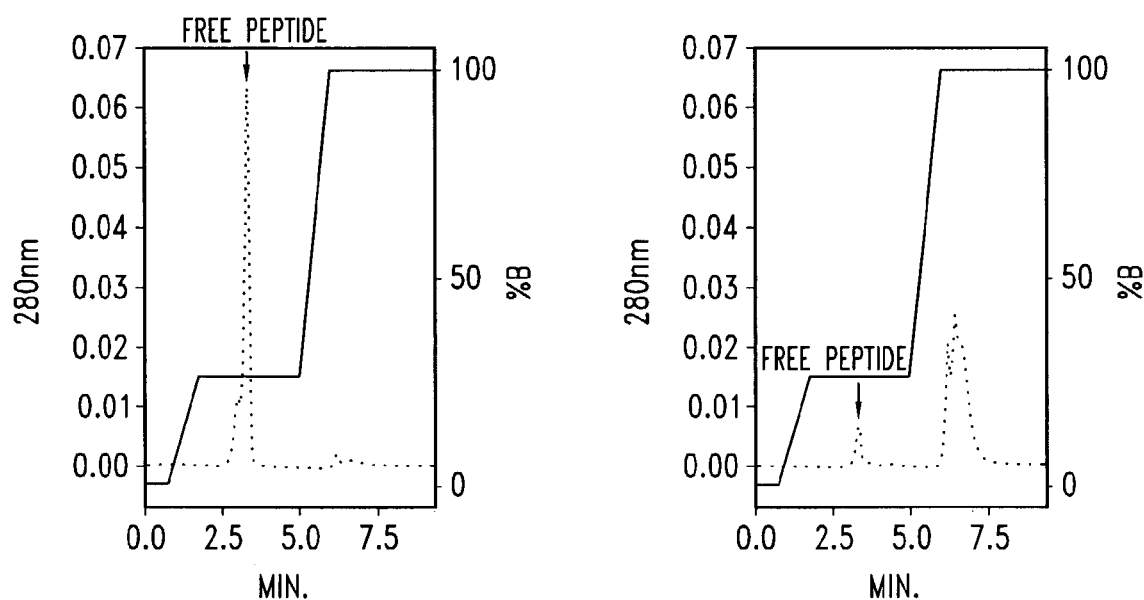
*Fig. 5A*  *Fig. 5B*

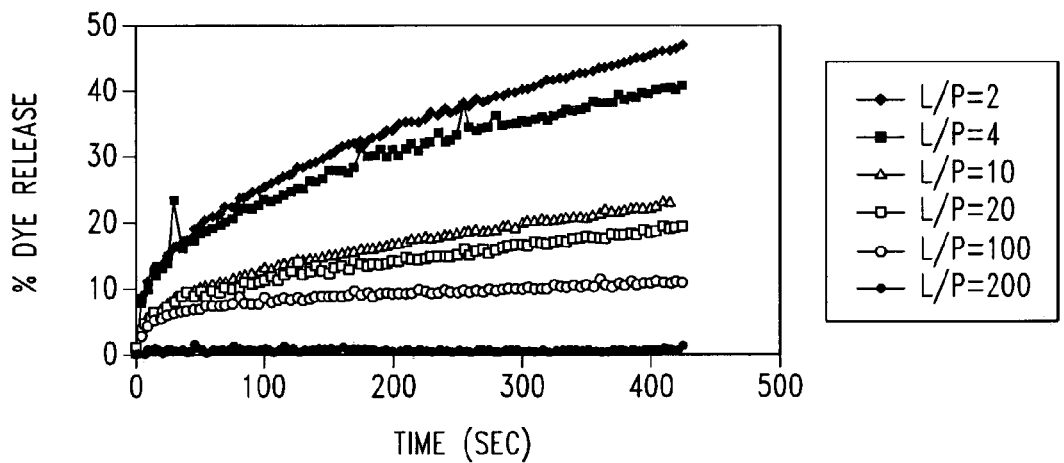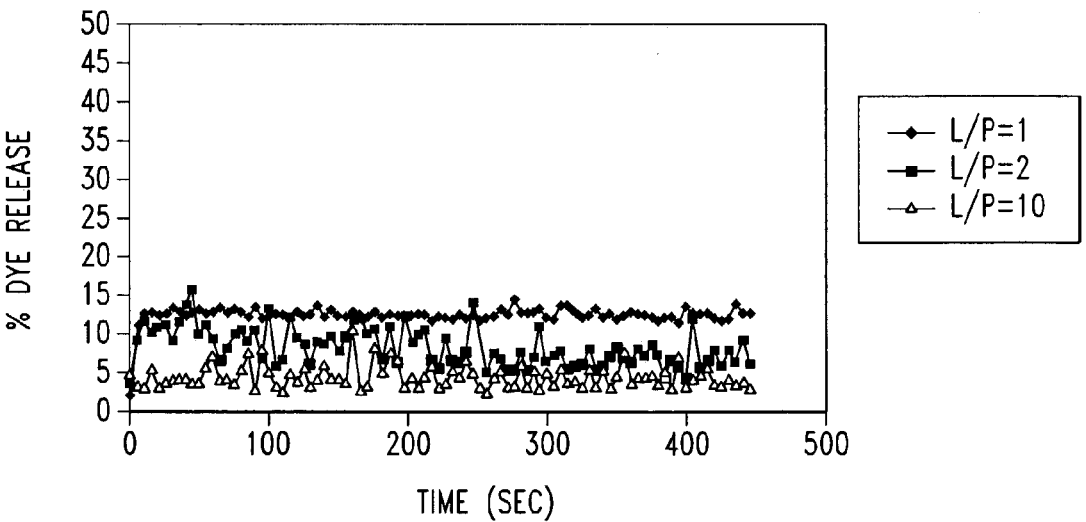
Fig. 7

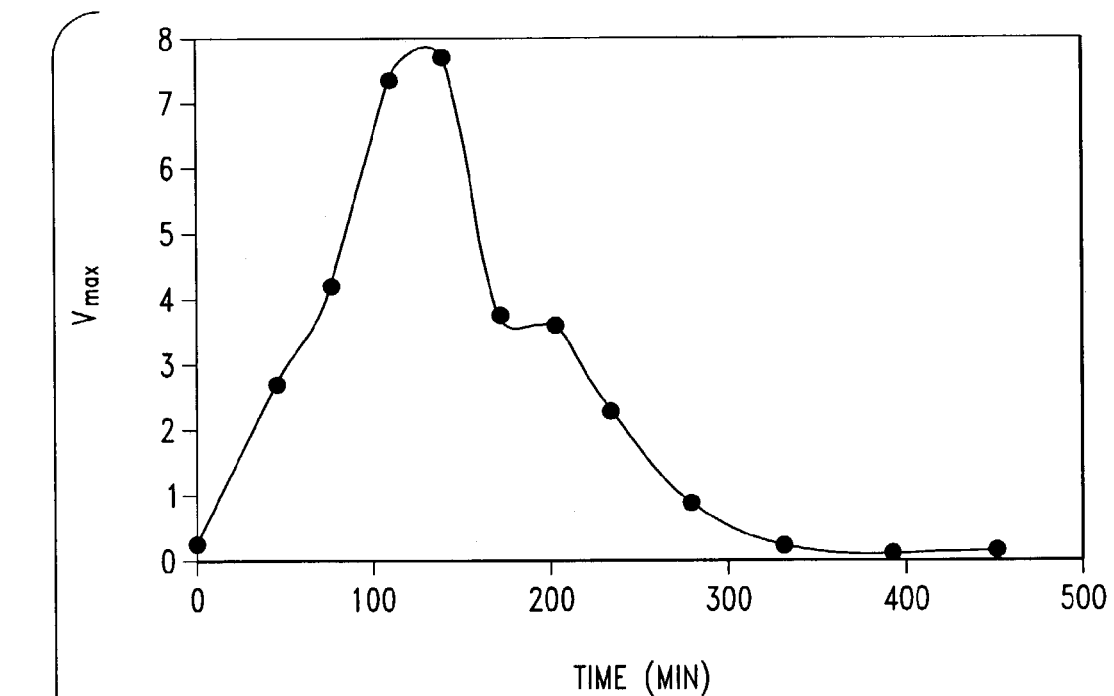
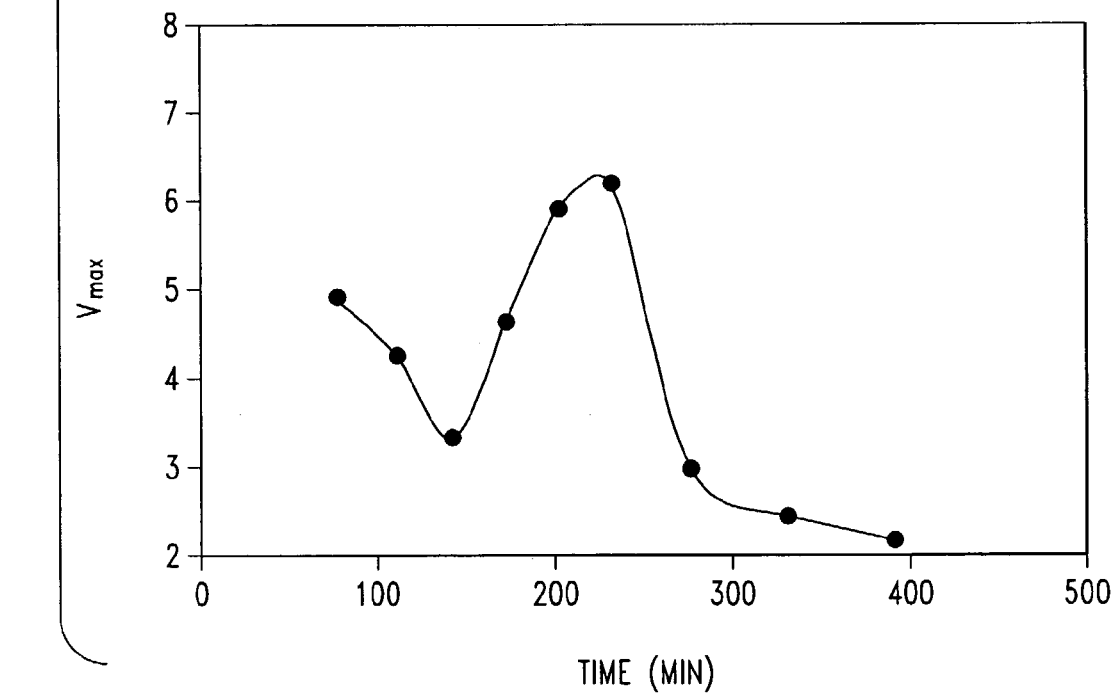
Fig. 8

SEQUENCE LISTING (1) GENERAL INFORMATION:

(iii) NUMBER OF SEQUENCES: 90

(2) INFORMATION FOR SEQ ID NO: 1:

(i) SEQUENCE CHARACTERISTICS:
        (A) LENGTH: 8 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 2
        (D) OTHER INFORMATION: /note= "Wherein X is a Hydrophobic
            Residue"

(ix) FEATURE:
        (A) NAME/KEY: Modified-site
        (B) LOCATION: 3
        (D) OTHER INFORMATION: /note= "Wherein X is Proline or
            Valine"

(ix) FEATURE:
        (A) NAME/KEY: Modified-site
        (B) LOCATION: 4
        (D) OTHER INFORMATION: /note= "Wherein X is a Hydrophobic
            Residue"

(ix) FEATURE:
        (A) NAME/KEY: Modified-site
        (B) LOCATION: 5
        (D) OTHER INFORMATION: /note= "Wherein X is a Hydrophobic
            Residue"

(ix) FEATURE:
        (A) NAME/KEY: Modified-site
        (B) LOCATION: 6
        (D) OTHER INFORMATION: /note= "Wherein X is Proline or
            Valine"

(ix) FEATURE:
        (A) NAME/KEY: Modified-site
        (B) LOCATION: 7
        (D) OTHER INFORMATION: /note= "Wherein X is a Hydrophobic
            Residue"

(ix) FEATURE:
        (A) NAME/KEY: Modified-site
        (B) LOCATION: 8
        (D) OTHER INFORMATION: /note= "Wherein X is a Basic Amino
            Acid"

(xi) SEQUENCE DESCRIPTION: SEQ ID NO: 1:

Arg Xaa Xaa Xaa Xaa Xaa Xaa Xaa
1               5

(2) INFORMATION FOR SEQ ID NO: 2:

(i) SEQUENCE CHARACTERISTICS:
        (A) LENGTH: 8 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 1
        (D) OTHER INFORMATION: /note= "Wherein X is a Basic Amino
            Acid"

(ix) FEATURE:

```
        (A) NAME/KEY: Modified-site
        (B) LOCATION: 2
        (D) OTHER INFORMATION: /note= "Wherein X is a Hydrophobic
            Residue"

(ix) FEATURE:
        (A) NAME/KEY: Modified-site
        (B) LOCATION: 3
        (D) OTHER INFORMATION: /note= "Wherein X is Proline or
            Valine"

(ix) FEATURE:
        (A) NAME/KEY: Modified-site
        (B) LOCATION: 4
        (D) OTHER INFORMATION: /note= "Wherein X is a Hydrophobic
            Residue"

(ix) FEATURE:
        (A) NAME/KEY: Modified-site
        (B) LOCATION: 5
        (D) OTHER INFORMATION: /note= "Wherein X is a Hydrophobic
            Residue"

(ix) FEATURE:
        (A) NAME/KEY: Modified-site
        (B) LOCATION: 6
        (D) OTHER INFORMATION: /note= "Wherein X is Proline or
            Valine"

(ix) FEATURE:
        (A) NAME/KEY: Modified-site
        (B) LOCATION: 7
        (D) OTHER INFORMATION: /note= "Wherein X is a Hydrophobic
            Residue"

(ix) FEATURE:
        (A) NAME/KEY: Modified-site
        (B) LOCATION: 8
        (D) OTHER INFORMATION: /note= "Wherein X is a Basic Amino
            Acid"

(ix) FEATURE:
        (B) LOCATION: 2 and 6
        (D) OTHER INFORMATION: /note= "At least One of the
            Residues at Positions 2 or 6 is Valine"

(xi) SEQUENCE DESCRIPTION: SEQ ID NO: 2:

Xaa Xaa Xaa Xaa Xaa Xaa Xaa Xaa
1               5

(2) INFORMATION FOR SEQ ID NO: 3:

(i) SEQUENCE CHARACTERISTICS:
        (A) LENGTH: 10 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 1
        (D) OTHER INFORMATION: /note= "Wherein X is a Basic Amino
            Acid"

(ix) FEATURE:
        (A) NAME/KEY: Modified-site
        (B) LOCATION: 2
        (D) OTHER INFORMATION: /note= "Wherein X is a Basic Amino
            Acid"

(ix) FEATURE:
        (A) NAME/KEY: Modified-site
        (B) LOCATION: 3
        (D) OTHER INFORMATION: /note= "Wherein X is a Basic Amino
            Acid"

(ix) FEATURE:
```

```
        (A) NAME/KEY: Modified-site
        (B) LOCATION: 4
        (D) OTHER INFORMATION: /note= "Wherein X is a Hydrophobic
            Residue"

(ix) FEATURE:
        (A) NAME/KEY: Modified-site
        (B) LOCATION: 5
        (D) OTHER INFORMATION: /note= "Wherein X is Proline or
            Valine"

(ix) FEATURE:
        (A) NAME/KEY: Modified-site
        (B) LOCATION: 6
        (D) OTHER INFORMATION: /note= "Wherein X is a Hydrophobic
            Residue"

(ix) FEATURE:
        (A) NAME/KEY: Modified-site
        (B) LOCATION: 7
        (D) OTHER INFORMATION: /note= "Wherein X is a Hydrophobic
            Residue"

(ix) FEATURE:
        (A) NAME/KEY: Modified-site
        (B) LOCATION: 8
        (D) OTHER INFORMATION: /note= "Wherein X is Proline or
            Valine"

(ix) FEATURE:
        (A) NAME/KEY: Modified-site
        (B) LOCATION: 9
        (D) OTHER INFORMATION: /note= "Wherein X is a Hydrophobic
            Residue"

(ix) FEATURE:
        (A) NAME/KEY: Modified-site
        (B) LOCATION: 10
        (D) OTHER INFORMATION: /note= "Wherein X is a Basic Amino
            Acid"

(xi) SEQUENCE DESCRIPTION: SEQ ID NO: 3:

Xaa Xaa Xaa Xaa Xaa Xaa Xaa Xaa Xaa Xaa
1               5                   10

(2) INFORMATION FOR SEQ ID NO: 4:

(i) SEQUENCE CHARACTERISTICS:
        (A) LENGTH: 17 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 1
        (D) OTHER INFORMATION: /note= "Wherein X is a Basic Amino
            Acid"

(ix) FEATURE:
        (A) NAME/KEY: Modified-site
        (B) LOCATION: 2
        (D) OTHER INFORMATION: /note= "Wherein X is a Hydrophobic
            Amino Acid"

(ix) FEATURE:
        (A) NAME/KEY: Modified-site
        (B) LOCATION: 3
        (D) OTHER INFORMATION: /note= "Wherein X is Proline or
            Valine"

(ix) FEATURE:
        (A) NAME/KEY: Modified-site
        (B) LOCATION: 4
        (D) OTHER INFORMATION: /note= "Wherein X is a Hydrophobic
            Residue"
```

```
    (ix) FEATURE:
         (A) NAME/KEY: Modified-site
         (B) LOCATION: 5
         (D) OTHER INFORMATION: /note= "Wherein X is a Hydrophobic
             Residue"

(ix) FEATURE:
         (A) NAME/KEY: Modified-site
         (B) LOCATION: 6
         (D) OTHER INFORMATION: /note= "Wherein X is Proline or
             Valine"

(ix) FEATURE:
         (A) NAME/KEY: Modified-site
         (B) LOCATION: 7
         (D) OTHER INFORMATION: /note= "Wherein X is a Hydrophobic
             Residue"

(ix) FEATURE:
         (A) NAME/KEY: Modified-site
         (B) LOCATION: 8
         (D) OTHER INFORMATION: /note= "Wherein X is a Basic Amino
             Acid"

(ix) FEATURE:
         (A) NAME/KEY: Modified-site
         (B) LOCATION: 9
         (D) OTHER INFORMATION: /note= "Wherein X is a Basic Amino
             Acid"

(ix) FEATURE:
         (A) NAME/KEY: Modified-site
         (B) LOCATION: 13
         (D) OTHER INFORMATION: /note= "Wherein X is a Basic Amino
             Acid"

(ix) FEATURE:
         (A) NAME/KEY: Modified-site
         (B) LOCATION: 14
         (D) OTHER INFORMATION: /note= "Wherein X is a Basic Amino
             Acid"

(xi) SEQUENCE DESCRIPTION: SEQ ID NO: 4:

Xaa Xaa Xaa Xaa Xaa Xaa Xaa Xaa Xaa Met Ile Leu Xaa Xaa Ala Gl
1               5                   10                  15

Ser (2) INFORMATION FOR SEQ ID NO: 5:

(i) SEQUENCE CHARACTERISTICS:
         (A) LENGTH: 18 amino acids
         (B) TYPE: amino acid
         (C) STRANDEDNESS: single
         (D) TOPOLOGY: linear (ix) FEATURE:
         (A) NAME/KEY: Modified-site
         (B) LOCATION: 1
         (D) OTHER INFORMATION: /note= "Wherein X is a Basic Amino
             Acid"

(ix) FEATURE:
         (A) NAME/KEY: Modified-site
         (B) LOCATION: 2
         (D) OTHER INFORMATION: /note= "Wherein X is a Hydrophobic
             Amino Acid"

(ix) FEATURE:
         (A) NAME/KEY: Modified-site
         (B) LOCATION: 3
         (D) OTHER INFORMATION: /note= "Wherein X is Proline or
             Valine"

(ix) FEATURE:
         (A) NAME/KEY: Modified-site
         (B) LOCATION: 4
```

```
        (D) OTHER INFORMATION: /note= "Wherein X is a Hydrophobic
            Residue"

(ix) FEATURE:
        (A) NAME/KEY: Modified-site
        (B) LOCATION: 5
        (D) OTHER INFORMATION: /note= "Wherein X is a Hydrophobic
            Residue"

(ix) FEATURE:
        (A) NAME/KEY: Modified-site
        (B) LOCATION: 6
        (D) OTHER INFORMATION: /note= "Wherein X is Proline or
            Valine"

(ix) FEATURE:
        (A) NAME/KEY: Modified-site
        (B) LOCATION: 7
        (D) OTHER INFORMATION: /note= "Wherein X is a Hydrophobic
            Residue"

(ix) FEATURE:
        (A) NAME/KEY: Modified-site
        (B) LOCATION: 8
        (D) OTHER INFORMATION: /note= "Wherein X is a Basic Amino
            Acid"

(ix) FEATURE:
        (A) NAME/KEY: Modified-site
        (B) LOCATION: 9
        (D) OTHER INFORMATION: /note= "Wherein X is a Basic Amino
            Acid"

(ix) FEATURE:
        (A) NAME/KEY: Modified-site
        (B) LOCATION: 10
        (D) OTHER INFORMATION: /note= "Wherein X is a Basic Amino
            Acid"

(ix) FEATURE:
        (A) NAME/KEY: Modified-site
        (B) LOCATION: 14
        (D) OTHER INFORMATION: /note= "Wherein X is a Basic Amino
            Acid"

(ix) FEATURE:
        (A) NAME/KEY: Modified-site
        (B) LOCATION: 15
        (D) OTHER INFORMATION: /note= "Wherein X is a Basic Amino
            Acid"

(xi) SEQUENCE DESCRIPTION: SEQ ID NO: 5:

Xaa Xaa Xaa Xaa Xaa Xaa Xaa Xaa Xaa Xaa Met Ile Leu Xaa Xaa Al
1               5                   10                  15

Gly Ser (2) INFORMATION FOR SEQ ID NO: 6:

(i) SEQUENCE CHARACTERISTICS:
        (A) LENGTH: 18 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 1
        (D) OTHER INFORMATION: /note= "Wherein X is a Basic Amino
            Acid"

(ix) FEATURE:
        (A) NAME/KEY: Modified-site
        (B) LOCATION: 2
        (D) OTHER INFORMATION: /note= "Wherein X is a Hydrophobic
            Amino Acid"
```

```
    (ix) FEATURE:
         (A) NAME/KEY: Modified-site
         (B) LOCATION: 3
         (D) OTHER INFORMATION: /note= "Wherein X is Proline or
             Valine"

(ix) FEATURE:
         (A) NAME/KEY: Modified-site
         (B) LOCATION: 4
         (D) OTHER INFORMATION: /note= "Wherein X is a Hydrophobic
             Residue"

(ix) FEATURE:
         (A) NAME/KEY: Modified-site
         (B) LOCATION: 5
         (D) OTHER INFORMATION: /note= "Wherein X is a Hydrophobic
             Residue"

(ix) FEATURE:
         (A) NAME/KEY: Modified-site
         (B) LOCATION: 6
         (D) OTHER INFORMATION: /note= "Wherein X is Proline or
             Valine"

(ix) FEATURE:
         (A) NAME/KEY: Modified-site
         (B) LOCATION: 7
         (D) OTHER INFORMATION: /note= "Wherein X is a Hydrophobic
             Residue"

(ix) FEATURE:
         (A) NAME/KEY: Modified-site
         (B) LOCATION: 8
         (D) OTHER INFORMATION: /note= "Wherein X is a Basic Amino
             Acid"

(ix) FEATURE:
         (A) NAME/KEY: Modified-site
         (B) LOCATION: 9
         (D) OTHER INFORMATION: /note= "Wherein X is a Basic Amino
             Acid"

(ix) FEATURE:
         (A) NAME/KEY: Modified-site
         (B) LOCATION: 14
         (D) OTHER INFORMATION: /note= "Wherein X is a Basic Amino
             Acid"

(ix) FEATURE:
         (A) NAME/KEY: Modified-site
         (B) LOCATION: 15
         (D) OTHER INFORMATION: /note= "Wherein X is a Basic Amino
             Acid"

(xi) SEQUENCE DESCRIPTION: SEQ ID NO: 6:

Xaa Xaa Xaa Xaa Xaa Xaa Xaa Xaa Xaa Xaa Met Ile Leu Xaa Xaa Al
1               5                   10                  15

Gly Ser (2) INFORMATION FOR SEQ ID NO: 7:

(i) SEQUENCE CHARACTERISTICS:
         (A) LENGTH: 19 amino acids
         (B) TYPE: amino acid
         (C) STRANDEDNESS: single
         (D) TOPOLOGY: linear (ix) FEATURE:
         (A) NAME/KEY: Modified-site
         (B) LOCATION: 1
         (D) OTHER INFORMATION: /note= "Wherein X is a Basic Amino
             Acid"

(ix) FEATURE:
         (A) NAME/KEY: Modified-site
         (B) LOCATION: 2
```

(D) OTHER INFORMATION: /note= "Wherein X is a Hydrophobic Amino Acid"

(ix) FEATURE:
    (A) NAME/KEY: Modified-site
    (B) LOCATION: 3
    (D) OTHER INFORMATION: /note= "Wherein X is Proline or Valine"

(ix) FEATURE:
    (A) NAME/KEY: Modified-site
    (B) LOCATION: 4
    (D) OTHER INFORMATION: /note= "Wherein X is a Hydrophobic Residue"

(ix) FEATURE:
    (A) NAME/KEY: Modified-site
    (B) LOCATION: 5
    (D) OTHER INFORMATION: /note= "Wherein X is a Hydrophobic Residue"

(ix) FEATURE:
    (A) NAME/KEY: Modified-site
    (B) LOCATION: 6
    (D) OTHER INFORMATION: /note= "Wherein X is Proline or Valine"

(ix) FEATURE:
    (A) NAME/KEY: Modified-site
    (B) LOCATION: 7
    (D) OTHER INFORMATION: /note= "Wherein X is a Hydrophobic Residue"

(ix) FEATURE:
    (A) NAME/KEY: Modified-site
    (B) LOCATION: 8
    (D) OTHER INFORMATION: /note= "Wherein X is a Basic Amino Acid"

(ix) FEATURE:
    (A) NAME/KEY: Modified-site
    (B) LOCATION: 9
    (D) OTHER INFORMATION: /note= "Wherein X is a Basic Amino Acid"

(ix) FEATURE:
    (A) NAME/KEY: Modified-site
    (B) LOCATION: 10
    (D) OTHER INFORMATION: /note= "Wherein X is a Basic Amino Acid"

(ix) FEATURE:
    (A) NAME/KEY: Modified-site
    (B) LOCATION: 15
    (D) OTHER INFORMATION: /note= "Wherein X is a Basic Amino Acid"

(ix) FEATURE:
    (A) NAME/KEY: Modified-site
    (B) LOCATION: 16
    (D) OTHER INFORMATION: /note= "Wherein Xaa is a Basic Amino Acid"

(xi) SEQUENCE DESCRIPTION: SEQ ID NO: 7:

```
Xaa Xaa Xaa Xaa Xaa Xaa Xaa Xaa Xaa Xaa Xaa Met Ile Leu Xaa Xa
 1               5                  10                  15
Ala Gly Ser
```

(2) INFORMATION FOR SEQ ID NO: 8:

(i) SEQUENCE CHARACTERISTICS:
        (A) LENGTH: 10 amino acids
        (B) TYPE: amino acid
        (C) STRANDEDNESS: single
        (D) TOPOLOGY: linear

```
    (ix) FEATURE:
         (A) NAME/KEY: Modified-site
         (B) LOCATION: 1
         (D) OTHER INFORMATION: /note= "Wherein X is a Basic Amino
             Acid"

(ix) FEATURE:
         (A) NAME/KEY: Modified-site
         (B) LOCATION: 2
         (D) OTHER INFORMATION: /note= "Wherein X is a Hydrophobic
             Amino Acid"

(ix) FEATURE:
         (A) NAME/KEY: Modified-site
         (B) LOCATION: 3
         (D) OTHER INFORMATION: /note= "Wherein X is Proline or
             Valine"

(ix) FEATURE:
         (A) NAME/KEY: Modified-site
         (B) LOCATION: 4
         (D) OTHER INFORMATION: /note= "Wherein X is a Hydrophobic
             Residue"

(ix) FEATURE:
         (A) NAME/KEY: Modified-site
         (B) LOCATION: 5
         (D) OTHER INFORMATION: /note= "Wherein X is a Hydrophobic
             Residue"

(ix) FEATURE:
         (A) NAME/KEY: Modified-site
         (B) LOCATION: 6
         (D) OTHER INFORMATION: /note= "Wherein X is Proline or
             Valine"

(ix) FEATURE:
         (A) NAME/KEY: Modified-site
         (B) LOCATION: 7
         (D) OTHER INFORMATION: /note= "Wherein X is a Hydrophobic
             Residue"

(ix) FEATURE:
         (A) NAME/KEY: Modified-site
         (B) LOCATION: 8
         (D) OTHER INFORMATION: /note= "Wherein X is a Basic Amino
             Acid"

(ix) FEATURE:
         (A) NAME/KEY: Modified-site
         (B) LOCATION: 9
         (D) OTHER INFORMATION: /note= "Wherein X is a Basic Amino
             Acid"

(xi) SEQUENCE DESCRIPTION: SEQ ID NO: 8:

Xaa Xaa Xaa Xaa Xaa Xaa Xaa Xaa Xaa Met
1               5                   10

(2) INFORMATION FOR SEQ ID NO: 9:

(i) SEQUENCE CHARACTERISTICS:
        (A) LENGTH: 11 amino acids
        (B) TYPE: amino acid
        (C) STRANDEDNESS: single
        (D) TOPOLOGY: linear (ix) FEATURE:
         (A) NAME/KEY: Modified-site
         (B) LOCATION: 1
         (D) OTHER INFORMATION: /note= "Wherein X is a Basic Amino
             Acid"

(ix) FEATURE:
         (A) NAME/KEY: Modified-site
         (B) LOCATION: 2
         (D) OTHER INFORMATION: /note= "Wherein X is a Hydrophobic
             Amino Acid"
```

(ix) FEATURE:
        (A) NAME/KEY: Modified-site
        (B) LOCATION: 3
        (D) OTHER INFORMATION: /note= "Wherein X is Proline or
            Valine"

(ix) FEATURE:
        (A) NAME/KEY: Modified-site
        (B) LOCATION: 4
        (D) OTHER INFORMATION: /note= "Wherein X is a Hydrophobic
            Residue"

(ix) FEATURE:
        (A) NAME/KEY: Modified-site
        (B) LOCATION: 5
        (D) OTHER INFORMATION: /note= "Wherein X is a Hydrophobic
            Residue"

(ix) FEATURE:
        (A) NAME/KEY: Modified-site
        (B) LOCATION: 6
        (D) OTHER INFORMATION: /note= "Wherein X is Proline or
            Valine"

(ix) FEATURE:
        (A) NAME/KEY: Modified-site
        (B) LOCATION: 7
        (D) OTHER INFORMATION: /note= "Wherein X is a Hydrophobic
            Residue"

(ix) FEATURE:
        (A) NAME/KEY: Modified-site
        (B) LOCATION: 8
        (D) OTHER INFORMATION: /note= "Wherein X is a Basic Amino
            Acid"

(ix) FEATURE:
        (A) NAME/KEY: Modified-site
        (B) LOCATION: 9
        (D) OTHER INFORMATION: /note= "Wherein X is a Basic Amino
            Acid"

(xi) SEQUENCE DESCRIPTION: SEQ ID NO: 9:

Xaa Xaa Xaa Xaa Xaa Xaa Xaa Xaa Xaa Xaa Met
1               5                   10

(2) INFORMATION FOR SEQ ID NO: 10:

(i) SEQUENCE CHARACTERISTICS:
        (A) LENGTH: 8 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 2
        (D) OTHER INFORMATION: /note= "Wherein Xaa is a Basic
            Amino Acid"

(ix) FEATURE:
        (A) NAME/KEY: Modified-site
        (B) LOCATION: 3
        (D) OTHER INFORMATION: /note= "Wherein Xaa is a
            Hydrophobic Residue"

(ix) FEATURE:
        (A) NAME/KEY: Modified-site
        (B) LOCATION: 4
        (D) OTHER INFORMATION: /note= "Wherein Xaa is a
            Hydrophobic Residue"

(ix) FEATURE:
        (A) NAME/KEY: Modified-site
        (B) LOCATION: 5
        (D) OTHER INFORMATION: /note= "Wherein Xaa is a -continued

```
                Hydrophobic Residue"

(ix) FEATURE:
         (A) NAME/KEY: Modified-site
         (B) LOCATION: 6
         (D) OTHER INFORMATION: /note= "Wherein Xaa is a
             Hydrophobic Residue"

(xi) SEQUENCE DESCRIPTION: SEQ ID NO: 10:

Leu Xaa Xaa Xaa Xaa Xaa Arg Lys
1               5

(2) INFORMATION FOR SEQ ID NO: 11:

(i) SEQUENCE CHARACTERISTICS:
         (A) LENGTH: 9 amino acids
         (B) TYPE: amino acid
         (C) STRANDEDNESS: single
         (D) TOPOLOGY: linear (ix) FEATURE:
         (A) NAME/KEY: Modified-site
         (B) LOCATION: 2
         (D) OTHER INFORMATION: /note= "Wherein Xaa is a Basic
             Amino Acid"

(ix) FEATURE:
         (A) NAME/KEY: Modified-site
         (B) LOCATION: 3
         (D) OTHER INFORMATION: /note= "Wherein Xaa is a Basic
             Amino Acid"

(ix) FEATURE:
         (A) NAME/KEY: Modified-site
         (B) LOCATION: 4
         (D) OTHER INFORMATION: /note= "Wherein Xaa is a
             Hydrophobic Residue"

(ix) FEATURE:
         (A) NAME/KEY: Modified-site
         (B) LOCATION: 5
         (D) OTHER INFORMATION: /note= "Wherein Xaa is a
             Hydrophobic Residue"

(ix) FEATURE:
         (A) NAME/KEY: Modified-site
         (B) LOCATION: 6
         (D) OTHER INFORMATION: /note= "Wherein Xaa is a
             Hydrophobic Residue"

(ix) FEATURE:
         (A) NAME/KEY: Modified-site
         (B) LOCATION: 7
         (D) OTHER INFORMATION: /note= "Wherein Xaa is a
             Hydrophobic Residue"

(xi) SEQUENCE DESCRIPTION: SEQ ID NO: 11:

Leu Xaa Xaa Xaa Xaa Xaa Xaa Arg Lys
1               5

(2) INFORMATION FOR SEQ ID NO: 12:

(i) SEQUENCE CHARACTERISTICS:
         (A) LENGTH: 9 amino acids
         (B) TYPE: amino acid
         (C) STRANDEDNESS: single
         (D) TOPOLOGY: linear (ix) FEATURE:
         (A) NAME/KEY: Modified-site
         (B) LOCATION: 2
         (D) OTHER INFORMATION: /note= "Wherein Xaa is a Basic
             Amino Acid"

(ix) FEATURE:
```

(A) NAME/KEY: Modified-site
                (B) LOCATION: 3
                (D) OTHER INFORMATION: /note= "Wherein Xaa is a
                    Hydrophobic Residue"

(ix) FEATURE:
                (A) NAME/KEY: Modified-site
                (B) LOCATION: 4
                (D) OTHER INFORMATION: /note= "Wherein Xaa is Proline or
                    Valine"

(ix) FEATURE:
                (A) NAME/KEY: Modified-site
                (B) LOCATION: 5
                (D) OTHER INFORMATION: /note= "Wherein Xaa is a
                    Hydrophobic Residue"

(ix) FEATURE:
                (A) NAME/KEY: Modified-site
                (B) LOCATION: 6
                (D) OTHER INFORMATION: /note= "Wherein Xaa is a
                    Hydrophobic Residue"

(ix) FEATURE:
                (A) NAME/KEY: Modified-site
                (B) LOCATION: 7
                (D) OTHER INFORMATION: /note= "Wherein Xaa is a
                    Hydrophobic Residue"

(xi) SEQUENCE DESCRIPTION: SEQ ID NO: 12:

Leu Xaa Xaa Xaa Xaa Xaa Xaa Arg Lys
1               5

(2) INFORMATION FOR SEQ ID NO: 13:

(i) SEQUENCE CHARACTERISTICS:
                (A) LENGTH: 9 amino acids
                (B) TYPE: amino acid
                (C) STRANDEDNESS: single
                (D) TOPOLOGY: linear (ix) FEATURE:
                (A) NAME/KEY: Modified-site
                (B) LOCATION: 2
                (D) OTHER INFORMATION: /note= "Wherein Xaa is a Basic
                    Amino Acid"

(ix) FEATURE:
                (A) NAME/KEY: Modified-site
                (B) LOCATION: 3
                (D) OTHER INFORMATION: /note= "Wherein Xaa is a
                    Hydrophobic Residue"

(ix) FEATURE:
                (A) NAME/KEY: Modified-site
                (B) LOCATION: 4
                (D) OTHER INFORMATION: /note= "Wherein Xaa is a
                    Hydrophobic Residue"

(ix) FEATURE:
                (A) NAME/KEY: Modified-site
                (B) LOCATION: 5
                (D) OTHER INFORMATION: /note= "Wherein Xaa is a
                    Hydrophobic Residue"

(ix) FEATURE:
                (A) NAME/KEY: Modified-site
                (B) LOCATION: 6
                (D) OTHER INFORMATION: /note= "Wherein Xaa is Proline or
                    Valine"

(ix) FEATURE:
                (A) NAME/KEY: Modified-site
                (B) LOCATION: 7
                (D) OTHER INFORMATION: /note= "Wherein Xaa is a
                    Hydrophobic Residue"

(xi) SEQUENCE DESCRIPTION: SEQ ID NO: 13:

Leu Xaa Xaa Xaa Xaa Xaa Xaa Arg Lys
1               5

(2) INFORMATION FOR SEQ ID NO: 14:

(i) SEQUENCE CHARACTERISTICS:
        (A) LENGTH: 10 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 2
        (D) OTHER INFORMATION: /note= "Wherein Xaa is a Basic
            Amino Acid"

(ix) FEATURE:
        (A) NAME/KEY: Modified-site
        (B) LOCATION: 3
        (D) OTHER INFORMATION: /note= "Wherein Xaa is a Basic
            Amino Acid"

(ix) FEATURE:
        (A) NAME/KEY: Modified-site
        (B) LOCATION: 4
        (D) OTHER INFORMATION: /note= "Wherein Xaa is a
            Hydrophobic Residue"

(ix) FEATURE:
        (A) NAME/KEY: Modified-site
        (B) LOCATION: 5
        (D) OTHER INFORMATION: /note= "Wherein Xaa is Proline or
            Valine"

(ix) FEATURE:
        (A) NAME/KEY: Modified-site
        (B) LOCATION: 6
        (D) OTHER INFORMATION: /note= "Wherein Xaa is a
            Hydrophobic Residue"

(ix) FEATURE:
        (A) NAME/KEY: Modified-site
        (B) LOCATION: 7
        (D) OTHER INFORMATION: /note= "Wherein Xaa is a
            Hydrophobic Residue"

(ix) FEATURE:
        (A) NAME/KEY: Modified-site
        (B) LOCATION: 8
        (D) OTHER INFORMATION: /note= "Wherein Xaa is a
            Hydrophobic Residue"

(xi) SEQUENCE DESCRIPTION: SEQ ID NO: 14:

Leu Xaa Xaa Xaa Xaa Xaa Xaa Xaa Arg Lys
1               5                   10

(2) INFORMATION FOR SEQ ID NO: 15:

(i) SEQUENCE CHARACTERISTICS:
        (A) LENGTH: 10 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 2
        (D) OTHER INFORMATION: /note= "Wherein Xaa is a Basic
            Amino Acid"

(ix) FEATURE:
        (A) NAME/KEY: Modified-site
        (B) LOCATION: 3

```
        (D) OTHER INFORMATION: /note= "Wherein Xaa is a Basic
            Amino Acid"

(ix) FEATURE:
        (A) NAME/KEY: Modified-site
        (B) LOCATION: 4
        (D) OTHER INFORMATION: /note= "Wherein Xaa is a
            Hydrophobic Residue"

(ix) FEATURE:
        (A) NAME/KEY: Modified-site
        (B) LOCATION: 5
        (D) OTHER INFORMATION: /note= "Wherein Xaa is a
            Hydrophobic Residue"

(ix) FEATURE:
        (A) NAME/KEY: Modified-site
        (B) LOCATION: 6
        (D) OTHER INFORMATION: /note= "Wherein Xaa is a
            Hydrophobic Residue"

(ix) FEATURE:
        (A) NAME/KEY: Modified-site
        (B) LOCATION: 7
        (D) OTHER INFORMATION: /note= "Wherein Xaa is Proline or
            Valine"

(ix) FEATURE:
        (A) NAME/KEY: Modified-site
        (B) LOCATION: 8
        (D) OTHER INFORMATION: /note= "Wherein Xaa is a
            Hydrophobic Residue"

(xi) SEQUENCE DESCRIPTION: SEQ ID NO: 15:

Leu Xaa Xaa Xaa Xaa Xaa Xaa Xaa Arg Lys
1               5                   10

(2) INFORMATION FOR SEQ ID NO: 16:

(i) SEQUENCE CHARACTERISTICS:
        (A) LENGTH: 10 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 2
        (D) OTHER INFORMATION: /note= "Wherein Xaa is a Basic
            Amino Acid"

(ix) FEATURE:
        (A) NAME/KEY: Modified-site
        (B) LOCATION: 3
        (D) OTHER INFORMATION: /note= "Wherein Xaa is a
            Hydrophobic Residue"

(ix) FEATURE:
        (A) NAME/KEY: Modified-site
        (B) LOCATION: 4
        (D) OTHER INFORMATION: /note= "Wherein Xaa is Proline or
            Valine"

(ix) FEATURE:
        (A) NAME/KEY: Modified-site
        (B) LOCATION: 5
        (D) OTHER INFORMATION: /note= "Wherein Xaa is a
            Hydrophobic Residue"

(ix) FEATURE:
        (A) NAME/KEY: Modified-site
        (B) LOCATION: 6
        (D) OTHER INFORMATION: /note= "Wherein Xaa is a
            Hydrophobic Residue"

(ix) FEATURE:
        (A) NAME/KEY: Modified-site
```

(B) LOCATION: 7
            (D) OTHER INFORMATION: /note= "Wherein Xaa is Proline or
                Valine"

(ix) FEATURE:
            (A) NAME/KEY: Modified-site
            (B) LOCATION: 8
            (D) OTHER INFORMATION: /note= "Wherein Xaa is a
                Hydrophobic Residue"

(xi) SEQUENCE DESCRIPTION: SEQ ID NO: 16:

Leu Xaa Xaa Xaa Xaa Xaa Xaa Xaa Arg Lys
1               5                   10

(2) INFORMATION FOR SEQ ID NO: 17:

(i) SEQUENCE CHARACTERISTICS:
            (A) LENGTH: 11 amino acids
            (B) TYPE: amino acid
            (C) STRANDEDNESS: single
            (D) TOPOLOGY: linear (ix) FEATURE:
            (A) NAME/KEY: Modified-site
            (B) LOCATION: 2
            (D) OTHER INFORMATION: /note= "Wherein Xaa is a Basic
                Amino Acid"

(ix) FEATURE:
            (A) NAME/KEY: Modified-site
            (B) LOCATION: 3
            (D) OTHER INFORMATION: /note= "Wherein Xaa is a Basic
                Amino Acid"

(ix) FEATURE:
            (A) NAME/KEY: Modified-site
            (B) LOCATION: 4
            (D) OTHER INFORMATION: /note= "Wherein Xaa is a
                Hydrophobic Residue"

(ix) FEATURE:
            (A) NAME/KEY: Modified-site
            (B) LOCATION: 5
            (D) OTHER INFORMATION: /note= "Wherein Xaa is Proline or
                Valine"

(ix) FEATURE:
            (A) NAME/KEY: Modified-site
            (B) LOCATION: 6
            (D) OTHER INFORMATION: /note= "Wherein Xaa is a
                Hydrophobic Residue"

(ix) FEATURE:
            (A) NAME/KEY: Modified-site
            (B) LOCATION: 7
            (D) OTHER INFORMATION: /note= "Wherein Xaa is a
                Hydrophobic Residue"

(ix) FEATURE:
            (A) NAME/KEY: Modified-site
            (B) LOCATION: 8
            (D) OTHER INFORMATION: /note= "Wherein Xaa is Proline or
                Valine"

(ix) FEATURE:
            (A) NAME/KEY: Modified-site
            (B) LOCATION: 9
            (D) OTHER INFORMATION: /note= "Wherein Xaa is a
                Hydrophobic Residue"

(xi) SEQUENCE DESCRIPTION: SEQ ID NO: 17:

Leu Xaa Xaa Xaa Xaa Xaa Xaa Xaa Xaa Arg Lys
1               5                   10

(2) INFORMATION FOR SEQ ID NO: 18:

(i) SEQUENCE CHARACTERISTICS:
    (A) LENGTH: 10 amino acids
    (B) TYPE: amino acid
    (C) STRANDEDNESS: single
    (D) TOPOLOGY: linear (ix) FEATURE:
    (A) NAME/KEY: Modified-site
    (B) LOCATION: 2
    (D) OTHER INFORMATION: /note= "Wherein Xaa is a
        Hydrophobic Residue"

(ix) FEATURE:
    (A) NAME/KEY: Modified-site
    (B) LOCATION: 3
    (D) OTHER INFORMATION: /note= "Wherein Xaa is Proline or
        Valine"

(ix) FEATURE:
    (A) NAME/KEY: Modified-site
    (B) LOCATION: 4
    (D) OTHER INFORMATION: /note= "Wherein Xaa is a
        Hydrophobic Residue"

(ix) FEATURE:
    (A) NAME/KEY: Modified-site
    (B) LOCATION: 5
    (D) OTHER INFORMATION: /note= "Wherein Xaa is a
        Hydrophobic Residue"

(ix) FEATURE:
    (A) NAME/KEY: Modified-site
    (B) LOCATION: 6
    (D) OTHER INFORMATION: /note= "Wherein Xaa is Proline or
        Valine"

(ix) FEATURE:
    (A) NAME/KEY: Modified-site
    (B) LOCATION: 7
    (D) OTHER INFORMATION: /note= "Wherein Xaa is a
        Hydrophobic Residue"

(xi) SEQUENCE DESCRIPTION: SEQ ID NO: 18:

Leu Xaa Xaa Xaa Xaa Xaa Xaa Arg Arg Lys
1               5                   10

(2) INFORMATION FOR SEQ ID NO: 19:

(i) SEQUENCE CHARACTERISTICS:
        (A) LENGTH: 11 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 3
        (D) OTHER INFORMATION: /note= "Wherein Xaa is a
            Hydrophobic Residue"

(ix) FEATURE:
        (A) NAME/KEY: Modified-site
        (B) LOCATION: 4
        (D) OTHER INFORMATION: /note= "Wherein Xaa is Proline or
            Valine"

(ix) FEATURE:
        (A) NAME/KEY: Modified-site
        (B) LOCATION: 5
        (D) OTHER INFORMATION: /note= "Wherein Xaa is a
            Hydrophobic Residue"

(ix) FEATURE:
        (A) NAME/KEY: Modified-site
        (B) LOCATION: 6
        (D) OTHER INFORMATION: /note= "Wherein Xaa is a Hydrophobic Residue"

(ix) FEATURE:
                 (A) NAME/KEY: Modified-site
                 (B) LOCATION: 7
                 (D) OTHER INFORMATION: /note= "Wherein Xaa is Proline or
                     Valine"

(ix) FEATURE:
                 (A) NAME/KEY: Modified-site
                 (B) LOCATION: 8
                 (D) OTHER INFORMATION: /note= "Wherein Xaa is a
                     Hydrophobic Residue"

(xi) SEQUENCE DESCRIPTION: SEQ ID NO: 19:

```
Leu Lys Xaa Xaa Xaa Xaa Xaa Xaa Arg Arg Lys
1               5                   10
```

(2) INFORMATION FOR SEQ ID NO: 20:

(i) SEQUENCE CHARACTERISTICS:
                 (A) LENGTH: 11 amino acids
                 (B) TYPE: amino acid
                 (C) STRANDEDNESS: single
                 (D) TOPOLOGY: linear (ix) FEATURE:
                 (A) NAME/KEY: Modified-site
                 (B) LOCATION: 1
                 (D) OTHER INFORMATION: /note= "Wherein Xaa is a Basic
                     Amino Acid"

(ix) FEATURE:
                 (A) NAME/KEY: Modified-site
                 (B) LOCATION: 2
                 (D) OTHER INFORMATION: /note= "Wherein Xaa is a Basic
                     Amino Acid"

(ix) FEATURE:
                 (A) NAME/KEY: Modified-site
                 (B) LOCATION: 3
                 (D) OTHER INFORMATION: /note= "Wherein Xaa is a
                     Hydrophobic Residue"

(ix) FEATURE:
                 (A) NAME/KEY: Modified-site
                 (B) LOCATION: 4
                 (D) OTHER INFORMATION: /note= "Wherein Xaa is Proline or
                     Valine"

(ix) FEATURE:
                 (A) NAME/KEY: Modified-site
                 (B) LOCATION: 5
                 (D) OTHER INFORMATION: /note= "Wherein Xaa is a
                     hydrophobic Residue"

(ix) FEATURE:
                 (A) NAME/KEY: Modified-site
                 (B) LOCATION: 6
                 (D) OTHER INFORMATION: /note= "Wherein Xaa is a
                     Hydrophobic Residue"

(ix) FEATURE:
                 (A) NAME/KEY: Modified-site
                 (B) LOCATION: 7
                 (D) OTHER INFORMATION: /note= "Wherein Xaa is Proline or
                     Valine"

(ix) FEATURE:
                 (A) NAME/KEY: Modified-site
                 (B) LOCATION: 8
                 (D) OTHER INFORMATION: /note= "Wherein Xaa is a
                     Hydrophobic Residue"

(ix) FEATURE:
                 (A) NAME/KEY: Modified-site
                 (B) LOCATION: 9

(D) OTHER INFORMATION: /note= "Wherein Xaa is a Basic
                        Amino Acid"

(ix) FEATURE:
                    (A) NAME/KEY: Modified-site
                    (B) LOCATION: 10
                    (D) OTHER INFORMATION: /note= "Wherein Xaa is a Basic
                        Amino Acid"

(ix) FEATURE:
                    (A) NAME/KEY: Modified-site
                    (B) LOCATION: 11
                    (D) OTHER INFORMATION: /note= "Wherein Xaa is a Basic
                        Amino Acid"

(ix) FEATURE:
                    (B) LOCATION: 3,5,6 and 8
                    (D) OTHER INFORMATION: /note= "At least Two of the
                        Residues at Positions 3,5,6 and 8 are Phenylalanine"

(xi) SEQUENCE DESCRIPTION: SEQ ID NO: 20:

Xaa Xaa Xaa Xaa Xaa Xaa Xaa Xaa Xaa Xaa Xaa
1               5                   10

(2) INFORMATION FOR SEQ ID NO: 21:

(i) SEQUENCE CHARACTERISTICS:
                    (A) LENGTH: 11 amino acids
                    (B) TYPE: amino acid
                    (C) STRANDEDNESS: single
                    (D) TOPOLOGY: linear (ix) FEATURE:
                    (A) NAME/KEY: Modified-site
                    (B) LOCATION: 1
                    (D) OTHER INFORMATION: /note= "Wherein Xaa is a Basic
                        Amino Acid"

(ix) FEATURE:
                    (A) NAME/KEY: Modified-site
                    (B) LOCATION: 2
                    (D) OTHER INFORMATION: /note= "Wherein Xaa is a Basic
                        Amino Acid"

(ix) FEATURE:
                    (A) NAME/KEY: Modified-site
                    (B) LOCATION: 3
                    (D) OTHER INFORMATION: /note= "Wherein Xaa is a
                        Hydrophobic Residue"

(ix) FEATURE:
                    (A) NAME/KEY: Modified-site
                    (B) LOCATION: 4
                    (D) OTHER INFORMATION: /note= "Wherein Xaa is Proline or
                        Valine"

(ix) FEATURE:
                    (A) NAME/KEY: Modified-site
                    (B) LOCATION: 5
                    (D) OTHER INFORMATION: /note= "Wherein Xaa is a
                        hydrophobic Residue"

(ix) FEATURE:
                    (A) NAME/KEY: Modified-site
                    (B) LOCATION: 6
                    (D) OTHER INFORMATION: /note= "Wherein Xaa is a
                        Hydrophobic Residue"

(ix) FEATURE:
                    (A) NAME/KEY: Modified-site
                    (B) LOCATION: 7
                    (D) OTHER INFORMATION: /note= "Wherein Xaa is Proline or
                        Valine"

(ix) FEATURE:
                    (A) NAME/KEY: Modified-site
                    (B) LOCATION: 8

```
            (D) OTHER INFORMATION: /note= "Wherein Xaa is a
                Hydrophobic Residue"

(ix) FEATURE:
            (A) NAME/KEY: Modified-site
            (B) LOCATION: 9
            (D) OTHER INFORMATION: /note= "Wherein Xaa is a Basic
                Amino Acid"

(ix) FEATURE:
            (A) NAME/KEY: Modified-site
            (B) LOCATION: 10
            (D) OTHER INFORMATION: /note= "Wherein Xaa is a Basic
                Amino Acid"

(ix) FEATURE:
            (A) NAME/KEY: Modified-site
            (B) LOCATION: 11
            (D) OTHER INFORMATION: /note= "Wherein Xaa is a Basic
                Amino Acid"

(ix) FEATURE:
            (A) NAME/KEY: Modified-site
            (B) LOCATION: 3,5,6 and 8
            (D) OTHER INFORMATION: /note= "At least Two of the
                Residues at Positions 3,5,6 and 8 are Tyrosine"

(xi) SEQUENCE DESCRIPTION: SEQ ID NO: 21:

Xaa Xaa Xaa Xaa Xaa Xaa Xaa Xaa Xaa Xaa Xaa
1               5                   10

(2) INFORMATION FOR SEQ ID NO: 22:

(i) SEQUENCE CHARACTERISTICS:
            (A) LENGTH: 13 amino acids
            (B) TYPE: amino acid
            (C) STRANDEDNESS: <Unknown>
            (D) TOPOLOGY: linear (xi) SEQUENCE DESCRIPTION: SEQ ID NO: 22:

Ile Leu Lys Lys Phe Pro Phe Phe Pro Phe Arg Arg Lys
1               5                   10

(2) INFORMATION FOR SEQ ID NO: 23:

(i) SEQUENCE CHARACTERISTICS:
            (A) LENGTH: 13 amino acids
            (B) TYPE: amino acid
            (C) STRANDEDNESS: <Unknown>
            (D) TOPOLOGY: linear (xi) SEQUENCE DESCRIPTION: SEQ ID NO: 23:

Ile Leu Lys Lys Tyr Pro Tyr Tyr Pro Tyr Arg Arg Lys
1               5                   10

(2) INFORMATION FOR SEQ ID NO: 24:

(i) SEQUENCE CHARACTERISTICS:
            (A) LENGTH: 12 amino acids
            (B) TYPE: amino acid
            (C) STRANDEDNESS: <Unknown>
            (D) TOPOLOGY: linear (xi) SEQUENCE DESCRIPTION: SEQ ID NO: 24:

Ile Leu Lys Lys Trp Pro Trp Trp Pro Trp Arg Lys
1               5                   10

(2) INFORMATION FOR SEQ ID NO: 25:

(i) SEQUENCE CHARACTERISTICS:
            (A) LENGTH: 13 amino acids
```

(B) TYPE: amino acid
        (C) STRANDEDNESS: <Unknown>
        (D) TOPOLOGY: linear (xi) SEQUENCE DESCRIPTION: SEQ ID NO: 25:

Ile Leu Arg Arg Trp Pro Trp Trp Pro Trp Arg Arg Arg
1               5                  10

(2) INFORMATION FOR SEQ ID NO: 26:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: linear (xi) SEQUENCE DESCRIPTION: SEQ ID NO: 26:

Trp Arg Ile Trp Lys Pro Lys Trp Arg Leu Pro Lys Trp
1               5                  10

(2) INFORMATION FOR SEQ ID NO: 27:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (xi) SEQUENCE DESCRIPTION: SEQ ID NO: 27:

Ile Leu Arg Trp Val Trp Trp Val Trp Arg Arg Lys
1               5                  10

(2) INFORMATION FOR SEQ ID NO: 28:

(i) SEQUENCE CHARACTERISTICS:
        (A) LENGTH: 11 amino acids
        (B) TYPE: amino acid
        (C) STRANDEDNESS: <Unknown>
        (D) TOPOLOGY: linear (xi) SEQUENCE DESCRIPTION: SEQ ID NO: 28:

Ile Leu Lys Lys Trp Pro Trp Trp Pro Trp Lys
1               5                  10

(2) INFORMATION FOR SEQ ID NO: 29:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: linear (xi) SEQUENCE DESCRIPTION: SEQ ID NO: 29:

Ile Leu Pro Trp Lys Trp Pro Trp Trp Pro Trp Arg Arg
1               5                  10

(2) INFORMATION FOR SEQ ID NO: 30:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: linear (xi) SEQUENCE DESCRIPTION: SEQ ID NO: 30:

Ile Leu Lys Lys Trp Pro Trp Trp Pro Trp Arg Arg Lys
1               5                  10

```
(2) INFORMATION FOR SEQ ID NO: 31:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: linear (xi) SEQUENCE DESCRIPTION: SEQ ID NO: 31:

Lys Arg Arg Trp Pro Trp Trp Pro Trp Lys Lys Leu Ile
1               5                   10

(2) INFORMATION FOR SEQ ID NO: 32:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: linear (xi) SEQUENCE DESCRIPTION: SEQ ID NO: 32:

Ile Leu Lys Lys Ile Pro Ile Ile Pro Ile Arg Arg Lys
1               5                   10

(2) INFORMATION FOR SEQ ID NO: 33:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (xi) SEQUENCE DESCRIPTION: SEQ ID NO: 33:

Ile Leu Lys Lys Trp Pro Trp Pro Trp Arg Arg Lys
1               5                   10

(2) INFORMATION FOR SEQ ID NO: 34:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: linear (xi) SEQUENCE DESCRIPTION: SEQ ID NO: 34:

Ile Leu Lys Lys Tyr Pro Trp Tyr Pro Trp Arg Arg Lys
1               5                   10

(2) INFORMATION FOR SEQ ID NO: 35:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: linear (xi) SEQUENCE DESCRIPTION: SEQ ID NO: 35:

Ile Leu Lys Lys Phe Pro Trp Phe Pro Trp Arg Arg Lys
1               5                   10

(2) INFORMATION FOR SEQ ID NO: 36:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: linear
```

(xi) SEQUENCE DESCRIPTION: SEQ ID NO: 36:

Ile Leu Lys Lys Phe Pro Phe Trp Pro Trp Arg Arg Lys
1               5                   10

(2) INFORMATION FOR SEQ ID NO: 37:

(i) SEQUENCE CHARACTERISTICS:
            (A) LENGTH: 12 amino acids
            (B) TYPE: amino acid
            (C) STRANDEDNESS: <Unknown>
            (D) TOPOLOGY: linear (xi) SEQUENCE DESCRIPTION: SEQ ID NO: 37:

Ile Leu Arg Tyr Val Tyr Tyr Val Tyr Arg Arg Lys
1               5                   10

(2) INFORMATION FOR SEQ ID NO: 38:

(i) SEQUENCE CHARACTERISTICS:
            (A) LENGTH: 13 amino acids
            (B) TYPE: amino acid
            (C) STRANDEDNESS: <Unknown>
            (D) TOPOLOGY: linear (xi) SEQUENCE DESCRIPTION: SEQ ID NO: 38:

Ile Leu Arg Arg Trp Pro Trp Trp Pro Trp Arg Arg Lys
1               5                   10

(2) INFORMATION FOR SEQ ID NO: 39:

(i) SEQUENCE CHARACTERISTICS:
            (A) LENGTH: 12 amino acids
            (B) TYPE: amino acid
            (C) STRANDEDNESS: <Unknown>
            (D) TOPOLOGY: linear (xi) SEQUENCE DESCRIPTION: SEQ ID NO: 39:

Ile Leu Arg Arg Trp Pro Trp Trp Pro Trp Arg Lys
1               5                   10

(2) INFORMATION FOR SEQ ID NO: 40:

(i) SEQUENCE CHARACTERISTICS:
            (A) LENGTH: 12 amino acids
            (B) TYPE: amino acid
            (C) STRANDEDNESS: <Unknown>
            (D) TOPOLOGY: linear (xi) SEQUENCE DESCRIPTION: SEQ ID NO: 40:

Ile Leu Lys Trp Pro Trp Trp Pro Trp Arg Arg Lys
1               5                   10

(2) INFORMATION FOR SEQ ID NO: 41:

(i) SEQUENCE CHARACTERISTICS:
            (A) LENGTH: 11 amino acids
            (B) TYPE: amino acid
            (C) STRANDEDNESS: <Unknown>
            (D) TOPOLOGY: linear (xi) SEQUENCE DESCRIPTION: SEQ ID NO: 41:

Ile Leu Lys Trp Pro Trp Trp Pro Trp Arg Lys
1               5                   10

(2) INFORMATION FOR SEQ ID NO: 42:

(i) SEQUENCE CHARACTERISTICS:

```
            (A) LENGTH: 12 amino acids
            (B) TYPE: amino acid
            (C) STRANDEDNESS: <Unknown>
            (D) TOPOLOGY: linear (xi) SEQUENCE DESCRIPTION: SEQ ID NO: 42:

Ile Leu Arg Trp Pro Trp Trp Pro Trp Arg Arg Lys
1               5                   10

(2) INFORMATION FOR SEQ ID NO: 43:

(i) SEQUENCE CHARACTERISTICS:
            (A) LENGTH: 12 amino acids
            (B) TYPE: amino acid
            (C) STRANDEDNESS: <Unknown>
            (D) TOPOLOGY: linear (xi) SEQUENCE DESCRIPTION: SEQ ID NO: 43:

Lys Arg Arg Trp Pro Trp Trp Pro Trp Arg Leu Ile
1               5                   10

(2) INFORMATION FOR SEQ ID NO: 44:

(i) SEQUENCE CHARACTERISTICS:
            (A) LENGTH: 11 amino acids
            (B) TYPE: amino acid
            (C) STRANDEDNESS: <Unknown>
            (D) TOPOLOGY: linear (xi) SEQUENCE DESCRIPTION: SEQ ID NO: 44:

Ile Leu Trp Pro Trp Trp Pro Trp Arg Arg Lys
1               5                   10

(2) INFORMATION FOR SEQ ID NO: 45:

(i) SEQUENCE CHARACTERISTICS:
            (A) LENGTH: 13 amino acids
            (B) TYPE: amino acid
            (C) STRANDEDNESS: <Unknown>
            (D) TOPOLOGY: linear (xi) SEQUENCE DESCRIPTION: SEQ ID NO: 45:

Ile Leu Lys Lys Trp Pro Trp Trp Pro Trp Lys Lys Lys
1               5                   10

(2) INFORMATION FOR SEQ ID NO: 46:

(i) SEQUENCE CHARACTERISTICS:
            (A) LENGTH: 21 amino acids
            (B) TYPE: amino acid
            (C) STRANDEDNESS: <Unknown>
            (D) TOPOLOGY: linear (xi) SEQUENCE DESCRIPTION: SEQ ID NO: 46:

Ile Leu Arg Trp Pro Trp Trp Pro Trp Arg Arg Lys Ile Met Ile Le
1               5                   10                  15

Lys Lys Ala Gly Ser
            20

(2) INFORMATION FOR SEQ ID NO: 47:

(i) SEQUENCE CHARACTERISTICS:
            (A) LENGTH: 20 amino acids
            (B) TYPE: amino acid
            (C) STRANDEDNESS: <Unknown>
            (D) TOPOLOGY: linear (xi) SEQUENCE DESCRIPTION: SEQ ID NO: 47:
```

Ile Leu Arg Trp Pro Trp Trp Pro Trp Arg Arg Lys Met Ile Leu Ly
1               5                   10                  15

Lys Ala Gly Ser
        20

(2) INFORMATION FOR SEQ ID NO: 48:

(i) SEQUENCE CHARACTERISTICS:
        (A) LENGTH: 21 amino acids
        (B) TYPE: amino acid
        (C) STRANDEDNESS: <Unknown>
        (D) TOPOLOGY: linear (xi) SEQUENCE DESCRIPTION: SEQ ID NO: 48:

Ile Leu Arg Trp Pro Trp Trp Pro Trp Arg Arg Lys Asp Met Ile Le
1               5                   10                  15

Lys Lys Ala Gly Ser
        20

(2) INFORMATION FOR SEQ ID NO: 49:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: linear (xi) SEQUENCE DESCRIPTION: SEQ ID NO: 49:

Ile Leu Lys Lys Trp Ala Trp Trp Pro Trp Arg Arg Lys
1               5                   10

(2) INFORMATION FOR SEQ ID NO: 50:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: linear (xi) SEQUENCE DESCRIPTION: SEQ ID NO: 50:

Ile Leu Lys Lys Trp Pro Trp Ala Trp Arg Arg Lys
1               5                   10

(2) INFORMATION FOR SEQ ID NO: 51:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: linear (xi) SEQUENCE DESCRIPTION: SEQ ID NO: 51:

Trp Trp Lys Lys Trp Pro Trp Trp Pro Trp Arg Arg Lys
1               5                   10

(2) INFORMATION FOR SEQ ID NO: 52:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (xi) SEQUENCE DESCRIPTION: SEQ ID NO: 52:

Leu Lys Lys Trp Pro Trp Trp Pro Trp Arg Arg Lys
1               5                   10

(2) INFORMATION FOR SEQ ID NO: 53:

(i) SEQUENCE CHARACTERISTICS:
        (A) LENGTH: 8 amino acids
        (B) TYPE: amino acid
        (C) STRANDEDNESS: <Unknown>
        (D) TOPOLOGY: linear (xi) SEQUENCE DESCRIPTION: SEQ ID NO: 53:

Pro Trp Trp Pro Trp Arg Arg Lys
1               5

(2) INFORMATION FOR SEQ ID NO: 54:

(i) SEQUENCE CHARACTERISTICS:
        (A) LENGTH: 21 amino acids
        (B) TYPE: amino acid
        (C) STRANDEDNESS: <Unknown>
        (D) TOPOLOGY: linear (xi) SEQUENCE DESCRIPTION: SEQ ID NO: 54:

Ile Leu Lys Lys Trp Pro Trp Trp Pro Trp Arg Arg Lys Met Ile Le
1               5                   10                  15

Lys Lys Ala Gly Ser
            20

(2) INFORMATION FOR SEQ ID NO: 55:

(i) SEQUENCE CHARACTERISTICS:
        (A) LENGTH: 20 amino acids
        (B) TYPE: amino acid
        (C) STRANDEDNESS: <Unknown>
        (D) TOPOLOGY: linear (xi) SEQUENCE DESCRIPTION: SEQ ID NO: 55:

Ile Leu Lys Lys Trp Pro Trp Trp Pro Trp Arg Arg Met Ile Leu Ly
1               5                   10                  15

Lys Ala Gly Ser
        20

(2) INFORMATION FOR SEQ ID NO: 56:

(i) SEQUENCE CHARACTERISTICS:
        (A) LENGTH: 21 amino acids
        (B) TYPE: amino acid
        (C) STRANDEDNESS: <Unknown>
        (D) TOPOLOGY: linear (xi) SEQUENCE DESCRIPTION: SEQ ID NO: 56:

Ile Leu Lys Lys Trp Pro Trp Trp Pro Trp Arg Arg Ile Met Ile Le
1               5                   10                  15

Lys Lys Ala Gly Ser
            20

(2) INFORMATION FOR SEQ ID NO: 57:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (xi) SEQUENCE DESCRIPTION: SEQ ID NO: 57:

Ile Leu Lys Lys Trp Pro Trp Trp Pro Trp Arg Arg Lys Met
1               5                   10

(2) INFORMATION FOR SEQ ID NO: 58:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: linear (xi) SEQUENCE DESCRIPTION: SEQ ID NO: 58:

Ile Leu Lys Lys Trp Pro Trp Trp Pro Trp Arg Arg Met
1               5                   10

(2) INFORMATION FOR SEQ ID NO: 59:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (xi) SEQUENCE DESCRIPTION: SEQ ID NO: 59:

Ile Leu Lys Lys Trp Pro Trp Trp Pro Trp Arg Arg Ile Met
1               5                   10

(2) INFORMATION FOR SEQ ID NO: 60:

(i) SEQUENCE CHARACTERISTICS:
        (A) LENGTH: 11 amino acids
        (B) TYPE: amino acid
        (C) STRANDEDNESS: <Unknown>
        (D) TOPOLOGY: linear (xi) SEQUENCE DESCRIPTION: SEQ ID NO: 60:

Ile Leu Lys Lys Trp Trp Trp Pro Trp Arg Lys
1               5                   10

(2) INFORMATION FOR SEQ ID NO: 61:

(i) SEQUENCE CHARACTERISTICS:
        (A) LENGTH: 11 amino acids
        (B) TYPE: amino acid
        (C) STRANDEDNESS: <Unknown>
        (D) TOPOLOGY: linear (xi) SEQUENCE DESCRIPTION: SEQ ID NO: 61:

Ile Leu Lys Lys Trp Pro Trp Trp Trp Arg Lys
1               5                   10

(2) INFORMATION FOR SEQ ID NO: 62:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: linear (ix) FEATURE:
        (A) NAME/KEY: Modified-site
        (B) LOCATION: 1
        (D) OTHER INFORMATION: /note= "D-Form of Isoleucine"

(xi) SEQUENCE DESCRIPTION: SEQ ID NO: 62:

Ile Leu Lys Lys Trp Pro Trp Trp Pro Trp Arg Arg Lys
1               5                   10

(2) INFORMATION FOR SEQ ID NO: 63:

(i) SEQUENCE CHARACTERISTICS:
    (A) LENGTH: 13 amino acids
    (B) TYPE: amino acid
    (C) STRANDEDNESS: <Unknown>
    (D) TOPOLOGY: linear (ix) FEATURE:
    (A) NAME/KEY: Modified-site
    (B) LOCATION: 13
    (D) OTHER INFORMATION: /note= "D-Form of Lysine"

(xi) SEQUENCE DESCRIPTION: SEQ ID NO: 63:

Ile Leu Lys Lys Trp Pro Trp Trp Pro Trp Arg Arg Lys
1               5                   10

(2) INFORMATION FOR SEQ ID NO: 64:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: linear (ix) FEATURE:
        (A) NAME/KEY: Modified-site
        (B) LOCATION: 1
        (D) OTHER INFORMATION: /note= "D-Form of Isoleucine"

(ix) FEATURE:
        (A) NAME/KEY: Modified-site
        (B) LOCATION: 13
        (D) OTHER INFORMATION: /note= "D-Form of Lysine"

(xi) SEQUENCE DESCRIPTION: SEQ ID NO: 64:

Ile Leu Lys Lys Trp Pro Trp Trp Pro Trp Arg Arg Lys
1               5                   10

(2) INFORMATION FOR SEQ ID NO: 65:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: linear (xi) SEQUENCE DESCRIPTION: SEQ ID NO: 65:

Ile Leu Lys Lys Trp Val Trp Trp Val Trp Arg Arg Lys
1               5                   10

(2) INFORMATION FOR SEQ ID NO: 66:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: linear (xi) SEQUENCE DESCRIPTION: SEQ ID NO: 66:

Ile Leu Lys Lys Trp Pro Trp Trp Val Trp Arg Arg Lys
1               5                   10

(2) INFORMATION FOR SEQ ID NO: 67:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: linear (xi) SEQUENCE DESCRIPTION: SEQ ID NO: 67:

```
Ile Leu Lys Lys Trp Val Trp Pro Trp Arg Arg Lys
1               5                   10
```

(2) INFORMATION FOR SEQ ID NO: 68:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (xi) SEQUENCE DESCRIPTION: SEQ ID NO: 68:

```
Lys Arg Arg Trp Val Trp Trp Val Trp Arg Leu Ile
1               5                   10
```

(2) INFORMATION FOR SEQ ID NO: 69:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (xi) SEQUENCE DESCRIPTION: SEQ ID NO: 69:

```
Ile Lys Lys Trp Pro Trp Trp Pro Trp Arg Arg Lys
1               5                   10
```

(2) INFORMATION FOR SEQ ID NO: 70:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (xi) SEQUENCE DESCRIPTION: SEQ ID NO: 70:

```
Ile Leu Lys Lys Pro Trp Trp Pro Trp Arg Arg Lys
1               5                   10
```

(2) INFORMATION FOR SEQ ID NO: 71:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (xi) SEQUENCE DESCRIPTION: SEQ ID NO: 71:

```
Ile Leu Lys Lys Trp Trp Trp Pro Trp Arg Arg Lys
1               5                   10
```

(2) INFORMATION FOR SEQ ID NO: 72:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (xi) SEQUENCE DESCRIPTION: SEQ ID NO: 72:

```
Ile Leu Lys Lys Trp Pro Trp Trp Arg Arg Lys
1               5                   10
```

(2) INFORMATION FOR SEQ ID NO: 73:

(i) SEQUENCE CHARACTERISTICS:
        (A) LENGTH: 12 amino acids
        (B) TYPE: amino acid

```
        (C) STRANDEDNESS: <Unknown>
        (D) TOPOLOGY: linear (xi) SEQUENCE DESCRIPTION: SEQ ID NO: 73:

Ile Leu Lys Lys Trp Pro Trp Trp Pro Arg Arg Lys
1               5                   10

(2) INFORMATION FOR SEQ ID NO: 74:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (xi) SEQUENCE DESCRIPTION: SEQ ID NO: 74:

Ile Leu Lys Lys Trp Pro Trp Trp Pro Trp Arg Arg
1               5                   10

(2) INFORMATION FOR SEQ ID NO: 75:

(i) SEQUENCE CHARACTERISTICS:
        (A) LENGTH: 11 amino acids
        (B) TYPE: amino acid
        (C) STRANDEDNESS: <Unknown>
        (D) TOPOLOGY: linear (xi) SEQUENCE DESCRIPTION: SEQ ID NO: 75:

Ile Leu Lys Lys Trp Pro Trp Trp Pro Trp Arg
1               5                   10

(2) INFORMATION FOR SEQ ID NO: 76:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (xi) SEQUENCE DESCRIPTION: SEQ ID NO: 76:

Ala Leu Arg Trp Pro Trp Trp Pro Trp Arg Arg Lys
1               5                   10

(2) INFORMATION FOR SEQ ID NO: 77:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (xi) SEQUENCE DESCRIPTION: SEQ ID NO: 77:

Ile Ala Arg Trp Pro Trp Trp Pro Trp Arg Arg Lys
1               5                   10

(2) INFORMATION FOR SEQ ID NO: 78:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (xi) SEQUENCE DESCRIPTION: SEQ ID NO: 78:

Ile Leu Ala Trp Pro Trp Trp Pro Trp Arg Arg Lys
1               5                   10
```

(2) INFORMATION FOR SEQ ID NO: 79:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (xi) SEQUENCE DESCRIPTION: SEQ ID NO: 79:

Ile Leu Arg Ala Pro Trp Trp Pro Trp Arg Arg Lys
1               5                   10

(2) INFORMATION FOR SEQ ID NO: 80:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (xi) SEQUENCE DESCRIPTION: SEQ ID NO: 80:

Ile Leu Arg Trp Ala Trp Trp Pro Trp Arg Arg Lys
1               5                   10

(2) INFORMATION FOR SEQ ID NO: 81:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (xi) SEQUENCE DESCRIPTION: SEQ ID NO: 81:

Ile Leu Arg Trp Pro Ala Trp Pro Trp Arg Arg Lys
1               5                   10

(2) INFORMATION FOR SEQ ID NO: 82:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (xi) SEQUENCE DESCRIPTION: SEQ ID NO: 82:

Ile Leu Arg Trp Pro Trp Ala Pro Trp Arg Arg Lys
1               5                   10

(2) INFORMATION FOR SEQ ID NO: 83:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (xi) SEQUENCE DESCRIPTION: SEQ ID NO: 83:

Ile Leu Arg Trp Pro Trp Trp Ala Trp Arg Arg Lys
1               5                   10

(2) INFORMATION FOR SEQ ID NO: 84:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (xi) SEQUENCE DESCRIPTION: SEQ ID NO: 84:

```
Ile Leu Arg Trp Pro Trp Trp Pro Ala Arg Arg Lys
1               5                   10
```

(2) INFORMATION FOR SEQ ID NO: 85:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (xi) SEQUENCE DESCRIPTION: SEQ ID NO: 85:

```
Ile Leu Arg Trp Pro Trp Trp Pro Trp Ala Arg Lys
1               5                   10
```

(2) INFORMATION FOR SEQ ID NO: 86:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (xi) SEQUENCE DESCRIPTION: SEQ ID NO: 86:

```
Ile Leu Arg Trp Pro Trp Trp Pro Trp Arg Ala Lys
1               5                   10
```

(2) INFORMATION FOR SEQ ID NO: 87:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (xi) SEQUENCE DESCRIPTION: SEQ ID NO: 87:

```
Ile Leu Arg Trp Pro Trp Trp Pro Trp Arg Arg Ala
1               5                   10
```

(2) INFORMATION FOR SEQ ID NO: 88:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: linear (xi) SEQUENCE DESCRIPTION: SEQ ID NO: 88:

```
Trp Trp Pro Trp Arg Arg Lys
1               5
```

(2) INFORMATION FOR SEQ ID NO: 89:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: linear (xi) SEQUENCE DESCRIPTION: SEQ ID NO: 89:

```
Ile Leu Lys Lys Trp Pro Trp
1               5
```

(2) INFORMATION FOR SEQ ID NO: 90:

(i) SEQUENCE CHARACTERISTICS:
        (A) LENGTH: 9 amino acids (B) TYPE: amino acid
(C) STRANDEDNESS: <Unknown>
(D) TOPOLOGY: linear (xi) SEQUENCE DESCRIPTION: SEQ ID NO: 90:

Trp Pro Trp Trp Pro Trp Arg Arg Lys
1               5

COMPOSITIONS AND METHODS FOR TREATING INFECTIONS USING ANALOGUES OF INDOLICIDIN

CROSS-RELATED APPLICATIONS

This application is a continuation of allowed U.S. patent application Ser. No. 09/667,486, filed Sep. 22, 2000 and issued as U.S. Pat. No. 6,538,106 on Mar. 25, 2003, which is a continuation of U.S. patent application Ser. No. 08/915,314, filed Aug. 20, 1997 and issued as U.S. Pat. No. 6,180,604 on Jan. 30, 2001, which application claims priority from U.S. Provisional Application No. 60/024,754, filed Aug. 21, 1996 and U.S. Provisional Application No. 60/034,949, filed Jan. 13, 1997.

TECHNICAL FIELD

The present invention relates generally to treatment of microorganism-caused infections, and more specifically, to compositions comprising indolicidin analogues, polymer-modified analogues, and their uses in treating infections.

BACKGROUND OF THE INVENTION

For most healthy individuals, infections are irritating, but not generally life-threatening. Many infections are successfully combated by the immune system of the individual. Treatment is an adjunct and is generally readily available in developed countries. However, infectious diseases are a serious concern in developing countries and in immunocompromised individuals.

In developing countries, the lack of adequate sanitation and consequent poor hygiene provide an environment that fosters bacterial, parasitic, fungal and viral infections. Poor hygiene and nutritional deficiencies may diminish the effectiveness of natural barriers, such as skin and mucous membranes, to invasion by infectious agents or the ability of the immune system to clear the agents. As well, a constant onslaught of pathogens may stress the immune system defenses of antibody production and phagocytic cells (e.g., polymorphic neutrophils) to subnormal levels. A breakdown of host defenses can also occur due to conditions such as circulatory disturbances, mechanical obstruction, fatigue, smoking, excessive drinking, genetic defects, AIDS, bone marrow transplant, cancer, and diabetes. An increasingly prevalent problem in the world is opportunistic infections in individuals who are HIV positive.

Although vaccines may be available to protect against some of these organisms, vaccinations are not always feasible, due to factors such as inadequate delivery mechanisms and economic poverty, or effective, due to factors such as delivery too late in the infection, inability of the patient to mount an immune response to the vaccine, or evolution of the pathogen. For other pathogenic agents, no vaccines are available. When protection against infection is not possible, treatment of infection is generally pursued. The major weapon in the arsenal of treatments is antibiotics. While antibiotics have proved effective against many bacteria and thus saved countless lives, they are not a panacea. The overuse of antibiotics in certain situations has promoted the spread of resistant bacterial strains. And of great importance, antibacterials are useless against viral infections.

A variety of organisms make cationic (positively charged) peptides, molecules used as part of a non-specific defense mechanism against microorganisms. When isolated, these peptides are toxic to a wide variety of microorganisms, including bacteria, fungi, and certain enveloped viruses. One cationic peptide found in neutrophils is indolicidin. While indolicidin acts against many pathogens, notable exceptions and varying degrees of toxicity exist.

Although cationic peptides show efficacy in vitro against a variety of pathogenic cells including gram-positive bacteria, gram-negative bacteria, and fungi, these peptides are generally toxic to mammals when injected, and therapeutic indices are usually quite small. Approaches to reducing toxicity have included development of a derivative or delivery system that masks structural elements involved in the toxic response or that improves the efficacy at lower doses. Other approaches under evaluation include liposomes and micellular systems to improve the clinical effects of peptides, proteins, and hydrophobic drugs, and cyclodextrins to sequester hydrophobic surfaces during administration in aqueous media. For example, attachment of polyethylene glycol (PEG) polymers, most often by modification of amino groups, improves the medicinal value of some proteins such as asparaginase and adenosine deaminase, and increases circulatory half-lives of peptides such as interleukins.

None of these approaches are shown to improve administration of cationic peptides. For example, methods for the stepwise synthesis of polysorbate derivatives that can modify peptides by acylation reactions have been developed, but acylation alters the charge of a modified cationic peptide and frequently reduces or eliminates the antimicrobial activity of the compound. Thus, for delivery of cationic peptides, as well as other peptides and proteins, there is a need for a system combining the properties of increased circulatory half-lives with the ability to form a micellular structure.

The present invention discloses analogues of indolicidin, designed to broaden its range and effectiveness, and further provide other related advantages. The present invention also provides methods and compositions for modifying peptides, proteins, antibiotics and the like to reduce toxicity, as well as providing other advantages.

SUMMARY OF THE INVENTION

The present invention generally provides indolicidin analogues. In related aspects, an indolicidin analogue is provided, comprising up to 25 amino acids and containing the formula: RXZXXZXB (SEQ ID NO: 1); BXZXXZXB (SEQ ID NO: 2) wherein at least one Z is valine; BBBXZXXZXB (SEQ ID NO: 3); BXZXXZXBBB$_n$(AA)$_n$MILBBAGS (SEQ ID NOS: 4-7); BXZXXZXBB(AA)$_n$M (SEQ ID NOS: 8-9); LBB$_n$XZ$_n$XXZ$_n$XRK (SEQ ID NOS: 10-17); LK$_n$XZXXZXRRK (SEQ ID NOS: 18-19); BBXZXXZX-BBB (SEQ ID NO: 20), wherein at least two X residues are phenylalanine; BBXZXXZXBBB (SEQ ID NO: 21), wherein at least two X residues are tyrosine; and wherein Z is proline or valine; X is a hydrophobic residue; B is a basic amino acid; AA is any amino acid, and n is 0 or 1. In preferred embodiments, Z is proline, X is tryptophan and B is arginine or lysine. In other aspects, indolicidin analogues having specific sequences are provided. In certain embodiments, the indolicidin analogues are coupled to form a branched peptide. In other embodiments, the analogue has one or more amino acids altered to a corresponding D-amino acid, and in certain preferred embodiments, the N-terminal and/or the C-terminal amino acid is a D-amino acid. Other preferred modifications include analogues that are acetylated at the N-terminal amino acid, amidated at the C-terminal amino acid, esterified at the C-terminal amino acid, modified by incorporation of homoserine/homoserine lactone at the C-terminal amino acid, and conjugated with polyethylene glycol or derivatives thereof.

In other aspects, the invention provides an isolated nucleic acid molecule whose sequence comprises one or more coding sequences of the indolicidin analogues, expression vectors, and host cells transfected or transformed with the expression vector.

Other aspects provide a pharmaceutical composition comprising at least one indolicidin analogue and a physiologically acceptable buffer, optionally comprising an antibiotic agent. Preferred combinations include I L K K F P F F P F R R K (SEQ ID NO: 22) and Ciprofloxacin; I L K K F P F F P F R R K (SEQ ID NO: 22) and Mupirocin; I L K K Y P Y Y P Y R R K (SEQ ID NO: 23) and Mupirocin; I L K K W P W W P W R K (SEQ ID NO:24) and Mupirocin; I L R R W P W W P W R R R (SEQ ID NO: 25) and Piperacillin; W R I W K P K W R L P K W (SEQ ID NO: 26) and Ciprofloxacin; W R I W K P K W R L P K W (SEQ ID NO: 26) and Mupirocin; W R I W K P K W R L P K W (SEQ ID NO: 26) and Piperacillin; I L R W V W W V W R R K (SEQ ID NO: 27) and Piperacillin; and I L K K W P W W P W K (SEQ ID NO: 28) and Mupirocin. In other embodiments, the pharmaceutical composition further comprises an antiviral agent, (e.g., acyclovir; amantadine hydrochloride; didanosine; edoxudine; famciclovir; foscarnet; ganciclovir; idoxuridine; interferon; lamivudine; nevirapine; penciclovir; podophyllotoxin; ribavirin; rimantadine; sorivudine; stavudine; trifluridine; vidarabine; zalcitabine and zidovudine); an antiparasitic agent (e.g. 8-hydroxyquinoline derivatives; cinchona alkaloids; nitroimidazole derivatives; piperazine derivatives; pyrimidine derivatives and quinoline derivatives, albendazole; atovaquone; chloroquine phosphate; diethylcarbamazine citrate; eflornithine; halofantrine; iodoquinol; ivermectin; mebendazole; mefloquine hydrochloride; melarsoprol B; metronidazole; niclosamide; nifurtimox; paromomycin; pentamidine isethionate; piperazine; praziquantel; primaquine phosphate; proguanil; pyrantel pamoate; pyrimethamine; pyrvinium pamoate; quinidine gluconate; quinine sulfate; sodium stibogluconate; suramin and thiabendazole); an antifungal agent (e.g., allylamines; imidazoles; pyrimidines and triazoles, 5-fluorocytosine; amphotericin B; butoconazole; chlorphenesin; ciclopirox; clioquinol; clotrimazole; econazole; fluconazole; flucytosine; griseofulvin; itraconazole; ketoconazole; miconazole; naftifine hydrochloride; nystatin; selenium sulfide; sulconazole; terbinafine hydrochloride; terconazole; tioconazole; tolnaftate and undecylenate). In yet other embodiments, the composition is incorporated in a liposome or a slow-release vehicle.

In yet another aspect, the invention provides a method of treating an infection, comprising administering to a patient a therapeutically effective amount of a pharmaceutical composition. The infection may be caused by, for example, a microorganism, such as a bacterium (e.g.,Gram-negative or Gram-positive bacterium or anaerobe; examples are *Acinetobacter* spp., *Enterobacter* spp., *E. coli*, *H. influenzae*, *K. pneumoniae*, *P. aeruginosa*, *S. marcescens* and *S. maltophilia*, *Bordetella pertussis*; *Brucella* spp.; *Campylobacter* spp.; *Haemophilus ducreyi*; *Helicobacter pylori*; *Legionella* spp.; *Moraxella catarrhalis*; *Neisseria* spp.; *Salmonella* spp.; *Shigella* spp. and *Yersinia* spp.; *E. faecalis*, *S. aureus*, *E. faecium*, *S. pyogenes*, *S. pneumoniae* and coagulase-negative staphylococci; *Bacillus* spp.; *Corynebacterium* spp.; Diphtheroids; *Listeria* spp. and Viridans Streptococci.; *Clostridium* spp., *Bacteroides* spp. and *Peptostreptococcus* spp.; *Borrelia* spp.; *Chlamydia* spp.; *Mycobacterium* spp.; *Mycoplasma* spp.; *Propionibacterium acne*; *Rickettsia* spp.; *Treponema* spp. and *Ureaplasma* spp.) fungus (e.g., yeast and/or mold), parasite (e.g., protozoan, nematode, cestode and trematode, such as *Babesia* spp.; *Balantidium coli*; *Blastocystis hominis*; *Cryptosporidium parvum*; *Encephalitozoon* spp.; *Entamoeba* spp.; *Giardia lamblia*; *Leishmania* spp.; *Plasmodium* spp.; *Toxoplasma gondii*; *Trichomonas* spp. *Trypanosoma* spp, *Ascaris lumbricoides*; *Clonorchis sinensis*; *Eehinococcus* spp.; *Fasciola hepatic*, *Fasciolopsis buski*; *Heterophyes heterophyes*; *Hymenolepis* spp.; *Schistosoma* spp.; *Taenia* spp. and *Trichinella spiralis*) or virus (e.g., Alphavirus; Arenavirus; Bunyavirus; Coronavirus; Enterovirus; Filovirus; Flavivirus; Hantavirus; HTLV-BLV; Influenzavirus; Lentivirus; Lyssavirus; Paramyxovirus; Reovirus; Rhinovirus and Rotavirus, Adenovirus; Cytomegalovirus; Hepadnavirus; Molluscipoxvirus; Orthopoxvirus; Papillomavirus; Parvovirus; Polyomavirus; Simplexvirus and Varicellovirus).

In other aspects, a composition is provided, comprising an indolicidin analogue and an antibiotic. In addition, a device, which may be a medical device, is provided that is coated with the indolicidin analogue and may further comprise an antibiotic agent.

In other aspects, antibodies that react specifically with any one of the analogues described herein are provided. The antibody is preferably a monoclonal antibody or single chain antibody.

In a preferred aspect, the invention provides a composition comprising a compound modified by derivatization of an amino group with a conjugate comprising activated polyoxyalkylene glycol and a fatty acid. In preferred embodiments, the conjugate further comprises sorbitan linking the polyoxyalkylene glycol and fatty acid, and more preferably is polysorbate. In preferred embodiments, the fatty acid is from 12-18 carbons, and the polyoxyalkylene glycol is polyoxyethylene, such as with a chain length of from 2 to 100. In certain embodiments, the compound is a peptide or protein, such as a cationic peptide (e.g., indolicidin or an indolicidin analogue). In preferred embodiments, the polyoxyalkylene glycol is activated by irradiation with ultraviolet light.

The invention also provides a method of making a compound modified with a conjugate of an activated polyoxyalkylene glycol and a fatty acid, comprising: (a) freezing a mixture of the conjugate of an activated polyoxyalkylene glycol and fatty acid with the compound; and (b) lyophilizing the frozen mixture; wherein the compound has a free amino group. In preferred embodiments, the compound is a peptide or antibiotic. In other preferred embodiments, the mixture in step (a) is in an acetate buffer. In a related aspect, the method comprises mixing the conjugate of an activated polyoxyalkylene glycol and fatty acid with the compound; for a time sufficient to form modified compounds, wherein the mixture is in a carbonate buffer having a pH greater than 8.5 and the compound has a free amino group. The modified compound may be isolated by reversed-phase HPLC and/or precipitation from an organic solvent.

The invention also provides a pharmaceutical composition comprising at least one modified compound and a physiologically acceptable buffer. and in certain embodiments, further comprises an antibiotic agent, antiviral agent, an antiparasitic agent, and/or antifungal agent. The composition may be used to treat an infection, such as those caused by a microorganism (e.g., bacterium, fungus, parasite and virus).

These and other aspects of the present invention will become evident upon reference to the following detailed description and attached drawings. In addition, various references are set forth below which describe in more detail certain procedures or compositions (e.g., plasmids, etc.), and are therefore incorporated by reference in their entirety.

BRIEF DESCRIPTION OF THE DRAWINGS

FIG. 4 is a graph presenting the extent of solubility of MBI 11CN peptide in various buffers.

FIG. 5 is a reversed phase HPLC profile of MBI 11CN in formulation C1 (left graph panel) and formulation D (right graph panel).

FIG. 7 presents results of ANTS/DPX dye release of egg PC liposomes at various ratios of lipid to protein.

FIG. 8 presents graphs showing the activity of MBI 11B7CN against mid-log cells grown in terrific broth (TB) or Luria-Bretani broth (LB).

DETAILED DESCRIPTION OF THE INVENTION

Figure 1:
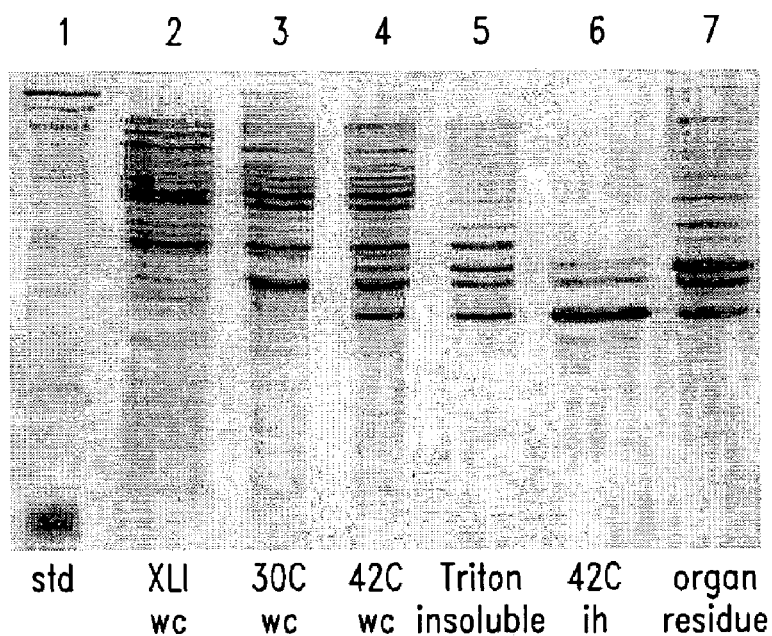
FIG. 1 is an SDS-PAGE showing the extraction profile of inclusion bodies (ib) from whole cells containing MBI-11 fusion protein. The fusion protein band is indicated by the arrow head. Lane 1, protein standards; lane 2, total lysate of XL1 Blue without plasmid; lane 3, total lysate of XL1 Blue (pR2h-11, pGP1-2), cultivated at 30° C.; lane 4, total lysate of XL1 Blue (pR2h-11, pGP1-2), induced at 42° C.; lane 5, insoluble fraction of inclusion bodies after Triton X100 wash; lane 6, organic extract of MBI-11 fusion protein; lane 7, concentrated material not soluble in organic extraction solvent.

Prior to setting forth the invention, it may be helpful to an understanding thereof to set forth definitions of certain terms that are used herein.

The amino acid designations herein are set forth as either the standard one- or three-letter code. A capital letter indicates an L-form amino acid; a small letter indicates a D-form amino acid.

As used herein, "indolicidin" refers to an antimicrobial cationic peptide. Indolicidins may be isolated from a variety of organisms. One indolicidin is isolated from bovine neutrophils and is a 13 amino acid peptide amidated at the carboxy-terminus in its native form (Selsted et al., J. Biol. Chem. 267:4292, 1992). An amino acid sequence of indolicidin is presented in SEQ ID NO: 1.

As used herein, a "peptide analogue", "analogue", or "variant" of indolicidin is at least 5 amino acids in length, has at least one basic amino acid (e.g., arginine and lysine) and has anti-microbial activity. Unless otherwise indicated, a named amino acid refers to the L-form, Basic amino acids include arginine, lysine, and derivatives. Hydrophobic residues include tryptophan, phenylalanine, isoleucine, leucine, valine, and derivatives.

Also included within the scope of the present invention are amino acid derivatives that have been altered by chemical means, such as methylation (e.g., α methylvaline), amidation, especially of the C-terminal amino acid by an alkylamine (e.g., ethylamine, ethanolamine, and ethylene diamine) and alteration of an amino acid side chain, such as acylation of the ε-amino group of lysine. Other amino acids that may be incorporated in the analogue include any of the D-amino acids corresponding to the 20 L-amino acids commonly found in proteins, imino amino acids, rare amino acids, such as hydroxylysine, or non-protein amino acids, such as homoserine and ornithine. A peptide analogue may have none or one or more of these derivatives, and D-amino acids. In addition, a peptide may also be synthesized as a retro-, inverto- or retro-inverto-peptide.

A. Indolicidin Analogues

As noted above, the present invention provides indolicidin analogues. These analogues may be synthesized by chemical methods, especially using an automated peptide synthesizer, or produced by recombinant methods. The choice of an amino acid sequence is guided by a general formula presented herein.

1. Peptide Characteristics

The present invention provides indolicidin analogues. The analogues are at least 5 or 7 amino acids in length and preferably not more than 15, 20, 25, 27, 30, or 35 amino acids. Analogues from 9 to 14 residues are preferred.

General formulas for peptide analogues in the scope of the present invention may be set forth as:

| | | |
|---|---|---|
| RXZXXZXB (SEQ ID NO: 1) | (1) |
| BXZXXZXB (SEQ ID NO: 2) | (2) |
| BBBXZXXZXB (SEQ ID NO: 3) | (3) |
| BXZXXZXBBB$_n$(AA)$_n$MILBBAGS (SEQ ID NOS: 4-7) | (4) |
| BXZXXZXBB(AA)$_n$M (SEQ ID NOS: 8-9) | (5) |
| LBB$_n$XZ$_n$XXZ$_n$XRK (SEQ ID NOS: 10-17) | (6) |
| LK$_n$XZXXZXRRK (SEQ ID NOS: 18-19) | (7) |
| BBXZXXZXBBB (SEQ ID NO: 20) | (8) |
| BBXZXXZXBBB (SEQ ID NO: 21) | (9) | wherein standard single letter amino abbreviations are used and; Z is proline, glycine or a hydrophobic residue, and preferably Z is proline or valine; X is a hydrophobic residue, such as tryptophan, phenylalanine, isoleucine, leucine and valine, and preferably tryptophan; B is a basic amino acid, preferably arginine or lysine; AA is any amino acid, and n is 0 or 1. In formula (2), at least one Z is valine; in formula (8), at least two Xs are phenylalanine; and in formula (9), at least two Xs are tyrosine. Additional residues may be present at the N-terminus, C-terminus, or both.

As described above, modification of any of the residues including the N- or C-terminus is within the scope of the invention. A preferred modification of the C-terminus is amidation. Other modifications of the C-terminus include esterification and lactone formation. N-terminal modifications include acetylation, acylation, alkylation, PEGylation, myristylation, and the like. Additionally, the peptide may be modified to form an APS-peptide as described below. The peptides may also be labeled, such as with a radioactive label, a fluorescent label, a mass spectrometry tag, biotin and the like.

2. Peptide Synthesis

Peptide analogues may be synthesized by standard chemical methods, including synthesis by automated procedure. In general, peptide analogues are synthesized based on the standard solid-phase Fmoc protection strategy with HATU as the coupling agent. The peptide is cleaved from the solid-phase resin with trifluoroacetic acid containing appropriate scavengers, which also deprotects side chain functional groups. Crude peptide is further purified using preparative reversed-phase chromatography. Other purification methods, such as partition chromatography, gel filtration, gel electrophoresis, or ion-exchange chromatography may be used.

Other synthesis techniques, known in the art, such as the tBoc protection strategy, or use of different coupling reagents or the like can be employed to produce equivalent peptides.

Peptides may be synthesized as a linear molecule or as branched molecules. Branched peptides typically contain a core peptide that provides a number of attachment points for additional peptides. Lysine is most commonly used for the core peptide because it has one carboxyl functional group and two (alpha and epsilon) amine functional groups. Other diamino acids can also be used. Preferably, either two or three levels of geometrically branched lysines are used; these cores form a tetrameric and octameric core structure, respectively (Tam, *Proc. Natl. Acad. Sci. USA* 85:5409, 1988). Schematically, examples of these cores are represented as shown:

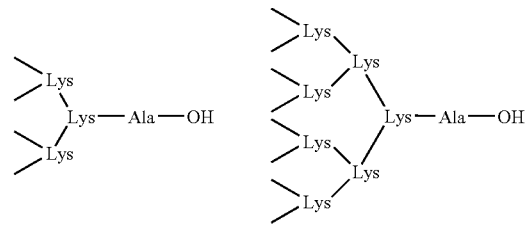

The attachment points for the peptides are typically at their carboxyl functional group to either the alpha or epsilon amine groups of the lysines. To synthesize these multimeric peptides, the solid phase resin is derivatized with the core matrix, and subsequent synthesis and cleavage from the resin follows standard procedures. The multimeric peptide is typically then purified by dialysis against 4 M guanidine hydrochloride then water, using a membrane with a pore size to retain only multimers. The multimeric peptides may be used within the context of this invention as for any of the linear peptides and are preferred for use in generating antibodies to the peptides.

3. Recombinant Production of Peptides

Peptide analogues may alternatively be synthesized by recombinant production (see e.g., U.S. Pat. No. 5,593,866). A variety of host systems are suitable for production of the peptide analogues, including bacteria (e.g., *E. coli*), yeast (e.g., *Saccharomyces cerevisiae*), insect (e.g., Sf9), and mammalian cells (e.g, CHO, COS-7). Many expression vectors have been developed and are available for each of these hosts. Generally, bacteria cells and vectors that are functional in bacteria are used in this invention. However, at times, it may be preferable to have vectors that are functional in other hosts. Vectors and procedures for cloning and expression in *E. coli* are discussed herein and, for example, in Sambrook et al. (*Molecular Cloning: A Laboratory Manual,* Cold Spring Harbor Laboratory Press, Cold Spring Harbor, N.Y., 1987)

and in Ausubel et al. (*Current Protocols in Molecular Biology,* Greene Publishing Co., 1995).

A DNA sequence encoding one or more indolicidin analogues is introduced into an expression vector appropriate for the host. In preferred embodiments, the analogue gene is cloned into a vector to create a fusion protein. The fusion partner is chosen to contain an anionic region, such that a bacterial host is protected from the toxic effect of the peptide. This protective region effectively neutralizes the antimicrobial effects of the peptide and also may prevent peptide degradation by host proteases. The fusion partner (carrier protein) of the invention may further function to transport the fusion peptide to inclusion bodies, the periplasm, the outer membrane, or the extracellular environment. Carrier proteins suitable in the context of this invention specifically include, but are not limited to, glutathione-S-transferase (GST), protein A from *Staphylococcus aureus,* two synthetic IgG-binding domains (ZZ) of protein A, outer membrane protein F, β-galactosidase (lacZ), and various products of bacteriophage λ and bacteriophage T7. From the teachings provided herein, it is apparent that other proteins may be used as carriers. Furthermore, the entire carrier protein need not be used, as long as the protective anionic region is present. To facilitate isolation of the peptide sequence, amino acids susceptible to chemical cleavage (e.g., CNBr) or enzymatic cleavage (e.g., V8 protease, trypsin) are used to bridge the peptide and fusion partner. For expression in *E. coli,* the fusion partner is preferably a normal intracellular protein that directs expression toward inclusion body formation. In such a case, following cleavage to release the final product, there is no requirement for renaturation of the peptide. In the present invention, the DNA cassette, comprising fusion partner and peptide gene, may be inserted into an expression vector, which can be a plasmid, virus or other vehicle known in the art. Preferably, the expression vector is a plasmid that contains an inducible or constitutive promoter to facilitate the efficient transcription of the inserted DNA sequence in the host. Transformation of the host cell with the recombinant DNA may be carried out by $Ca^{++}$-mediated techniques, by electroporation, or other methods well known to those skilled in the art.

Briefly, a DNA fragment encoding a peptide analogue is derived from an existing cDNA or genomic clone or synthesized. A convenient method is amplification of the gene from a single-stranded template. The template is generally the product of an automated oligonucleotide synthesis. Amplification primers are derived from the 5' and 3' ends of the template and typically incorporate restriction sites chosen with regard to the cloning site of the vector. If necessary, translational initiation and termination codons can be engineered into the primer sequences. The sequence encoding the protein may be codon-optimized for expression in the particular host. Thus, for example, if the analogue fusion protein is expressed in bacteria, codons are optimized for bacterial usage. Codon optimization is accomplished by automated synthesis of the entire gene or gene region, ligation of multiple oligonucleotides, mutagenesis of the native sequence, or other techniques known to those in the art.

At minimum, the expression vector should contain a promoter sequence. However, other regulatory sequences may also be included. Such sequences include an enhancer, ribosome binding site, transcription termination signal sequence, secretion signal sequence, origin of replication, selectable marker, and the like. The regulatory sequences are operationally associated with one another to allow transcription and subsequent translation. In preferred aspects, the plasmids used herein for expression include a promoter designed for expression of the proteins in bacteria. Suitable promoters, including both constitutive and inducible promoters, are widely available and are well known in the art. Commonly used promoters for expression in bacteria include promoters from T7, T3, T5, and SP6 phages, and the trp, lpp, and lac operons. Hybrid promoters (see, U.S. Pat. No. 4,551,433), such as tac and trc, may also be used.

In preferred embodiments, the vector includes a transcription terminator sequence. A "transcription terminator region" is a sequence that provides a signal that terminates transcription by the polymerase that recognizes the selected promoter. The transcription terminator may be obtained from the fusion partner gene or from another gene, as long as it is functional in the host.

Within a preferred embodiment, the vector is capable of replication in bacterial cells. Thus, the vector may contain a bacterial origin of replication. Preferred bacterial origins of replication include f1-ori and col E1 ori, especially the ori derived from pUC plasmids. Low copy number vectors (e.g., pPD100) may also be used, especially when the product is deleterious to the host.

The plasmids also preferably include at least one selectable marker that is functional in the host. A selectable marker gene confers a phenotype on the host that allows transformed cells to be identified and/or selectively grown. Suitable selectable marker genes for bacterial hosts include the chloroamphenicol resistance gene ($Cm^r$), ampicillin resistance gene ($Amp^r$), tetracycline resistance gene ($Tc^r$) kanamycin resistance gene ($Kan^r$), and others known in the art. To function in selection, some markers may require a complementary deficiency in the host.

In some aspects, the sequence of nucleotides encoding the peptide analogue also encodes a secretion signal, such that the resulting peptide is synthesized as a precursor protein, which is subsequently processed and secreted. The resulting secreted protein may be recovered from the periplasmic space or the fermentation medium. Sequences of secretion signals suitable for use are widely available and are well known (von Heijne, *J. Mol. Biol.* 184:99-105, 1985).

The vector may also contain a gene coding for a repressor protein, which is capable of repressing the transcription of a promoter that contains a repressor binding site. Altering the physiological conditions of the cell can depress the promoter. For example, a molecule may be added that competitively binds the repressor, or the temperature of the growth media may be altered. Repressor proteins include, but are not limited to the *E. coli* lacI repressor (responsive to induction by IPTG), the temperature sensitive λcI857 repressor, and the like.

Examples of plasmids for expression in bacteria include the pET expression vectors pET3a, pET 11a, pET 12a-c, and pET 15b (see U.S. Pat. No. 4,952,496; available from Novagen, Madison, Wis.). Low copy number vectors (e.g., pPD100) can be used for efficient overproduction of peptides deleterious to the *E. coli* host (Dersch et al., *FEMS Microbiol. Lett.* 123: 19, 1994).

Bacterial hosts for the T7 expression vectors may contain chromosomal copies of DNA encoding T7 RNA polymerase operably linked to an inducible promoter (e.g., lacUV promoter; see, U.S. Pat. No. 4,952,496), such as found in the *E. coli* strains HMS174(DE3)pLysS, BL21(DE3)pLysS, HMS174(DE3) and BL21(DE3). T7 RNA polymerase can also be present on plasmids compatible with the T7 expression vector. The polymerase may be under control of a lambda promoter and repressor (e.g., pGP1-2; Tabor and Richardson, *Proc. Natl. Acad. Sci. USA* 82: 1074, 1985).

The peptide analogue protein is isolated by standard techniques, such as affinity, size exclusion, or ionic exchange chromatography, HPLC and the like. An isolated peptide should preferably show a major band by Coomassie blue stain of SDS-PAGE that is at least 90% of the material.

4. Generation of Analogues by Amplification-based Semi-random Mutagenesis

Indolicidin analogues can be generated using an amplification (e.g., PCR)-based procedure in which primers are designed to target sequences at the 5' and 3' ends of an encoded parent peptide, for example indolicidin. Amplification conditions are chosen to facilitate misincorporation of nucleotides by the thermostable polymerase during synthesis. Thus, random mutations are introduced in the original sequence, some of which result in amino acid alteration(s). Amplification products may be cloned into a coat protein of a phage vector, such as a phagemid vector, packaged and amplified in an acceptable host to produce a display library.

These libraries can then be assayed for antibiotic activity of the peptides. Briefly, bacteria infected with the library are plated, grown, and overlaid with agarose containing a bacterial strain that the phage are unable to infect. Zones of growth inhibition in the agarose overlay are observed in the area of phage expressing an analogue with anti-bacterial activity. These inhibiting phage are isolated and the cloned peptide sequence determined by DNA sequence analysis. The peptide can then be independently synthesized and its antibiotic activity further investigated.

5. Antibodies to Indolicidin Analogues

Antibodies are typically generated to a specific peptide analogue using multiple antigenic peptides (MAPs) that contain approximately eight copies of the peptide linked to a small non-immunogenic peptidyl core to form an immunogen. (See, in general, Harlow and Lane, supra.) The MAPs are injected subcutaneously into rabbits or into mice or other rodents, where they may have sufficiently long half-lives to facilitate antibody production. After twelve weeks blood samples are taken, serum is separated and tested in an ELISA assay against the original peptide, with a positive result indicating the presence of antibodies specific to the target peptide. This serum can then be stored and used in ELISA assays to specifically measure the amount of the specific analogue. Alternatively, other standard methods of antibody production may be employed, for example generation of monoclonal antibodies.

Within the context of the present invention, antibodies are understood to include monoclonal antibodies, polyclonal antibodies, anti-idiotypic antibodies, antibody fragments (e.g., Fab, and F(ab')$_2$, F$_v$ variable regions, or complementarity determining regions). Antibodies are generally accepted as specific against indolicidin analogues if they bind with a K$_d$ of greater than or equal to $10^{-7}$M, preferably greater than of equal to $10^{-8}$M. The affinity of a monoclonal antibody or binding partner can be readily determined by one of ordinary skill in the art (see Scatchard, *Ann. N.Y. Acad. Sci.* 51:660-672, 1949). Once suitable antibodies have been obtained, they may be isolated or purified by many techniques well known to those of ordinary skill in the art.

Monoclonal antibodies may also be readily generated from hybridoma cell lines using conventional techniques (see U.S. Pat. Nos. RE 32,011, 4,902,614, 4,543,439, and 4,411,993; see also *Antibodies: A Laboratory Manual,* Harlow and Lane (eds.), Cold Spring Harbor Laboratory Press, 1988). Briefly, within one embodiment, a subject animal such as a rat or mouse is injected with peptide, generally administered as an emulsion in an adjuvant such as Freund's complete or incomplete adjuvant in order to increase the immune response. The animal is generally boosted at least once prior to harvest of spleen and/or lymph nodes and immortalization of those cells. Various immortalization techniques, such as mediated by Epstein-Barr virus or fusion to produce a hybridoma, may be used. In a preferred embodiment, immortilization occurs by fusion with a suitable myeloma cell line to create a hybridoma that secretes monoclonal antibody. Suitable myeloma lines include, for example, NS-1 (ATCC No. TIB 18), and P3X63-Ag 8.653 (ATCC No. CRL 1580). The preferred fusion partners do not express endogenous antibody genes. After about seven days, the hybridomas may be screened for the presence of antibodies that are reactive against a telomerase protein. A wide variety of assays may be utilized (see *Antibodies: A Laboratory Manual,* Harlow and Lane (eds.), Cold Spring Harbor Laboratory Press, 1988).

Other techniques may also be utilized to construct monoclonal antibodies (see Huse et al., *Science* 246:1275-1281, 1989; Sastry et al., *Proc. Natl. Acad. Sci. USA* 86:5728-5732, 1989; Alting-Mees et al., *Strategies in Molecular Biology* 3:1-9, 1990; describing recombinant techniques). These techniques include cloning heavy and light chain immunoglobulin cDNA in suitable vectors, such as λImmunoZap(H) and λImmunoZap(L). These recombinants may be screened individually or co-expressed to form Fab fragments or antibodies (see Huse et al., supra; Sastry et al., supra). Positive plaques may subsequently be converted to a non-lytic plasmid that allows high level expression of monoclonal antibody fragments from *E. coli.*

Similarly, portions or fragments, such as Fab and Fv fragments, of antibodies may also be constructed utilizing conventional enzymatic digestion or recombinant DNA techniques to yield isolated variable regions of an antibody. Within one embodiment, the genes which encode the variable region from a hybridoma producing a monoclonal antibody of interest are amplified using nucleotide primers for the variable region. In addition, techniques may be utilized to change a "murine" antibody to a "human" antibody, without altering the binding specificity of the antibody.

B. Testing

Indolicidin analogues of the present invention are assessed either alone or in combination with an antibiotic agent or another analogue for their potential as antibiotic therapeutic agents using a series of assays. Preferably, all peptides are initially assessed in vitro, the most promising candidates selected for further assessment in vivo, and using the results of these assays candidates are selected for pre-clinical studies. The in vitro assays include measurement of antibiotic activity, toxicity, solubility, pharmacology, secondary structure, liposome permeabilization and the like. In vivo assays include assessment of efficacy in animal models, antigenicity, toxicity, and the like. In general, in vitro assays are initially performed, followed by in vivo assays.

1. In vitro Assays

Indolicidin analogues are assessed for antibiotic activity by an assay such as an agarose dilution MIC assay or a broth dilution or time-kill assay. Antibiotic activity is measured as inhibition of growth or killing of a microorganism (e.g., bacteria, fungi). Briefly, a candidate analogue in Mueller Hinton broth supplemented with calcium and magnesium is mixed with molten agarose. Other formulations of broths and agars may be used as long as the peptide analogue can freely diffuse through the medium. The agarose is poured into petri dishes or wells, allowed to solidify, and a test strain is applied to the agarose plate. The test strain is chosen, in part, on the intended application of the analogue. Thus, by way of example, if an analogue with activity against *S. aureus* is desired, an *S. aureus* strain is used. It may be desirable to assay the analogue on several strains and/or on clinical isolates of the test species.

Plates are incubated overnight and, on the following day, inspected visually for bacterial growth. The minimum inhibitory concentration (MIC) of an analogue is the lowest concentration of peptide that completely inhibits growth of the organism. Analogues that exhibit good activity against the test strain, or group of strains, typically having an MIC of less than or equal to 16 µg/ml are selected for further testing.

The selected analogues may be further tested for their toxicity to normal mammalian cells. An exemplary assay is a red blood cell (RBC) (erythrocyte) hemolysis assay. Briefly, red blood cells are isolated from whole blood, typically by centrifugation, and washed free of plasma components. A 1% (v/v) suspension of erythrocytes in isotonic saline is incubated with different concentrations of peptide analogue. Generally, the analogue will be in a suitable formulation buffer. After incubation for approximately 1 hour at 37° C., the cells are centrifuged, and the absorbance of the supernatant at 540 nm is determined. A relative measure of lysis is determined by comparison to absorbance after complete lysis of erythrocytes using $NH_4Cl$ or equivalent (establishing a 100% value). An analogue that is not lytic, or is only moderately lytic, as exemplified in Example 8, is desirable and is suitable for further screening. Other in vitro toxicity assays, for example measurement of toxicity towards cultured mammalian cells, may be used to assess in vitro toxicity.

Solubility of the peptide analogue in formulation buffer is an additional parameter that may be examined. Several different assays may be used, such as appearance in buffer. Briefly, peptide analogue is suspended in solution, such as broth or formulation buffer. The appearance is evaluated according to a scale that ranges from (a) clear, no precipitate, (b) light, diffuse precipitate, to (c) cloudy, heavy precipitate. Finer gradations may be used. In general, less precipitate is more desirable. However, some precipitate may be acceptable.

Additional in vitro assays may be carried out to assess the potential of the analogue as a therapeutic. Such assays include peptide solubility in formulations, pharmacology in blood or plasma, serum protein binding, analysis of secondary structure, for example by circular dichroism, liposome permeabilization, and bacterial inner membrane permeabilization. In general, it is desirable that analogues are soluble and perform better than indolicidin.

2. In vivo Assays

Analogues selected on the basis of the results from the in vitro assays can be tested in vivo for efficacy, toxicity and the like.

The antibiotic activity of selected analogues may be assessed in vivo for their ability to ameliorate microbial infections using animal models. Within these assays, an analogue is useful as a therapeutic if inhibition of microorganismal growth compared to inhibition with vehicle alone is statistically significant. This measurement can be made directly from cultures isolated from body fluids or sites, or indirectly, by assessing survival rates of infected animals. For assessment of antibacterial activity several animal models are available, such as acute infection models including those in which (a) normal mice receive a lethal dose of microorganisms, (b) neutropenic mice receive a lethal dose of microorganisms or (c) rabbits receive an inoculum in the heart, and chronic infection models. The model selected will depend in part on the intended clinical indication of the analogue.

By way of example, in one such normal mouse model, mice are inoculated ip or iv with a lethal dose of bacteria. Typically, the dose is such that 90-100% of animals die within 2 days. The choice of a microrganismal strain for this assay depends, in part, upon the intended application of the analogue, and in the accompanying examples, assays are carried out with three different *Staphylococcus* strains. Briefly, shortly before or after inoculation (generally within 60 minutes), analogue in a suitable formulation buffer is injected. Multiple injections of analogue may be administered. Animals are observed for up to 8 days post-infection and the survival of animals is recorded. Successful treatment either rescues animals from death or delays death to a statistically significant level, as compared with non-treatment control animals. Analogues that show better efficacy than indolicidin itself are preferred.

In vivo toxicity of an analogue is measured through administration of a range of doses to animals, typically mice, by a route defined in part by the intended clinical use. The survival of the animals is recorded and $LD_{50}$, $LD_{90-100}$, and maximum tolerated dose (MTD) can be calculated to enable comparison of analogues. Analogues less toxic than indolicidin are preferred.

Additional in vivo assays may be performed to assist in the selection of analogues for clinical development. For example, immunogenicity of analogues can be evaluated, typically by injection of the analogue in formulation buffer into normal animals, generally mice, rats, or rabbits. At various times after injection, serum is obtained and tested for the presence of antibodies that bind to the analogue. Testing after multiple injections, mimicking treatment protocols, may also be performed. Antibodies to analogues can be identified by ELISA, immunoprecipitation assays, Western blots, and other methods. (see, Harlow and Lane, Antibodies: A Laboratory Manual, Cold Spring Harbor Laboratory Press, Cold Spring Harbor, N.Y., 1988). Analogues that elicit no or minimal production of antibodies are preferred. Additionally, pharmacokinetics of the analogues in animals and histopathology of animals treated with analogues may be determined.

Selection of indolicidin analogues as potential therapeutics is based on in vitro and in vivo assay results. In general, peptide analogues that exhibit low toxicity at high dose levels and high efficacy at low dose levels are preferred candidates.

3. Synergy Assays

For assessment of analogues in combination with an antibiotic or another analogue, the combination can be subjected to the above series of assays. Antibiotics include any chemical that tends to prevent, inhibit or destroy life and as such, antibiotics include anti-bacterial agents, anti-fungicides, anti-viral agents, and anti-parasitic agents. Merely by way of example, anti-bacterial antibiotics are discussed. Methods for mixing and administering the components vary depending on the intended clinical use of the combination.

Briefly, one assay for in vitro anti-bacterial activity, the agarose dilution assay, is set up with an array of plates that each contain a combination of peptide analogue and antibiotic in various concentrations. The plates are inoculated with bacterial isolates, incubated, and the MICs of the components recorded. These results are then used to calculate the FIC. Antibiotics used in testing include, but are not limited to, penicillins, cephalosporins, carbacephems, cephamycins, carbapenems, monobactams, aminoglycosides, glycopeptides, quinolones, tetracyclines, macrolides, and fluoroquinolones (see Table 1 below).

Examples of antibiotics, include, but are not limited to, Penicillin G (CAS Registry No.: 61-33-6); Methicillin (CAS Registry No.: 61-32-5); Nafcillin (CAS Registry No.: 147-52-4); Oxacillin (CAS Registry No.: 66-79-5); Cloxacillin (CAS Registry No.: 61-72-3); Dicloxacillin (CAS Registry No.: 3116-76-5); Ampicillin (CAS Registry No.: 69-53-4); Amoxicillin (CAS Registry No.: 26787-78-0); Ticarcillin (CAS Registry No.: 34787-01-4); Carbenicillin (CAS Registry No.: 4697-36-3); Mezlocillin (CAS Registry No.: 51481-

65-3); Azlocillin (CAS Registry No.: 37091-66-0); Piperacillin (CAS Registry No.: 61477-96-1); Imipenem (CAS Registry No.: 74431-23-5); Aztreonam (CAS Registry No.: 78110-38-0); Cephalothin (CAS Registry No.: 153-61-7); Cefazolin (CAS Registry No.: 25953-19-9); Cefaclor (CAS Registry No.: 70356-03-5); Cefamandole formate sodium (CAS Registry No.: 42540-40-9); Cefoxitin (CAS Registry No.: 35607-66-0); Cefuroxime (CAS Registry No.: 55268-75-2); Cefonicid (CAS Registry No.: 61270-58-4); Cefmetazole (CAS Registry No.: 56796-20-4); Cefotetan (CAS Registry No.: 69712-56-7); Cefprozil (CAS Registry No.: 92665-29-7); Loracarbef (CAS Registry No.: 121961-22-6); Cefetamet (CAS Registry No.: 65052-63-3); Cefoperazone (CAS Registry No.: 62893-19-0); Cefotaxime (CAS Registry No.: 63527-52-6); Ceftizoxime (CAS Registry No.: 68401-81-0); Ceftriaxone (CAS Registry No.: 73384-59-5); Ceftazidime (CAS Registry No.: 72558-82-8); Cefepime (CAS Registry No.: 88040-23-7); Cefixime (CAS Registry No.: 79350-37-1); Cefpodoxime (CAS Registry No.: 80210-62-4); Cefsulodin (CAS Registry No.: 62587-73-9); Fleroxacin (CAS Registry No.: 79660-72-3); Nalidixic acid (CAS Registry No.: 389-08-2); Norfloxacin (CAS Registry No.: 70458-96-7); Ciprofloxacin (CAS Registry No.: 85721-33-1); Ofloxacin (CAS Registry No.: 82419-36-1); Enoxacin (CAS Registry No.: 74011-58-8); Lomefloxacin (CAS Registry No.: 98079-51-7); Cinoxacin (CAS Registry No.: 28657-80-9); Doxycycline (CAS Registry No.: 564-25-0); Minocycline (CAS Registry No.: 10118-90-8); Tetracycline (CAS Registry No.: 60-54-8); Amikacin (CAS Registry No.: 37517-28-5); Gentamicin (CAS Registry No.: 1403-66-3); Kanamycin (CAS Registry No.: 8063-07-8); Netilmicin (CAS Registry No.: 56391-56-1); Tobramycin (CAS Registry No.: 32986-56-4); Streptomycin (CAS Registry No.: 57-92-1); Azithromycin (CAS Registry No.: 83905-01-5); Clarithromycin (CAS Registry No.: 81103-11-9); Erythromycin (CAS Registry No.: 114-07-8); Erythromycin estolate (CAS Registry No.: 3521-62-8); Erythromycin ethyl succinate (CAS Registry No.: 41342-53-4); Erythromycin glucoheptonate (CAS Registry No.: 23067-13-2); Erythromycin lactobionate (CAS Registry No.: 3847-29-8); Erythromycin stearate (CAS Registry No.: 643-22-1); Vancomycin (CAS Registry No.: 1404-90-6); Teicoplanin (CAS Registry No.: 61036-64-4); Chloramphenicol (CAS Registry No.: 56-75-7); Clindamycin (CAS Registry No.: 18323-44-9); Trimethoprim (CAS Registry No.: 738-70-5); Sulfamethoxazole (CAS Registry No.: 723-46-6); Nitrofurantoin (CAS Registry No.: 67-20-9); Rifampin (CAS Registry No.: 13292-46-1); Mupirocin (CAS Registry No.: 12650-69-0); Metronidazole (CAS Registry No.: 443-48-1); Cephalexin (CAS Registry No.: 15686-71-2); Roxithromycin (CAS Registry No.: 80214-83-1); Co-amoxiclavuanate; combinations of Piperacillin and Tazobactam; and their various salts, acids, bases, and other derivatives.

TABLE 1

| Class of Antibiotic | Antibiotic | Mode of Action |
| --- | --- | --- |
| PENICILLINS | | Blocks the formation of new cell walls in bacteria |
| Natural | Penicillin G, Benzylpenicillin Penicillin V, Phenoxymethylpenicillin | |
| Penicillinase resistant | Methicillin, Nafcillin, Oxacillin Cloxacillin, Dicloxacillin | |
| Acylamino-penicillins | Ampicillin, Amoxicillin | |
| Carboxy-penicillins | Ticarcillin, Carbenicillin | |
| Ureido-penicillins | Mezlocillin, Azlocillin, Piperacillin | |
| CARBAPENEMS | Imipenem, Meropenem | Blocks the formation of new cell walls in bacteria |
| MONOBACTAMS | | Blocks the formation of new cell walls in bacteria |
| | Aztreonam | |
| CEPHALOSPORINS | | Prevents formation of new cell walls in bacteria |
| 1st Generation | Cephalothin, Cefazolin | |
| 2nd Generation | Cefaclor, Cefamandole Cefuroxime, Cefonicid, Cefmetazole, Cefotetan, Cefprozil | |
| 3rd Generation | Cefetamet, Cefoperazone Cefotaxime, Ceftizoxime Ceftriaxone, Ceftazidime Cefixime, Cefpodoxime, Cefsulodin | |
| 4th Generation | Cefepime | |
| CARBACEPHEMS | Loracarbef | Prevents formation of new cell walls in bacteria |
| CEPHAMYCINS | Cefoxitin | Prevents formation of new cell walls in bacteria |
| QUINOLONES | Fleroxacin, Nalidixic Acid Norfloxacin, Ciprofloxacin Ofloxacin, Enoxacin Lomefloxacin, Cinoxacin | Inhibits bacterial DNA synthesis |
| TETRACYCLINES | Doxycycline, Minocycline, Tetracycline | Inhibits bacterial protein synthesis, binds to 30S ribosome subunit. |
| AMINOGLYCOSIDES | Amikacin, Gentamicin, Kanamycin, Netilmicin, Tobramycin, Streptomycin | Inhibits bacterial protein synthesis, binds to 30S ribosome subunit. |
| MACROLIDES | Azitbromycin, Clarithromycin, Erythromycin | inhibits bacterial protein synthesis, binds to 50S ribosome subunit |

TABLE 1-continued

| Class of Antibiotic | Antibiotic | Mode of Action |
| --- | --- | --- |
| Derivatives of Erythromycin | Erythromycin estolate, Erythromycin stearate<br>Erytbromycin ethylsuccinate<br>Erythromycin gluceptate<br>Erythromycin lactobionate | |
| GLYCOPEPTIDES | Vancomycin, Teicoplanin | Inhibits cell wall synthesis, prevents peptidoglycan elongation. |
| MISCELLANEOUS | Chloramphenicol | Inhibits bacterial protein synthesis, binds to 50S ribosome subunit. |
| | Clindamycin | Inhibits bacterial protein synthesis, binds to 50S ribosome subunit. |
| | Trimethoprim | Inhibits the enzyme dihydrofolate reductase, which activates folic acid. |
| | Sulfamethoxazole | Acts as antimetabolite of PABA & inhibits synthesis of folic acid |
| | Nitrofurantoin | Action unknown, but is concentrated in urine where it can act on urinary tract bacteria |
| | Rifampin | Inhibits bacterial RNA polymerase |
| | Mupirocin | Inhibits bacterial protein synthesis |

Synergy is calculated according to the formula below. An FIC of $\leq 0.5$ is evidence of synergy, although combinations with higher values may be therapeutically useful.

$$\frac{MIC(\text{peptide in combination})}{MIC(\text{peptide alone})} + \frac{MIC(\text{antibiotic in combination})}{MIC(\text{antibiotic alone})} = FIC$$

For example, antibiotics from the groups of penicillins, cephalosporins, carbacephems, cephamycins, carbapenems, monobactams, aminoglycosides, glycopeptides, quinolones, tetracyclines, macrolides, fluoroquinolones, and other miscellaneous antibiotics may be used in combination with any of the peptides disclosed herein. For example, MBI 11A1CN or MBI 11D18CN with Ciprofloxacin, MBI 11A1CN, MBI 11A3CN, MBI 11B4CN, MBI 11D18CN or MBI 11G13CN with Mupirocin, MBI 11B9CN, MBI 11D18CN or MBI 11F4CN with Piperacillin are preferred combinations.

C. Polymer Modification of Peptides and Proteins

As noted herein, the present invention provides methods and compositions for modifying a compound with a free amine group, such as peptides, proteins, certain antibiotics, and the like, with an activated polysorbate ester and derivatives. When the compounds are peptides or proteins, the modified or derivatized forms are referred to herein as "APS-modified peptides" or "APS-modified proteins". Similarly, modified forms of antibiotics are referred to as "APS-modified antibiotics." APS-modified compounds (e.g., APS-cationic peptides) have improved pharmacological properties.

In addition to peptides and proteins, antibiotics, antifungals, anti-rythmic drugs, and any other compound with a free primary or other amine are suitable for modification. For example, cephalosporins, aminopenicillins, ethambutol, pyrazinamide, sulfonamines, quinolones (e.g., ciprofiloxacin, clinafloxacin) aminoglycosides and spectinomhycins, including, but not limited to, streptomycin, neomycin, kanamycin, gentamicin, have free amines for modification. Antifungals such as amphotericin B, nystatin, 5-fluorocytosine, and the like have amines available for derivativization. Antivirals, such as tricyclic amines (e.g., amantadine); and antiparasitic agents (e.g.,dapsone), may all be derivatized. For exemplary purposes only, the discussion herein is directed to modified peptides and proteins.

1. Characteristics of Reagent

As discussed herein, a suitable reagent for formation of APS-modified compounds (e.g., peptides and proteins) comprises a hydrophobic region and a hydrophilic region, and optionally a linker. The hydrophobic region is a lipophilic compound with a suitable functional group for conjugation to the hydrophilic region or linker. The hydrophilic region is a polyalkylene glycol. As used herein, "polyalkylene glycol" refers to 2 or 3 carbon polymers of glycols. Two carbon polyalkylenes include polyethylene glycol (PEG) of various molecular weights, and its derivatives, such as polysorbate. Three carbon polyalkylenes include polypropylene glycol and its derivatives.

The hydrophobic region is generally a fatty acid, but may be a fatty alcohol, fatty thiol, and the like, which are also lipophilic compounds. The fatty acid may be saturated or unsaturated. The chain length does not appear to be important, although typically commercially available fatty acids are used and have chain lengths of $C_{12-18}$. The length may be limited however by solubility or solidity of the compound, that is longer lengths of fatty acids are solid at room temperature. Fatty acids of 12 carbons (lauryl), 14 carbons, 16 carbons (palmitate), and 18 carbons (monostearate or oleate) are preferred chain lengths.

The hydrophilic region is a polyalkylene glycol, either polyethylene or polypropylene glycol monoether. The ether function is formed by the linkage between the polyoxyethylene chain, preferably having a chain length of from 2 to 100 monomeric units, and the sorbitan group. Polymethylene glycol is unsuitable for administration in animals due to formation of formaldehydes, and glycols with a chain length of ≧4 may be insoluble. Mixed polyoxyethylene-polyoxypropylene chains are also suitable.

A linker for bridging the hydrophilic and hydrophobic regions is not required, but if used, should be a bifunctional nucleophile able to react with both polyalkylene glycol and the hydrophobic region. The linker provides electrons for a nucleophilic reaction with the polyalkylene glycol, typically formed by reaction with ethylene oxide or propylene oxide. Suitable linkers include sorbitan, sugar alcohols, ethanolamine, ethanolthiol, 2-mercaptoethanol, 1,6 diaminohexane, an amino acid (e.g., glutamine, lysine), other reduced sugars, and the like. For example, sorbitan forms an ester linkage with the fatty acid in a polysorbate.

Suitable compounds include polyoxyethylenesorbitans, such as the monolaurate, monooleate, monopalmitate, monostearate, trioleate, and tristearate esters. These and other suitable compounds may be synthesized by standard chemical methods or obtained commercially (e.g., Sigma Chemical Co., MO; Aldrich Chemical Co., WI; J. B. Baker, N.J.).

2. Activation of Reagent

The reagent, generally a polysorbate, is activated by exposure to UV light with free exchange of air. Activation is achieved using a lamp that irradiates at 254 nm or 302 nm. Preferably, the output is centered at 254 nm. Longer wave lengths may require longer activation time. While some evidence exists that fluorescent room light can activate the polysorbates, experiments have shown that use of UV light at 254 nm yields maximal activation before room light yields a detectable level of activation.

Air plays an important role in the activation of the polysorbates. Access to air doubles the rate of activation relative to activations performed in sealed containers. It is not yet known which gas is responsible; an oxygen derivative is likely, although peroxides are not involved. UV exposure of compounds with ether linkages is known to generate peroxides, which can be detected and quantified using peroxide test strips. In a reaction, hydrogen peroxide at 1 to 10 fold higher level than found in UV-activated material was added to a polysorbate solution in the absence of light. No activation was obtained.

The reagent is placed in a suitable vessel for irradiation. A consideration for the vessel is the ability to achieve uniform irradiation. Thus, if the pathlength is long, the reagent may be mixed or agitated. The activation requires air; peroxides are not involved in the activation. The reagent can be activated in any aqueous solution and buffering is not required.

An exemplary activation takes place in a cuvette with a 1 cm liquid thickness. The reagent is irradiated at a distance of less than 9 cm at 1500 $\mu W/cm^2$ (initial source output) for approximately 24 hours. Under these conditions, the activated reagent converts a minimum of 85% of the peptide to APS-peptide.

3. Modification of Peptides or Proteins with Activated Reagent

The peptides or proteins are reacted with the APS reagent in either a liquid or solid phase and become modified by the attachment of the APS derivative. The methods described herein for attachment offer the advantage of maintaining the charge on the peptide or protein. When the charge of the peptide is critical to its function, such as the antibiotic activity of cationic peptides described herein, these attachment methods offer additional advantages. Methods that attach groups via acylation result in the loss of positive charge via conversion of amino to amido groups. In addition, no bulky or potentially antigenic linker, such as a triazine group, is known to be introduced by the methods described herein.

As noted above, APS-peptide formation occurs in solid phase or in aqueous solution. Briefly, in the solid phase method, the peptide is suspended in a suitable buffer, such as an acetate buffer. Other suitable buffers that support APS-peptide formation may also be used. The acetate buffer may be sodium, rubidium, lithium, and the like. Other acetate solutions, such as HAc or HAc-NaOH, are also suitable. A preferred pH range for the buffer is from 2 to 8.3, although a wider range may be used. When the starting pH of the acetic acid-NaOH buffer is varied, subsequent lyophilization from 200 mM acetic acid buffer yields only the Type I modified peptide (see Example 14). The presence of an alkaline buffer component results in the formation of Type II modified peptides. A typical peptide concentration is 1 mg/ml, which results in 85-95% modified peptide, however other concentrations are suitable. The major consideration for determining concentration appears to be economic. The activated polymer (APS) is added in molar excess to the peptide, such that a 1:1 molar ratio of APS-modified peptide is generated. Generally, a starting ratio of approximately 2.5:1 (APS:peptide) to 5:1 (APS: peptide) yields a 1:1 APS-modified peptide.

The reaction mix is then frozen (e.g., −80° C.) and lyophilized. Sodium acetate disproportionates into acetic acid and NaOH during lyophilization; removal of the volatile acetic acid by the vacuum leaves NaOH dispersed throughout the result solid matrix. This loss of acetic acid is confirmed by a pH increase detected upon dissolution of the lyophilizate. No APS-modified peptide is formed in acetate buffer if the samples are only frozen then thawed.

The modification reaction can also take place in aqueous solution. However, APS modifications do not occur at ambient temperature in any acetate buffer system tested regardless of pH. APS modifications also are not formed in phosphate buffers as high as pH 11.5. APS modification does occur in a sodium carbonate buffer at a pH greater than about 8.5. Other buffers may also be used if they support derivitization. A pH range of 9-11 is also suitable, and pH 10 is most commonly used. The reaction occurs in two phases: Type I peptides form first, followed by formation of Type II peptides.

In the present invention, linkage occurs at an amino group. For a peptide, linkage can occur at the $\alpha\text{-NH}_2$ of the N-terminal amino acid or $\epsilon\text{-NH}_2$ group of lysine. Other primary and secondary amines may also be modified. Complete blocking of all amino groups by acylation (MBI 11CN-Y1) inhibits APS-peptide formation. Thus, modification of arginine or tryptophan residues does not occur. If the only amino group available is the α-amino group (e.g., MBI 11B9CN and MBI 11G14CN), the Type I form is observed. The inclusion of a single lysine (e.g., MBI 11B1CN, MBI 11B7CN, MBI 11B8CN), providing an ε-amino group, results in Type II forms as well. The amount of Type II formed increases for peptides with more lysine residues.

4. Purification and Physical Properties of APS-modified Peptides

The APS-modified peptides may be purified. In circumstances in which the free peptide is toxic, purification may be necessary to remove unmodified peptide and/or unreacted polysorbate. Any of a variety of purification methods may be used. Such methods include reversed phase HPLC, precipitation by organic solvent to remove polysorbate, size exclusion chromatography, ion exchange chromatography, filtration and the like. RP-HPLC is preferred. Procedures for these separation methods are well known.

APS-peptide (or protein) formation results in the generation of peptide-containing products that are more hydrophobic that the parent peptide. This property can be exploited to effect separation of the conjugate from free peptide by RP- HPLC. The conjugates are resolved into two populations based on their hydrophobicity as determined by RP-HPLC; the Type I population elutes slightly earlier than the Type II population.

The MBI 11 series of peptides have molecular weights between 1600 and 2500. When run on a Superose 12 column, a size exclusion column, these peptides elute no earlier than the bed volume indicating a molecular mass below 20 kDa. In contrast, the APS-modified peptides elute at 50 kDa, thus demonstrating a large increase in apparent molecular mass.

An increase in apparent molecular mass could enhance the pharmacokinetics of the cationic peptides because increased molecular mass reduces the rate at which peptides and proteins are removed from blood. Micelle formation may offer additional benefits by delivering "packets" of peptide molecules to microorganisms rather than relying on the multiple binding of single peptide molecules. In addition, the APS-modified peptides are soluble in methylene chloride or chloroform, whereas the parent peptide is essentially insoluble. This increased organic solubility may significantly enhance the ability to penetrate tissue barriers.

In addition, by circular dichroism (CD) studies, APS-modified peptides are observed to have an altered 3-dimensional conformation. As shown in the Examples, MBI 11CN and MBI 11B7CN have unordered structures in phosphate buffer or 40% aqueous trifluoroethanol (TFE) and form a β-turn conformation only upon insertion into liposomes. In contrast, CD spectra for APS-modified MBI 11CN and APS-modified MBI 11B7CN indicate β-turn structure in phosphate buffer.

D. Formulations and Administration

As noted above, the present invention provides methods for treating and preventing infections by administering to a patient a therapeutically effective amount of a peptide analogue of indolicidin as described herein. Patients suitable for such treatment may be identified by well-established hallmarks of an infection, such as fever, pus, culture of organisms, and the like. Infections that may be treated with peptide analogues include those caused by or due to microorganisms. Examples of microorganisms include bacteria (e.g., Gram-positive, Gram-negative), fungi, (e.g., yeast and molds), parasites (e.g., protozoans, nematodes, cestodes and trematodes), viruses, and prions. Specific organisms in these classes are well known (see for example, Davis et al., *Microbiology*, 3$^{rd}$ edition, Harper & Row, 1980). Infections include, but are not limited to, toxic shock syndrome, diphtheria, cholera, typhus, meningitis, whooping cough, botulism, tetanus, pyogenic infections, dysentery, gastroenteritis, anthrax, Lyme disease, syphilis, rubella, septicemia and plague.

Effective treatment of infection may be examined in several different ways. The patient may exhibit reduced fever, reduced number of organisms, lower level of inflammatory molecules (e.g., IFN-γ, IL-12, IL-1, TNF), and the like.

Peptide analogues of the present invention are preferably administered as a pharmaceutical composition. Briefly, pharmaceutical compositions of the present invention may comprise one or more of the peptide analogues described herein, in combination with one or more physiologically acceptable carriers, diluents, or excipients. As noted herein, the formulation buffer used may affect the efficacy or activity of the peptide analogue. A suitable formulation buffer contains buffer and solubilizer. The formulation buffer may comprise buffers such as sodium acetate, sodium citrate, neutral buffered saline, phosphate-buffered saline, and the like or salts, such as NaCl. Sodium acetate is preferred. In general, an acetate buffer from 5 to 500 mM is used, and preferably from 100 to 200 mM. The pH of the final formulation may range from 3 to 10, and is preferably approximately neutral (about pH 7-8). Solubilizers, such as polyoxyethylenesorbitans (e.g., Tween 80, Tween 20) and polyoxyethylene ethers (e.g., Brij 56) may also be added if the compound is not already APS-modified.

Although the formulation buffer is exemplified herein with peptide analogues of the present invention, this buffer is generally useful and desirable for delivery of other peptides. Peptides that may be delivered in this formulation buffer include indolicidin, other indolicidin analogues (see, PCT WO 95/22338), bacteriocins, gramicidin, bactenecin, drosocin, polyphemusins, defensins, cecropins, melittins, cecropin/melittin hybrids, magainins, sapecins, apidaecins, protegrins, tachyplesins, thionins; IL-1 through 15; corticotropin-releasing hormone; human growth hormone; insulin; erythropoietin; thrombopoietin; myelin basic protein peptides; various colony stimulating factors such as M-CSF, GM-CSF, kit ligand; and peptides and analogues of these and similar proteins.

Additional compounds may be included in the compositions. These include, for example, carbohydrates such as glucose, mannose, sucrose or dextrose, mannitol, other proteins, polypeptides or amino acids, chelating agents such as EDTA or glutathione, adjuvants and preservatives. As noted herein, pharmaceutical compositions of the present invention may also contain one or more additional active ingredients, such as an antibiotic (see discussion herein on synergy) or cytokine.

The compositions may be administered in a delivery vehicle. For example, the composition can be encapsulated in a liposome (see, e.g., WO 96/10585; WO 95/35094), complexed with lipids, encapsulated in slow-release or sustained release vehicles, such as poly-galactide, and the like. Within other embodiments, compositions may be prepared as a lyophilizate, utilizing appropriate excipients to provide stability.

Pharmaceutical compositions of the present invention may be administered in various manners. For example, peptide analogues may be administered by intravenous injection, intraperitoneal injection or implantation, subcutaneous injection or implantation, intradermal injection, lavage, inhalation, implantation, intramuscular injection or implantation, intrathecal injection, bladder wash-out, suppositories, pessaries, topical (e.g., creams, ointments, skin patches, eye drops, ear drops, shampoos) application, enteric, oral, or nasal route. The analogue may be applied locally as an injection, drops, spray, tablets, cream, ointment, gel, and the like. Analogue may be administered as a bolus or as multiple doses over a period of time.

The level of peptide in serum and other tissues after administration can be monitored by various well-established techniques such as bacterial, chromatographic or antibody based, such as ELISA, assays.

Pharmaceutical compositions of the present invention are administered in a manner appropriate to the infection or disease to be treated. The amount and frequency of administration will be determined by factors such as the condition of the patient, the cause of the infection, and the severity of the infection. Appropriate dosages may be determined by clinical trials, but will generally range from about 0.1 to 50 mg/kg.

In addition, the analogues of the present invention may be used in the manner of common disinfectants or in any situation in which microorganisms are undesirable. For example, these peptides may be used as surface disinfectants, coatings, including covalent bonding, for medical devices, coatings for clothing, such as to inhibit growth of bacteria or repel mosquitoes, in filters for air purification, such as on an airplane, in water purification, constituents of shampoos and soaps, food preservatives, cosmetic preservatives, media preservatives, herbicide or insecticides, constituents of building materials, such as in silicone sealant, and in animal product processing, such as curing of animal hides. As used herein, "medical device" refers to any device for use in a patient, such as an implant or prosthesis. Such devices include, stents, tubing, probes, cannulas, catheters, synthetic vascular grafts, blood monitoring devices, artificial heart valves, needles, and the like.

For these purposes, typically the peptides alone or in conjunction with an antibiotic are included in compositions commonly employed or in a suitable applicator, such as for applying to clothing. They may be incorporated or impregnated into the material during manufacture, such as for an air filter, or otherwise applied to devices. The peptides and antibiotics need only be suspended in a solution appropriate for the device or article. Polymers are one type of carrier that can be used.

The analogues, especially the labeled analogues, may be used in image analysis and diagnostic assays or for targeting sites in eukaryotic multicellular and single cell cellular organisms and in prokaryotes. As a targeting system, the analogues may be coupled with other peptides, proteins, nucleic acids, antibodies and the like.

The following examples are offered by way of illustration, and not by way of limitation.

EXAMPLES

Example 1

Synthesis Purification and Characterization of Peptide Analogues

Peptide synthesis is based on the standard solid-phase Fmoc protection strategy. The instrument employed is a 9050 Plus PepSynthesiser (PerSeptive BioSystems Inc.). Polyethylene glycol polystyrene (PEG-PS) graft resins are employed as the solid phase, derivatized with an Fmoc-protected amino acid linker for C-terminal amide synthesis. HATU (O-(7-azabenzotriazole-1-yl)-1,1,3,3-tetramethyluronium hexafluorophosphate) is used as the coupling reagent. During synthesis, coupling steps are continuously monitored to ensure that each amino acid is incorporated in high yield. The peptide is cleaved from the solid-phase resin using trifluoroacetic acid and appropriate scavengers and the crude peptide is purified using preparative reversed-phase chromatography.

All peptides are analyzed by mass spectrometry to ensure that the product has the expected molecular mass. The product should have a single peak accounting for >95% of the total peak area when subjected to analytical reversed-phase high performance liquid chromatography (RP-HPLC). In addition, the peptide should show a single band accounting for >90% of the total band intensity when subjected to acid-urea gel electrophoresis.

Peptide content, the amount of the product that is peptide rather than retained water, salt or solvent, is measured by quantitative amino acid analysis, free amine derivatization or spectrophotometric quantitation. Amino acid analysis also provides information on the ratio of amino acids present in the peptide, which assists in confirming the authenticity of the peptide.

Peptide analogues and their names are listed in Table 2. In this table, and elsewhere, the amino acids are denoted by the one-letter amino acid code and lower case letters represent the D-form of the amino acid.

TABLE 2

| | | |
|---|---|---|
| 10 | (SEQ ID NO: 29) | I L P W K W P W W P W R R |
| 10CN | (SEQ ID NO: 29) | I L P W K W P W W P W R R |
| 11 | (SEQ ID NO: 30) | I L K K W P W W P W R R K |
| 11CN | (SEQ ID NO: 30) | I L K K W P W W P W R R K |
| 11CNR | (SEQ ID NO: 31) | K R R W P W W P W K K L I |
| 11A1CN | (SEQ ID NO: 22) | I L K K F P F F P F R R K |
| 11A2CN | (SEQ ID NO: 32) | I L K K I P I I P I R R K |
| 11A3CN | (SEQ ID NO: 23) | I L K K Y P Y Y P Y R R K |
| 11A4CN | (SEQ ID NO: 33) | I L K K W P W P W R R K |
| 11A5CN | (SEQ ID NO: 34) | I L K K Y P W Y P W R R K |
| 11A6CN | (SEQ ID NO: 35) | I L K K F P W F P W R R K |
| 11A7CN | (SEQ ID NO: 36) | I L K K F P F W P W R R K |
| 11ABCN | (SEQ ID NO: 37) | I L R Y V Y Y V Y R R K |
| 11B1CN | (SEQ ID NO: 38) | I L R R W P W W P W R R K |
| 11B2CN | (SEQ ID NO: 39) | I L R R W P W W P W R K |
| 11B3CN | (SEQ ID NO: 40) | I L K W P W W P W R R K |
| 11B4CN | (SEQ ID NO: 24) | I L K K W P W W P W R K |
| 11B5CN | (SEQ ID NO: 41) | I L K W P W W P W R K |
| 11B7CN | (SEQ ID NO: 42) | I L R W P W W P W R R K |
| 11B7CNR | (SEQ ID NO: 43) | K R R W P W W P W R L I |
| 11B8CN | (SEQ ID NO: 44) | I L W P W W P W R R K |

TABLE 2-continued

```
11B9CN    (SEQ ID NO: 25)  I L R R W P W W P W R R R
11B10CN   (SEQ ID NO: 45)  I L K K W P W W P W K K K
11B16CN   (SEQ ID NO: 46)  I L R W P W W P W R R K I M I L K K A G S
11B17CN   (SEQ ID NO: 47)  I L R W P W W P W R R K M I L K K A G S
11B18CN   (SEQ ID NO: 48)  I L R W P W W P W R R K D M I L K K A G S
11C3CN    (SEQ ID NO: 49)  I L K K W A W W P W R R K
11C4CN    (SEQ ID NO: 50)  I L K K W P W W A W R R K
11C5CN    (SEQ ID NO: 51)  W W K K W P W W P W R R K
11D1CN    (SEQ ID NO: 52)  L K K W P W W P W R R K
11D3CN    (SEQ ID NO: 53)  P W W P W R R K
11D4CN    (SEQ ID NO: 54)  I L K K W P W W P W R R K M I L K K A G S
11D5CN    (SEQ ID NO: 55)  I L K K W P W W P W R R M I L K K A G S
11D6CN    (SEQ ID NO: 56)  I L K K W P W W P W R R I M I L K K A G S
11D11H    (SEQ ID NO: 57)  I L K K W P W W P W R R K M
11D12H    (SEQ ID NO: 58)  I L K K W P W W P W R R M
11D13H    (SEQ ID NO: 59)  I L K K W P W W P W R R I M
11D14CN   (SEQ ID NO: 60)  I L K K W W W P W R K
11D15CN   (SEQ ID NO: 61)  I L K K W P W W W R K
11D18CN   (SEQ ID NO: 26)  W R I W K P K W R L P K W
11E1CN    (SEQ ID NO: 62)  I L K K W P W W P W R R K
11E2CN    (SEQ ID NO: 63)  I L K K W P W W P W R R k
11E3CN    (SEQ ID NO: 64)  I L K K W P W W P W R R k
11F1CN    (SEQ ID NO: 65)  I L K K W V W W V W R R K
11F2CN    (SEQ ID NO: 66)  I L K K W P W W V W R R K
11F3CN    (SEQ ID NO: 67)  I L K K W V W W P W R R K
11F4CN    (SEQ ID NO: 27)  I L R W V W W V W R R K
11F4CNR   (SEQ ID NO: 68)  K R R W V W W V W R L I
11G2CN    (SEQ ID NO: 69)  I K K W P W W P W R R K
11G3CN    (SEQ ID NO: 70)  I L K K P W W P W R R K
11G4CN    (SEQ ID NO: 71)  I L K K W W W P W R R K
11G5CN    (SEQ ID NO: 72)  I L K K W P W W W R R K
11G6CN    (SEQ ID NO: 73)  I L K K W P W W P R R K
11G7CN    (SEQ ID NO: 74)  I L K K W P W W P W R R
11G13CN   (SEQ ID NO: 28)  I L K K W P W W P W K
11G14CN   (SEQ ID NO: 75)  I L K K W P W W P W R
11H1CN    (SEQ ID NO: 76)  A L R W P W W P W R P K
11H2CN    (SEQ ID NO: 77)  I A R W P W W P W R R K
11H3CN    (SEQ ID NO: 78)  I L A W P W W P W R R K
11H4CN    (SEQ ID NO: 79)  I L R A P W W P W R R K
```

TABLE 2-continued

| | | |
|---|---|---|
| 11H5CN | (SEQ ID NO: 80) | I L R W A W W P W R R K |
| 11H6CN | (SEQ ID NO: 81) | I L R W P A W P W R R K |
| 11H7CN | (SEQ ID NO: 82) | I L R W P W A P W R R K |
| 11H8CN | (SEQ ID NO: 83) | I L R W P W W A W R R K |
| 11H9CN | (SEQ ID NO: 84) | I L R W P W W P A R R K |
| 11H10CN | (SEQ ID NO: 85) | I L R W P W W P W A R K |
| 11H11CN | (SEQ ID NO: 86) | I L R W P W W P W R A K |
| 11H12CN | (SEQ ID NO: 87) | I L R W P W W P W R R A |

CN suffix = amidated C-terminus
H suffix = humoserine at C-terminus
R suffix = retro-synthesized peptide Example 2

Synthesis of Modified Peptides

Indolicidin analogues are modified to alter the physical properties of the original peptide. Such modifications include: acetylation at the N-terminus, Fmoc-derivatized N-terminus, polymethylation, peracetylation, and branched derivatives.

α-N-terminal acetylation. Prior to cleaving the peptide from the resin and deptrotecting it, the fully protected peptide is treated with N-acetylimidazole in DMF for 1 hour at room temperature, which results in selective reaction at the α-N-terminus. The peptide is then deprotected/cleaved and purified as for an unmodified peptide.

Fmoc-derivatized α-N-terminus. If the final Fmoc deprotection step is not carried, the α-N-terminus Fmoc group remains on the peptide. The peptide is then side-chain deprotected/cleaved and purified as for an unmodified peptide.

Polymethylation. The purified peptide in a methanol solution is treated with excess sodium bicarbonate, followed by excess methyl iodide. The reaction mixture is stirred overnight at room temperature, extracted with organic solvent, neutralized and purified as for an unmodified peptide. Using this procedure, a peptide is not fully methylated; methylation of MBI 11CN yielded an average of 6 methyl groups. Thus, the modified peptide is a mixture of methylated products.

Peracetylation. A purified peptide in DMF solution is treated with N-acetylimidazole for 1 hour at room temperature. The crude product is concentrated, dissolved in water, lyophilized, re-dissolved in water and purified as for an unmodified peptide. Complete acetylation of primary amine groups is observed.

Four/eight branch derivatives. The branched peptides are synthesized on a four or eight branched core bound to the resin. Synthesis and deprotection/cleavage proceed as for an unmodified peptide. These peptides are purified by dialysis against 4 M guanidine hydrochloride then water, and analyzed by mass spectrometry.

Peptides modified using the above procedures are listed in Table 3.

TABLE 3

| Peptide modified | Peptide name | Sequence | Modification |
|---|---|---|---|
| 10 | 10A | I L P W K W P W P W R R (SEQ ID NO: 29) | Acetylated α-N-terminus |
| 11 | 11 | I L K K W P W W P W R R K (SEQ ID NO: 30) | Acetylated α-N-terminus |
| 11CN | 11CAN | I L K K W P W W P W R R K (SEQ ID NO: 30) | Acetylated α-N-terminus |
| 11CN | 11CNW1 | I L K K W P W W P W R R K (SEQ ID NO: 30) | Fmoc-derivatized N-terminus |
| 11CN | 11CNX1 | I L K K W P W W P W R R K (SEQ ID NO: 30) | Polymethylated derivative |
| 11CN | 11CNY1 | I L K K W P W W P W R P K (SEQ ID NO: 30) | Peracetylated derivative |
| 11 | 11M4 | I L K K W P W W P W R R K (SEQ ID NO: 30) | Four branch derivative |
| 11 | 11M8 | I L K K W P W W P W R R K (SEQ ID NO: 30) | Eight branch derivative |

TABLE 3-continued

| Peptide modified | Peptide name | Sequence | Modification |
|---|---|---|---|
| 11B1CN | 11B1CNW1 | I L R R W P W W P W R R K (SEQ ID NO: 38) | Fmoc-derivatized N-terminus |
| 11B4CN | 11B4ACN | I L K K W P W W P W R K (SEQ ID NO: 24) | Acetylated N-terminus |
| 11B9CN | 11B9ACN | I L R R W P W W P W R R R (SEQ ID NO: 25) | Acetylated N-terminus |
| 11D9 | 11D9M8 | W W P W R R K (SEQ ID NO: 88) | Eight branch derivative |
| 11D10 | 11D10M8 | I L K K W P W (SEQ ID NO: 89) | Eight branch derivative |
| 11G6CN | 11G6ACN | I L K K W P W W P R P K (SEQ ID NO: 73) | Acetylated α-N-terminus |
| 11G7CN | 11G7ACN | I L K K W P W W P W R R (SEQ ID NO: 74) | Acetylated α-N-terminus |

Example 3

Recombinant Production of Peptide Analogues

Peptide analogues are alternatively produced by recombinant DNA technique in bacterial host cells. The peptide is produced as a fusion protein, chosen to assist in transporting the fusion peptide to inclusion bodies, periplasm, outer membrane or extracellular environment.

Construction of Plasmids Encoding MBI-11 Peptide Fusion Protein

Amplification by polymerase chain reaction is used to synthesize double-stranded DNA encoding the MBI peptide genes from single-stranded templates. For MBI-11, 100 µl of reaction mix is prepared containing 50 to 100 ng of template, 25 pmole of each primer, 1.5 mM MgCl$_2$, 200 µM of each dNTP, 2U of Taq polymerase in the supplier's buffer. The reactions proceeded with 25 cycles of 94° C. for 30 sec., 55° C. for 30 sec., 74° C. for 30 sec., followed by 74° C. for 1 min. Amplified product is digested with BamHI and HindIII and cloned into a plasmid expression vector encoding the fusion partner and a suitable selection marker.

Production of MBI-11 Peptide Fusion in *E. coli*

The plasmid pR2h-11, employing a T7 promoter, high copy origin of replication, Ap$^r$ marker and containing the gene of the fusion protein, is co-electroporated with pGP1-2 into *E. coli* strain XL1-Blue. Plasmid pGP1-2 contains a T7 RNA polymerase gene under control of a lambda promoter and cI857 repressor gene. Fusion protein expression is induced by a temperature shift from 30° C. to 42° C. Inclusion bodies are washed with solution containing solubilizer and extracted with organic extraction solvent. Profiles of the samples are analyzed by SDS-PAGE. FIG. 1 shows the SDS-PAGE analysis and an extraction profile of inclusion body from whole cell. The major contaminant in the organic solvent extracted material is β-lactamase (FIG. 1). The expression level in these cells is presented in Table 4.

TABLE 4

| Fusion protein | Mol.mass (kDa) | % protein in whole cell lysate | % in inclusion body extract | % which is MBI-11 peptide |
|---|---|---|---|---|
| MBI-11 | 20.1 | 15 | 42 | 7.2 |

Figure 2:
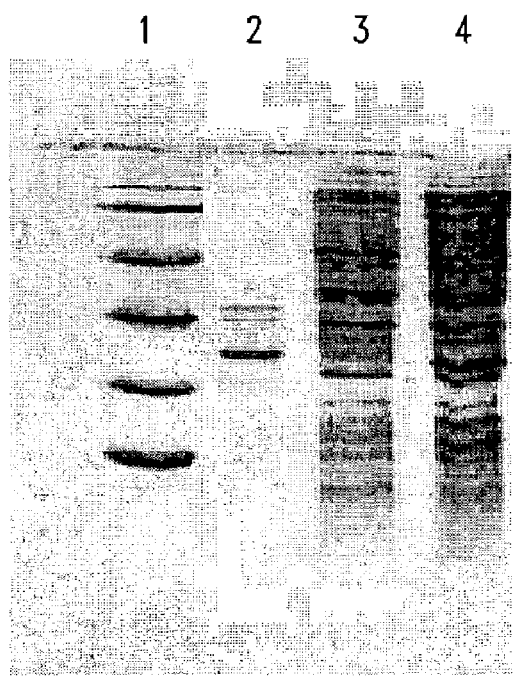
FIG. 2 is an SDS-PAGE showing the expression profile of the MBI-11 fusion protein using plasmid pPDR2h-11. Lane 1, protein standards; lane 2, organic solvent extracted MBI-11; lane 3, total lysate of XL1 Blue (pPDR2h-11, pGP1-2), cultured at 30° C.; lane 4, total lysate of XL1 Blue (pPDR2h-11, pGP1-2), induced at 42° C.

In addition, a low-copy-number vector, pPD100, which contains a chloramphenicol resistance gene, is used to express MBI-11 in order to eliminate the need for using ampicillin, thereby reducing the appearance of β-lactamase in extracted material. This plasmid allows selective gene expression and high-level protein overproduction in *E. coli* using the bacteriophage T7 RNA polymerase/T7 promoter system (Dersch et al., *FEMS Microbiol. Lett.* 123: 19-26, 1994). pPD100 contains a chloramphenicol resistance gene (CAT) as a selective marker, a multiple cloning site, and an ori sequence derived from the low-copy-number vector pSC101. There are only about 4 to 6 copies of these plasmids per host cell. The resulting construct containing MBI-11 is called pPDR2h-11. FIG. 2 presents a gel electrophoresis analysis of the MBI-11 fusion protein expressed in this vector. Expression level of MBI-11 fusion protein is comparable with that obtained from plasmid pR2h-11. The CAT gene product is not apparent, presumably due to the low-copy-number nature of this plasmid, CAT protein is not expressed at high levels in pPDR2h-11.

Example 4

In vitro Assays to Measure Peptide Analogue Activity

Agarose Dilution Assay

The agarose dilution assay measures antimicrobial activity of peptides and peptide analogues, which is expressed as the minimum inhibitory concentration (MIC) of the peptides.

In order to mimic in vivo conditions, calcium and magnesium supplemented Mueller Hinton broth is used in combination with a low EEO agarose as the bacterial growth medium. The more commonly used agar is replaced with agarose as the charged groups in agar prevent peptide diffusion through the media. The media is autoclaved and then cooled to 50-55° C. in a water bath before aseptic addition of antimicrobial solutions. The same volume of different concentrations of peptide solution are added to the cooled molten agarose that is then poured to a depth of 3-4 mm.

The bacterial inoculum is adjusted to a 0.5 McFarland turbidity standard (PML Microbiological) and then diluted 1:10 before application on to the agarose plate. The final inoculum applied to the agarose is approximately $10^4$ CFU in a 5-8 mm diameter spot. The agarose plates are incubated at 35-37° C. for 16 to 20 hours.

The MIC is recorded as the lowest concentration of peptide that completely inhibits growth of the organism as determined by visual inspection. Representative MICs for various indolicidin analogues are shown in the Table 5 below.

TABLE 5

| Organism | Organism # | MIC (µg/ml) |
|---|---|---|
| 1. MBI 10 | | |
| A. calcoaceticus | AC001 | 128 |
| E. coli | ECO002 | 128 |
| E. faecalis | EFS004 | 8 |
| K. pneumoniae | KP001 | 128 |
| P. aeruginosa | PA003 | >128 |
| S. aureus | SA007 | 2 |
| S. maltophilia | SMA001 | 128 |
| S. marcescens | SMS003 | >128 |
| 2. MBI 10A | | |
| E. faecalis | EFS004 | 16 |
| E. faecium | EFM003 | 8 |
| S. aureus | SA010 | 8 |
| 3. MBI 10CN | | |
| A. calcoaceticus | AC001 | 64 |
| E. cloacae | ECL007 | >128 |
| E. coli | ECO001 | 32 |
| E. coli | SBECO2 | 16 |
| E. faecalis | EFS004 | 8 |
| E. faecium | EFM003 | 2 |
| K. pneumoniae | KP002 | 64 |
| P. aeruginosa | PA002 | >128 |
| S. aureus | SA003 | 2 |
| S. epiderimidis | SE010 | 4 |
| S. maltophilia | SMA002 | 64 |
| S. marcescens | SMS004 | >128 |
| 4. MBI 11 | | |
| A. calcoaceticus | AC002 | 8 |
| E. cloacae | ECL007 | >128 |
| E. coli | ECO002 | 64 |
| E. faecium | EFM003 | 4 |
| E. faecalis | EFS002 | 64 |
| K. pneumoniae | KP001 | 128 |
| P. aeruginosa | PA004 | >128 |
| S. aureus | SA004 | 4 |
| S. maltophilia | SMA002 | 128 |
| S. marcescens | SMS004 | >128 |
| 5. MBI 11A | | |
| A. calcoaceticus | AC001 | >64 |
| E. cloacae | ECL007 | >64 |
| E. coli | ECO005 | >64 |
| E. faecalis | EFS004 | 32 |
| K. pneumoniae | KP001 | 64 |
| P. aeruginosa | PA024 | >64 |
| S. aureus | SA002 | 4 |
| S. maltophilia | SMA002 | >64 |
| S. marcescens | SMS003 | >64 |
| 6. MBI 11ACN | | |
| A. calcoaceticus | AC002 | 2 |
| E. cloacae | ECL007 | >128 |
| E. coli | ECO005 | 16 |
| E. faecalis | EFS004 | 8 |
| E. faecalis | EFS008 | 64 |
| K. pneumoniae | KP001 | 16 |
| P. aeruginosa | PA004 | >128 |
| S. aureus | SA014 | 8 |
| S. epidermidis | SE010 | 4 |
| S. maltophilia | SMA002 | 64 |
| S. marcescens | SMS003 | >128 |
| 7. MBI 11CN | | |
| A. calcoaceticus | AC001 | 128 |
| E. cloacae | ECL007 | >64 |
| E. coli | ECO002 | 8 |
| E. faecium | EFM001 | 8 |
| E. faecalis | EFS001 | 32 |
| H. influenzae | HIN001 | >128 |
| K. pneumoniae | KP002 | 128 |
| P. aeruginosa | PA003 | >128 |
| P. mirabilis | PM002 | >128 |
| S. aureus | SA003 | 2 |
| S. marcescens | SBSM1 | >128 |
| S. pneumoniae | SBSPN2 | >128 |
| S. epidermidis | SE001 | 2 |
| S. maltophilia | SMA001 | 64 |
| S. marcescens | SMS003 | >128 |
| S. pyogenes | SPY003 | 8 |
| 8. MBI 11CNR | | |
| A. calcoaceticus | AC002 | 4 |
| E. cloacae | ECL007 | >128 |
| E. coli | ECO005 | 8 |
| E. faecalis | EFS001 | 4 |
| K. pneumoniae | KP001 | 4 |
| P. aeruginosa | PA004 | 32 |
| S. aureus | SA093 | 4 |
| S. epidermidis | SE010 | 4 |
| S. maltophilia | SMA002 | 32 |
| S. marcescens | SMS003 | 128 |
| 9. MBI 11CNW1 | | |
| A. calcoaceticus | AC002 | 8 |
| E. cloacae | ECL007 | 64 |
| E. coli | ECO005 | 32 |
| E. faecalis | EFS001 | 8 |
| K. pneumoniae | KP001 | 32 |
| P. aeruginosa | PA004 | 64 |
| S. aureus | SA010 | 4 |
| S. maltophilia | SMA002 | 32 |
| S. marcescens | SMS003 | >128 |
| 10. MBI 11CNX1 | | |
| A. calcoaceticus | AC001 | >64 |
| E. cloacae | ECL007 | >64 |
| E. coli | ECO005 | 64 |
| E. faecalis | EFS004 | 16 |
| K. pneumoniae | KP001 | >64 |
| P. aeruginosa | PA024 | >64 |
| S. aureus | SA006 | 2 |
| S. maltophilia | SMA002 | >64 |
| S. marcescens | SMS003 | >64 |
| 11. MBI 11CNY1 | | |
| A. calcoaceticus | AC001 | >64 |
| E. cloacae | ECL007 | >64 |
| E. coli | ECO005 | >64 |
| E. faecalis | EFS004 | >64 |
| K. pneumoniae | KP001 | >64 |
| P. aeruginosa | PA004 | >64 |
| S. aureus | SA006 | 16 |
| S. epidermidis | SE010 | 128 |
| S. maltophilia | SMA002 | >64 |
| S. marcescens | SMS003 | >64 |

TABLE 5-continued

| Organism | Organism # | MIC (µg/ml) |
|---|---|---|
| 12. MBI 11M4 | | |
| E. faecium | EFM001 | 32 |
| E. faecalis | EFS001 | 32 |
| S. aureus | SA008 | 8 |
| 13. MBI 11M8 | | |
| E. faecalis | EFS002 | 32 |
| E. faecium | EFM002 | 32 |
| S. aureus | SA008 | 32 |
| 14. MBI 11A1CN | | |
| A. calcoaceticus | AC002 | 16 |
| E. cloacae | ECL007 | >128 |
| E. coli | ECO002 | 32 |
| E. faecium | EFM002 | 1 |
| E. faecalis | EFS002 | 32 |
| H. influenzae | HIN002 | >128 |
| K. pneumoniae | KP002 | >128 |
| P. aeruginosa | PA004 | >128 |
| S. aureus | SA005 | 8 |
| P. vulgaris | SBPV1 | >128 |
| S. marcescens | SBSM2 | >128 |
| S. pneumoniae | SBSPN2 | >128 |
| S. epidermidis | SE002 | 16 |
| S. maltophilia | SMA002 | >128 |
| 15. MBI 11A2CN | | |
| A. calcoaceticus | AC001 | >128 |
| E. cloacae | ECL007 | >128 |
| E. coli | ECO003 | >128 |
| E. faecium | EFM003 | 16 |
| E. faecalis | EFS002 | >128 |
| K. pneumoniae | KP002 | >128 |
| P. aeruginosa | PA004 | >128 |
| S. aureus | SA004 | 8 |
| S. maltophilia | SMA001 | >128 |
| S. marcescens | SMS003 | >128 |
| 16. MBI 11A3CN | | |
| A. calcoaceticus | AC001 | >128 |
| E. cloacae | ECL007 | >128 |
| E. coli | ECO002 | >128 |
| E. faecium | EFM003 | 64 |
| E. faecalis | EFS002 | >128 |
| H. influenzae | HIN002 | >128 |
| K. pneumoniae | KP001 | >128 |
| P. aeruginosa | PA002 | >128 |
| S. aureus | SA004 | 32 |
| P. vulgaris | SBPV1 | >128 |
| S. marcescens | SBSM2 | >128 |
| S. pneumoniae | SBSPN3 | >128 |
| S. epidermidis | SE002 | 128 |
| S. maltophilia | SMA001 | >128 |
| 17. MBI 11A4CN | | |
| A. calcoaceticus | AC002 | 8 |
| E. cloacae | ECL007 | >128 |
| E. coli | ECO003 | 32 |
| E. faecalis | EFS002 | 64 |
| E. faecium | EFM001 | 32 |
| K. pneumoniae | KP001 | >128 |
| P. aeruginosa | PA004 | >128 |
| S. aureus | SA005 | 2 |
| S. epidermidis | SE002 | 8 |
| S. maltophilia | SMA002 | >128 |
| S. marcescens | SMS004 | >128 |
| 18. MBI 11A5CN | | |
| A. calcoaceticus | AC001 | >128 |
| E. cloacae | ECL007 | >128 |
| E. coli | ECO003 | 128 |
| E. faecium | EFM003 | 4 |
| E. faecalis | EFS002 | 32 |
| K. pneumoniae | KP001 | >128 |
| P. aeruginosa | PA003 | >128 |
| S. aureus | SA002 | 16 |
| S. maltophilia | SMA002 | >128 |
| S. marcescens | SMS003 | >128 |
| 19. MBI 11A6CN | | |
| E. faecium | EFM003 | 2 |
| E. faecalis | EFS004 | 64 |
| S. aureus | SA016 | 2 |
| 20. MBI 11A7CN | | |
| E. faecium | EFM003 | 2 |
| E. faecalis | EFS002 | 16 |
| S. aureus | SA009 | 2 |
| 21. MBI 11A8CN | | |
| A. calcoaceticus | AC002 | 8 |
| E. cloacae | ECL007 | >128 |
| E. coli | ECO005 | 32 |
| E. faecalis | EFS001 | 4 |
| K. pneumoniae | KP001 | 128 |
| P. aeruginosa | PA004 | >128 |
| S. aureus | SA093 | 1 |
| S. epidermidis | SE010 | 16 |
| S. maltophilia | SMA002 | 32 |
| S. marcescens | SMS003 | >128 |
| 22. MBI 11B1CN | | |
| A. calcoaceticus | AC001 | 32 |
| E. cloacae | ECL007 | >128 |
| E. coli | ECO003 | 8 |
| E. faecium | EFM002 | 2 |
| E. faecalis | EFS004 | 8 |
| K. pneumoniae | KP002 | 64 |
| P. aeruginosa | PA005 | >128 |
| S. aureus | SA005 | 2 |
| S. epidermidis | SE001 | 2 |
| S. maltophilia | SMA001 | 64 |
| S. marcescens | SMS004 | >128 |
| 23. MBI 11B1CNW1 | | |
| A. calcoaceticus | AC002 | 16 |
| E. cloacae | ECL007 | 64 |
| E. coli | ECO005 | 32 |
| E. faecalis | EFS004 | 8 |
| K. pneumoniae | KP001 | 32 |
| P. aeruginosa | PA004 | 64 |
| S. aureus | SA014 | 16 |
| S. epidermidis | SE010 | 8 |
| S. maltophilia | SMA002 | 32 |
| S. marcescens | SMS003 | >128 |
| 24. MBI 11B2CN | | |
| A. calcoaceticus | AC001 | 64 |
| E. cloacae | ECL007 | >128 |
| E. coli | ECO003 | 16 |
| E. faecium | EFM001 | 8 |
| E. faecalis | EFS004 | 8 |
| K. pneumoniae | KP002 | 64 |
| P. aeruginosa | PA003 | >128 |
| S. aureus | SA005 | 2 |
| S. maltophilia | SMA002 | 64 |
| S. marcescens | SMS004 | >128 |
| 25. MBI 11B3CN | | |
| A. calcoaceticus | AC001 | 64 |
| E. cloacae | ECL007 | >128 |
| E. coli | ECO002 | 16 |
| E. faecium | EFM001 | 8 |
| E. faecalis | EFS001 | 16 |
| K. pneumoniae | KP002 | 64 |
| P. aeruginosa | PA003 | >128 |
| S. aureus | SA010 | 4 |
| S. maltophilia | SMA002 | 32 |
| S. marcescens | SMS004 | >128 |
| 26. MBI 11B4CN | | |
| A. calcoaceticus | AC001 | >128 |
| E. cloacae | ECL007 | >128 |

S. maltophilia SMA002 >128
S. marcescens SMS003 >128

TABLE 5-continued

| Organism | Organism # | MIC (µg/ml) |
|---|---|---|
| E. coli | ECO003 | 16 |
| E. faecalis | EFS002 | 16 |
| H. influenzae | HIN002 | >128 |
| K. pneumoniae | KP002 | 128 |
| P. aeruginosa | PA006 | >128 |
| S. aureus | SA004 | 2 |
| S. marcescens | SBSM2 | >128 |
| S. pneumoniae | SBSPN3 | 128 |
| S. epidermidis | SE010 | 4 |
| S. maltophilia | SMA002 | 64 |
| S. marcescens | SMS004 | >128 |
| 27. MBI 11B4ACN | | |
| A. calcoaceticus | AC002 | 4 |
| E. cloacae | ECL007 | >128 |
| E. coli | ECO005 | 32 |
| E. faecalis | EFS008 | 64 |
| K. pneumoniae | KP001 | 32 |
| P. aeruginosa | PA004 | >128 |
| S. aureus | SA008 | 1 |
| S. epidermidis | SE010 | 8 |
| S. maltophilia | SMA002 | 64 |
| S. marcescens | SMS003 | >128 |
| 28. MBI 11B5CN | | |
| E. faecium | EFM002 | 1 |
| E. faecalis | EFS002 | 16 |
| S. aureus | SA005 | 2 |
| 29. MBI 11B7 | | |
| A. calcoaceticus | AC002 | 4 |
| E. cloacae | ECL007 | >128 |
| E. coli | ECO005 | 16 |
| E. faecalis | EFS008 | 8 |
| K. pneumoniae | KP001 | 16 |
| P. aeruginosa | PA004 | >128 |
| S. aureus | SA093 | 1 |
| S. epidermidis | SE010 | 4 |
| S. maltophilia | SMA002 | 64 |
| S. marcescens | SMS003 | >128 |
| 30. MBI 11B7CN | | |
| A. calcoaceticus | AC003 | 32 |
| E. cloacae | ECL009 | 32 |
| E. coli | ECO002 | 8 |
| E. faecium | EFM001 | 4 |
| E. faecalis | EFS004 | 4 |
| H. influenzae | HIN002 | >128 |
| K. pneumoniae | KP001 | 32 |
| P. aeruginosa | PA004 | 128 |
| P. mirabilis | PM002 | >128 |
| S. aureus | SA009 | 2 |
| S. marcescens | SBSM1 | >128 |
| S. pneumoniae | SBSPN3 | >128 |
| S. epidermidis | SE003 | 2 |
| S. maltophilia | SMA004 | 128 |
| S. pyogenes | SPY006 | 16 |
| 31. MBI 11B7CNR | | |
| A. calcoaceticus | AC002 | 4 |
| E. cloacae | ECL007 | 64 |
| E. coli | ECO005 | 8 |
| E. faecalis | EFS001 | 4 |
| K. pneumoniae | KP001 | 8 |
| P. aeruginosa | PA004 | 64 |
| S. aureus | SA093 | 2 |
| S. epidermidis | SE010 | 4 |
| S. maltophilia | SMA002 | 32 |
| S. marcescens | SMS003 | >128 |
| 32. MBI 11B8CN | | |
| A. calcoaceticus | AC001 | >128 |
| E. cloacae | ECL007 | >128 |
| E. coli | ECO002 | 16 |
| E. faecium | EFM001 | 16 |
| E. faecalis | EFS002 | 32 |
| K. pneumoniae | KP001 | |

TABLE 5-continued

| Organism | Organism # | MIC (µg/ml) |
|---|---|---|
| P. aeruginosa | PA005 | >128 |
| S. aureus | SA009 | 4 |
| S. epidermidis | SF002 | 4 |
| S. maltophilia | SMA002 | 128 |
| S. marcescens | SMS003 | >128 |
| 33. MBI 11B9CN | | |
| A. calcoaceticus | AC002 | 4 |
| E. cloacae | ECL007 | >128 |
| E. coli | ECO005 | 8 |
| E. faecium | EFM002 | 4 |
| E. faecalis | EFS002 | 8 |
| H. influenzae | HIN002 | >128 |
| K. pneumoniae | KP001 | 32 |
| P. aeruginosa | PA004 | 128 |
| P. mirabilis | PM002 | >128 |
| S. aureus | SA010 | 4 |
| S. pneumoniae | SBSPN2 | >128 |
| S. epidermidis | SE010 | 2 |
| S. maltophilia | SMA002 | 32 |
| S. marcescens | SMS003 | >128 |
| S. pneumoniae | SPN044 | >128 |
| S. pyogenes | SPY005 | 16 |
| 34. MBI 11B9ACN | | |
| A. calcoaceticus | AC001 | 32 |
| E. cloacae | ECL007 | >128 |
| E. coli | ECO003 | 8 |
| E. faecium | EFM001 | 4 |
| E. faecalis | EFS004 | 8 |
| K. pneumoniae | KP002 | 32 |
| P. aeruginosa | PA005 | >128 |
| S. aureus | SA019 | 2 |
| S. epidermidis | SE002 | 2 |
| S. maltophilia | SMA001 | 16 |
| S. marcescens | SMS004 | >128 |
| 35. MBI 11B10CN | | |
| E. faecium | EFM003 | 4 |
| E. faecalis | EFS002 | 64 |
| S. aureus | SA008 | 2 |
| 36. MBI 11B16CN | | |
| A. calcoaceticus | AC002 | 4 |
| E. cloacae | ECL007 | >128 |
| E. coli | ECO005 | 16 |
| E. faecalis | EFS001 | 2 |
| K. pneumoniae | KP001 | 16 |
| P. aeruginosa | PA004 | >128 |
| S. aureus | SA093 | 2 |
| S. epidermidis | SE010 | 4 |
| S. maltophilia | SMA002 | 32 |
| S. marcescens | SMS003 | >128 |
| 37. MBI 11B17CN | | |
| A. calcoaceticus | AC002 | 2 |
| E. cloacae | ECL007 | >128 |
| E. coli | ECO005 | 8 |
| E. faecalis | EFS008 | 4 |
| K. pneumoniae | KP001 | 16 |
| P. aeruginosa | PA004 | >128 |
| S. aureus | SA093 | 2 |
| S. epidermidis | SE010 | 4 |
| S. maltophilia | SMA002 | 32 |
| S. marcescens | SMS003 | >128 |
| 38. MBI 11B18CN | | |
| A. calcoaceticus | AC002 | 2 |
| E. cloacae | ECL007 | >128 |
| E. coli | ECO005 | 32 |
| E. faecalis | EFS008 | 4 |
| K. pneumoniae | KP001 | 32 |
| P. aeruginosa | PA004 | >128 |
| S. aureus | SA093 | 2 |
| S. epidermidis | SE010 | 4 |
| S. maltophilia | SMA002 | 64 |
| S. marcescens | SMS003 | >128 |

TABLE 5-continued

| Organism | Organism # | MIC (µg/ml) |
|---|---|---|
| 39. MBI 11C3CN | | |
| A. calcoaceticus | AC002 | 4 |
| E. cloacae | ECL007 | >128 |
| E. coli | ECO002 | 16 |
| E. faecium | EFM002 | 1 |
| E. faecalis | EFS002 | 32 |
| K. pneumoniae | KP001 | 128 |
| P. aeruginosa | PA005 | >128 |
| S. aureus | SA005 | 2 |
| S. epidermidis | SE002 | 2 |
| S. maltophilia | SMA002 | 64 |
| S. marcescens | SMS004 | >128 |
| 40. MBI 11C4CN | | |
| A. calcoaceticus | AC002 | 4 |
| E. cloacae | ECL007 | >128 |
| E. coli | ECO005 | 32 |
| E. faecium | EFM003 | 2 |
| E. faecalis | EFS002 | 32 |
| K. pneumoniae | KP001 | >128 |
| P. aeruginosa | PA005 | >128 |
| S. aureus | SA009 | 4 |
| S. epidermidis | SE002 | 4 |
| S. maltophilia | SMA002 | 64 |
| S. marcescens | SMS004 | >128 |
| 41. MBI 11C5CN | | |
| A. calcoaceticus | AC001 | 32 |
| E. cloacae | ECL007 | >128 |
| E. coli | ECO001 | 8 |
| E. faecium | EFM003 | 2 |
| E. faecalis | EFS002 | 16 |
| K. pneumoniae | KP002 | 16 |
| P. aeruginosa | PA003 | 64 |
| S. aureus | SA009 | 2 |
| S. epidermidis | SE002 | 2 |
| S. maltophilia | SMA002 | 16 |
| S. marcescens | SMS004 | >128 |
| 42. MBI 11D1CN | | |
| A. calcoaceticus | AC001 | >128 |
| E. cloacae | ECL007 | >128 |
| E. coli | ECO002 | 16 |
| E. faecium | EFM001 | 16 |
| E. faecalis | EFS002 | 32 |
| K. pneumoniae | KP002 | 64 |
| P. aeruginosa | PA003 | >128 |
| S. aureus | SA004 | 2 |
| S. epidermidis | SE010 | 8 |
| S. maltophilia | SMA001 | 64 |
| S. marcescens | SMS003 | >128 |
| 43. MBI 11D3CN | | |
| A. calcoaceticus | AC001 | >128 |
| E. cloacae | ECL007 | >128 |
| E. coli | ECO002 | 64 |
| E. faecium | EFM003 | 8 |
| E. faecalis | EFS002 | 32 |
| K. pneumoniae | KP002 | >128 |
| P. aeruginosa | PA024 | >128 |
| S. aureus | SA009 | 8 |
| S. maltophilia | SMA001 | 64 |
| S. marcescens | SMS004 | >128 |
| 44. MBI 11D4CN | | |
| A. calcoaceticus | AC001 | >64 |
| E. cloacae | ECL007 | >64 |
| E. coli | ECO003 | 64 |
| E. faecium | EFM002 | 1 |
| E. faecalis | EFS002 | 16 |
| K. pneumoniae | KP002 | >64 |
| P. aeruginosa | PA004 | >64 |
| S. aureus | SA009 | 4 |
| S. maltophilia | SMA001 | >64 |
| S. marcescens | SMS004 | >64 |
| 45. MBI 11D5CN | | |
| A. calcoaceticus | AC001 | >64 |
| E. cloacae | ECL007 | >64 |
| E. coli | ECO003 | 64 |
| E. faecium | EFM003 | 1 |
| E. faecalis | EFS002 | 16 |
| K. pneumoniae | KP001 | >64 |
| P. aeruginosa | PA003 | >64 |
| S. aureus | SA005 | 8 |
| S. maltophilia | SMA001 | 64 |
| S. marcescens | SMS004 | >64 |
| 46. MBI 11D6CN | | |
| A. calcoaceticus | AC002 | 4 |
| E. cloacae | ECL007 | >32 |
| E. coli | ECO002 | 32 |
| E. faecium | EFM003 | 1 |
| E. faecalis | EFS002 | 4 |
| K. pneumoniae | KP002 | >64 |
| P. aeruginosa | PA024 | >64 |
| S. aureus | SA009 | 8 |
| S. epidermidis | SE010 | 4 |
| S. maltophpilia | SMA001 | >64 |
| S. marcescens | SMS004 | >64 |
| 47. MBI 11D9M8 | | |
| E. faecium | EFM002 | 32 |
| S. aureus | SA007 | 32 |
| E. faecalis | EFS002 | 128 |
| S. aureus | SA016 | 128 |
| 48. MBI 11D10M8 | | |
| E. faecium | EFM003 | 32 |
| E. faecalis | EFS002 | 32 |
| S. aureus | SA008 | 32 |
| 49. MBI 11D11H | | |
| A. calcoaceticus | AC001 | >64 |
| E. cloacae | ECL007 | >64 |
| E. coli | ECO002 | 32 |
| K. pneumoniae | KP001 | >64 |
| P. aeruginosa | PA001 | >64 |
| S. aureus | SA008 | 4 |
| S. maltophilia | SMA002 | >64 |
| S. marcescens | SMS004 | >64 |
| 50. MBI 11D12H | | |
| A. calcoaceticus | AC001 | >64 |
| E. cloacae | ECL007 | >64 |
| E. coli | ECO003 | 64 |
| E. faecalis | EFS004 | 16 |
| K. pneumoniae | KP002 | >64 |
| P. aeruginosa | PA004 | >64 |
| S. aureus | SA014 | 16 |
| S. maltophilia | SMA002 | >64 |
| S. marcescens | SMS004 | >64 |
| 51. MBI 11D13H | | |
| A. calcoaceticus | AC001 | 64 |
| E. cloacae | ECL007 | >64 |
| E. coli | ECO002 | 32 |
| E. faecalis | EFS004 | 16 |
| K. pneumoniae | KP002 | >64 |
| P. aeruginosa | PA004 | >64 |
| S. aureus | SA025 | 4 |
| S. maltophilia | SMA002 | >64 |
| S. marcescens | SMS004 | >64 |
| 52. MBI 11D14CN | | |
| E. faecium | EFM003 | 1 |
| E. faecalis | EFS002 | 32 |
| S. aureus | SA009 | 4 |

TABLE 5-continued

| Organism | Organism # | MIC (µg/ml) |
|---|---|---|
| 53. MBI 11D15CN | | |
| E. faecium | EFM003 | 4 |
| E. faecalis | EFS002 | 32 |
| S. aureus | SA009 | 8 |
| 54. MBI 11D18CN | | |
| A. calcoaceticus | AC003 | 32 |
| E. cloacae | ECL009 | 64 |
| E. coli | ECO002 | 4 |
| E. faecium | EFM003 | 2 |
| E. faecalis | EFS002 | 32 |
| H. influenzae | HIN002 | >128 |
| K. pneumoniae | KP002 | 64 |
| P. aeruginosa | PA006 | >128 |
| P. mirabilis | PM003 | >128 |
| S. aureus | SA010 | 4 |
| P. vulgaris | SBPV1 | 32 |
| S. marcescens | SBSM2 | >128 |
| S. pneumoniae | SBSPN3 | 64 |
| S. epidermidis | SE010 | 2 |
| S. maltophilia | SMA003 | 16 |
| S. pyogenes | SPY003 | 32 |
| 55. MBI 11E1CN | | |
| A. calcoaceticus | AC001 | 32 |
| E. cloacae | ECL007 | >128 |
| E. coli | ECO003 | 8 |
| E. faecium | EFM001 | 8 |
| E. faecalis | EFS002 | 8 |
| K. pneumoniae | KP002 | 32 |
| P. aeruginosa | PA003 | 128 |
| S. aureus | SA006 | 1 |
| S. maltophilia | SMA001 | 64 |
| S. marcescens | SMS003 | >128 |
| 56. MBI 11E2CN | | |
| A. calcoaceticus | AC002 | 4 |
| E. cloacae | ECL007 | >128 |
| E. coli | ECO002 | 8 |
| E. faecium | EFM001 | 16 |
| E. faecalis | EFS002 | 32 |
| K. pneumoniae | KP002 | 64 |
| P. aeruginosa | PA001 | >128 |
| S. aureus | SA016 | 2 |
| S. epidermidis | SE010 | 4 |
| S. maltophilia | SMA001 | 64 |
| S. marcescens | SMS004 | >128 |
| 57. MBI 11E3CN | | |
| A. calcoaceticus | AC001 | 16 |
| E. cloacae | ECL007 | >128 |
| E. coli | ECO001 | 4 |
| E. faecium | EFM003 | 2 |
| E. faecalis | EFS004 | 8 |
| H. influenzae | HIN002 | >128 |
| K. pneumoniae | KP002 | 32 |
| P. aeruginosa | PA041 | 64 |
| P. mirabilis | PM001 | >128 |
| S. aureus | SA010 | 2 |
| S. pneumoniae | SBSPN2 | >128 |
| S. epidermidis | SE002 | 1 |
| S. maltophilia | SMA001 | 32 |
| S. marcescens | SMS004 | >128 |
| S. pneumoniae | SPN044 | >128 |
| S. pyogenes | SPY002 | 16 |
| 58. MBI 11F1CN | | |
| E. cloacae | ECL007 | >128 |
| E. coli | ECO003 | 8 |
| E. faecium | EFM003 | 2 |
| E. faecalis | EFS004 | 16 |
| K. pneumoniae | KP002 | 32 |
| P. aeruginosa | PA004 | 64 |
| S. aureus | SA009 | 2 |
| S. marcescens | SBSM1 | >128 |
| S. marcescens | SMS003 | >128 |
| 59. MBI 11F2CN | | |
| A. calcoaceticus | AC002 | 4 |
| E. coli | ECO002 | 8 |
| E. faecium | EFM002 | 4 |
| E. faecalis | EFS002 | 32 |
| K. pneumoniae | KP002 | 128 |
| P. aeruginosa | PA005 | >128 |
| S. aureus | SA012 | 4 |
| S. epidermidis | SE002 | 4 |
| S. maltophilia | SMA002 | 64 |
| S. marcescens | SMS004 | >128 |
| 60. MBI 11F3CN | | |
| A. calcoaceticus | AC002 | 4 |
| E. cloacae | ECL007 | >128 |
| E. coli | ECO002 | 8 |
| E. faecium | EFM003 | 4 |
| E. faecalis | EFS002 | 8 |
| H. influenzae | HIN002 | >128 |
| K. pneumoniae | KP002 | 64 |
| P. aeruginosa | PA041 | 128 |
| S. aureus | SA005 | 2 |
| S. pneumoniae | SBSPN3 | >128 |
| S. epidermidis | SE003 | 2 |
| S. maltophilia | SMA002 | 64 |
| S. marcescens | SMS004 | >128 |
| S. pneumoniae | SPN044 | >128 |
| S. pyogenes | SPY006 | 8 |
| 61. MBI 11F4CN | | |
| A. calcoaceticus | AC003 | 16 |
| E cloacae | ECL006 | 16 |
| E. coli | ECO001 | 8 |
| E. faecalis | EFS004 | 8 |
| H. influenzae | HIN003 | >128 |
| K. pneumoniae | KP001 | 8 |
| P. aeruginosa | PA020 | 32 |
| S. aureus | SA007 | 1 |
| S. marcescens | SBSM1 | >128 |
| S. pneumoniae | SBSPN3 | >128 |
| S. epidermidis | SE010 | 2 |
| S. maltophilia | SMA006 | 16 |
| S. pyogenes | SPY005 | 32 |
| 62. MBI 11F4CNR | | |
| A. calcoaceticus | AC002 | 16 |
| E. cloacae | ECL007 | 32 |
| E. coli | ECO005 | 32 |
| E. faecalis | EFS008 | 32 |
| K. pneumoniae | KP001 | 32 |
| P. aeruginosa | PA004 | 64 |
| S. aureus | SA093 | 8 |
| S. epidermidis | SE010 | 8 |
| S. maltophilia | SMA002 | 32 |
| S. marcescens | SMS003 | >128 |
| 63. MBI 11G2CN | | |
| E. cloacae | ECL007 | >128 |
| E. coli | ECO003 | 16 |
| E. faecium | EFM002 | 4 |
| E. faecalis | EFS004 | 16 |
| K. pneumoniae | KP002 | 128 |
| P. aeruginosa | PA004 | >128 |
| S. aureus | SA009 | 2 |
| S. maltophilia | SMA001 | >128 |
| S. marcescens | SMS004 | >128 |
| 64. MBI 11G3CN | | |
| E. cloacae | ECL007 | >128 |
| E. coli | ECO003 | 64 |
| E. faecium | EFM002 | 32 |
| E. faecalis | EFS002 | 64 |
| K. pneumoniae | KP001 | >128 |
| P. aeruginosa | PA003 | >128 |
| S. aureus | SA009 | 8 |
| S. maltophilia | SMA001 | >128 |

TABLE 5-continued

| Organism | Organism # | MIC (µg/ml) |
|---|---|---|
| S. marcescens | SMS004 | >128 |
| 65. MBI 11G4CN | | |
| A. calcoaceticus | AC002 | 4 |
| E. cloacae | ECL007 | >128 |
| E. coli | ECO005 | 32 |
| E. faecium | EFM003 | 1 |
| E. faecalis | EFS002 | 32 |
| K. pneumoniae | KP001 | >128 |
| P. aeruginosa | PA004 | >128 |
| S. aureus | SA004 | 1 |
| S. epidermidis | SE010 | 2 |
| S. maltophilia | SMA002 | 64 |
| S. marcescens | SMS003 | >128 |
| 66. MBI 11G5CN | | |
| A. calcoaceticus | AC002 | 4 |
| E. cloacae | ECL007 | >128 |
| E. coli | ECO003 | 16 |
| E. faecium | EFM002 | 8 |
| E. faecalis | EFS002 | 16 |
| K. pnuemoniae | KP001 | >128 |
| P. aeruginosa | PA003 | >128 |
| S. aureus | SA012 | 4 |
| S. epidermidis | SE002 | 2 |
| S. maltophilia | SMA002 | 64 |
| S. marcescens | SMS004 | >128 |
| 67. MBI 11G6CN | | |
| A. calcoaceticus | AC001 | >128 |
| E. cloacae | ECL007 | >128 |
| E. coli | ECO002 | 32 |
| E. faecium | EFM003 | 4 |
| E. faecalis | EFS002 | 128 |
| K. pneumoniae | KP001 | >128 |
| P. aeruginosa | PA004 | >128 |
| S. aureus | SA006 | 2 |
| S. epidermidis | SE002 | 8 |
| S. maltophilia | SMA001 | >128 |
| S. marcescens | SMS003 | >128 |
| 68. MBI 11G6ACN | | |
| A. calcoaceticus | AC002 | 4 |
| E. cloacae | ECL007 | >128 |
| E. coli | ECO005 | 64 |
| E. faecalis | EFS008 | >128 |
| K. pneumoniae | KP001 | >128 |
| P. aeruginosa | PA004 | >128 |
| S. aureus | SA014 | 64 |
| S epidermidis | SE010 | 32 |
| S. maltophilia | SMA002 | >128 |
| S. marcescens | SMS003 | >128 |
| 69. MBI 11G7CN | | |
| A. calcoaceticus | AC001 | 128 |
| E. cloacae | ECL006 | 64 |
| E. coli | ECO005 | 8 |
| E. faecium | EFM001 | 8 |
| E. faecalis | EFS002 | 32 |
| H. influenzae | HIN002 | >128 |
| K. pneumoniae | KP001 | 16 |
| P. aeruginosa | PA006 | >128 |
| S. aureus | SA012 | 2 |
| H. influenzae | SBHIN2 | >128 |
| S. marcescens | SBSM1 | >128 |
| S. pneumoniae | SBSPN2 | >128 |
| S. epidermidis | SE002 | 2 |
| S. maltophilia | SMA001 | 32 |
| S. marcescens | SMS003 | >128 |
| S. pneumoniae | SPN044 | >128 |
| S. pyogenes | SPY006 | 16 |
| 70. MBI 11G7ACN | | |
| A. calcoaceticus | AC002 | 4 |
| E. cloacae | ECL007 | >32 |
| E. coli | ECO002 | 16 |
| E. faecium | EFM001 | 8 |

TABLE 5-continued

| Organism | Organism # | MIC (µg/ml) |
|---|---|---|
| E. faecalis | EFS008 | 32 |
| K. pneumoniae | KP002 | >32 |
| P. aeruginosa | PA006 | >32 |
| S. aureus | SA010 | 1 |
| S. epidermidis | SE002 | 4 |
| S. maltophilia | SMA001 | 32 |
| S. marcescens | SMS004 | >32 |
| 71. MBI 11G13CN | | |
| E. coli | ECO002 | 32 |
| E. faecium | EFM002 | 16 |
| E. faecalis | EFS002 | 64 |
| H. influenzae | HIN002 | >128 |
| P. aeruginosa | PA004 | >128 |
| S. aureus | SA004 | 4 |
| E. coli | SBECO3 | 32 |
| S. marcescens | SBSM1 | >128 |
| S. pneumoniae | SBSPN3 | 128 |
| 72. MBI 11G14CN | | |
| A. calcoaceticus | AC002 | 8 |
| E. cloacae | ECL007 | >128 |
| E. coli | ECO003 | 32 |
| E. faecium | EFM001 | 16 |
| E. faecalis | EFS002 | 32 |
| K. pneumoniae | KP002 | 128 |
| P. aeruginosa | PA006 | >128 |
| S. aureus | SA013 | 0.5 |
| S. epidermidis | SE002 | 8 |
| S. maltophilia | SMA002 | 128 |
| S. marcescens | SMS004 | >128 |
| 73. MBI 11G16CN | | |
| A. calcoaceticus | AC002 | 8 |
| E. cloacae | ECL007 | >128 |
| E. coli | ECO005 | 16 |
| E. faecalis | EFS008 | 16 |
| K. pneumoniae | KP001 | 16 |
| P. aeruginosa | PA004 | 128 |
| S. aureus | SA093 | 2 |
| S. epidermidis | SE010 | 4 |
| S. maltophilia | SMA002 | 64 |
| S. marcescens | SMS003 | >128 |

Broth Dilution Assay

This assay also uses calcium and magnesium supplemented Mueller Hinton broth as the growth medium. Typically 100 µl of broth is dispensed into each well of a 96-well microtitre plate and 100 µl volumes of two-fold serial dilutions of the peptide analogue are made across the plate. One row of wells receives no peptide and is used as a growth control. Each well is inoculated with approximately $5 \times 10^5$ CFU of bacteria and the plate is incubated at 35-37° C. for 16-20 hours. The MIC is again recorded at the lowest concentration of peptide that completely inhibits growth of the organism as determined by visual inspection.

For example, MIC values were established for a series of peptide analogues against S. aureus strains. Results are shown in Table 6 below.

TABLE 6

| Organism | Organism # | MIC (μg/ml) | | | | | | |
|---|---|---|---|---|---|---|---|---|
| | | MBI 10CN | MBI 11CN | MBI 11A1CN | MBI 11A2CN | MBI 11B1CN | MBI 11B2CN | MBI 11B7CN |
| Gram-negative: | | | | | | | | |
| A. calcoaceticus | AC001 | 64 | 256 | >256 | >256 | 64 | 128 | 64 |
| E. cloacae | ECL007 | 256 | >256 | >256 | >256 | >256 | >256 | >256 |
| E. coli | ECO005 | 64 | 128 | >256 | >256 | 64 | 64 | 64 |
| K. pneumoniae | KP001 | 64 | >256 | >256 | >256 | >256 | >256 | 256 |
| P. aeruginosa | PA004 | >256 | 256 | >256 | >256 | 64 | 256 | 256 |
| S. maltophilia | SMA002 | 64 | 64 | >256 | >256 | 32 | 32 | 32 |
| S. marcescens | SMS003 | >256 | >256 | >256 | >256 | >256 | >256 | >256 |
| Gram-positive: | | | | | | | | |
| E. faecalis | EFS004 | 64 | 128 | >256 | >256 | 64 | 64 | 64 |
| S. aureus | SA002 | 16 | 64 | >256 | >256 | 32 | 32 | 16 |
| S. epidermidis | SE005 | 8 | 8 | 16 | 256 | 4 | 4 | 4 |

Time Kill Assay

Time kill curves are used to determine the antimicrobial activity of cationic peptides over a time interval. Briefly, in this assay, a suspension of microorganisms equivalent to a 0.5 McFarland Standard is prepared in 0.9% saline. This suspension is then diluted such that when added to a total volume of 9 ml of cation-adjusted Mueller Hinton broth, the inoculum size is $1\times10^6$ CFU/ml. An aliquot of 0.1 ml is removed from each tube at pre-determined intervals up to 24 hours, diluted in 0.9% saline and plated in triplicate to determine viable colony counts. The number of bacteria remaining in each sample is plotted over time to determine the rate of cationic peptide killing. Generally a three or more $\log_{10}$ reduction in bacterial counts in the antimicrobial suspension compared to the growth controls indicate an adequate bactericidal response.

Figure 3A:
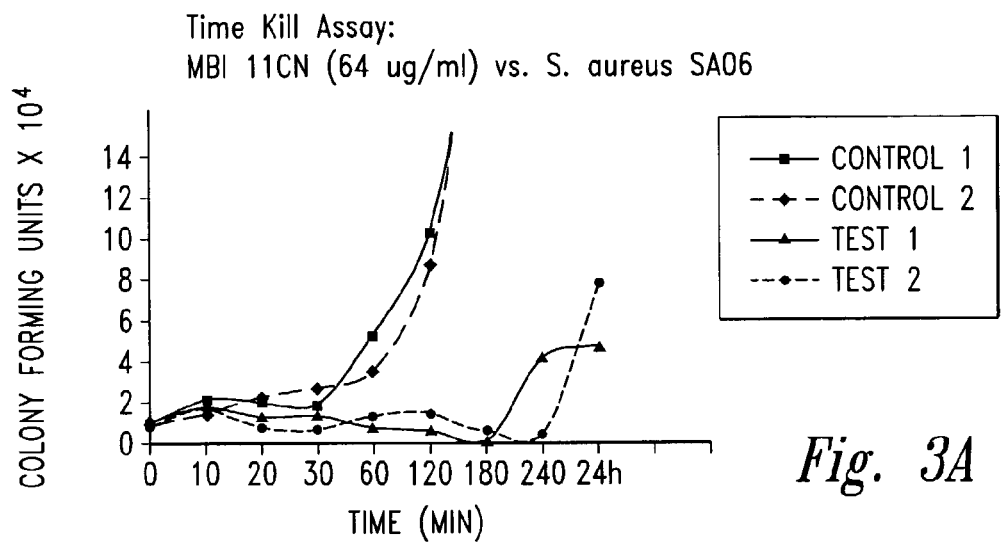
FIG. 3 presents time kill assay results for MBI 11CN, MBI 11F4CN and MBI 11B7CN. The number of colony forming units $\times 10^{-4}$ is plotted versus time.
Figure 3B:
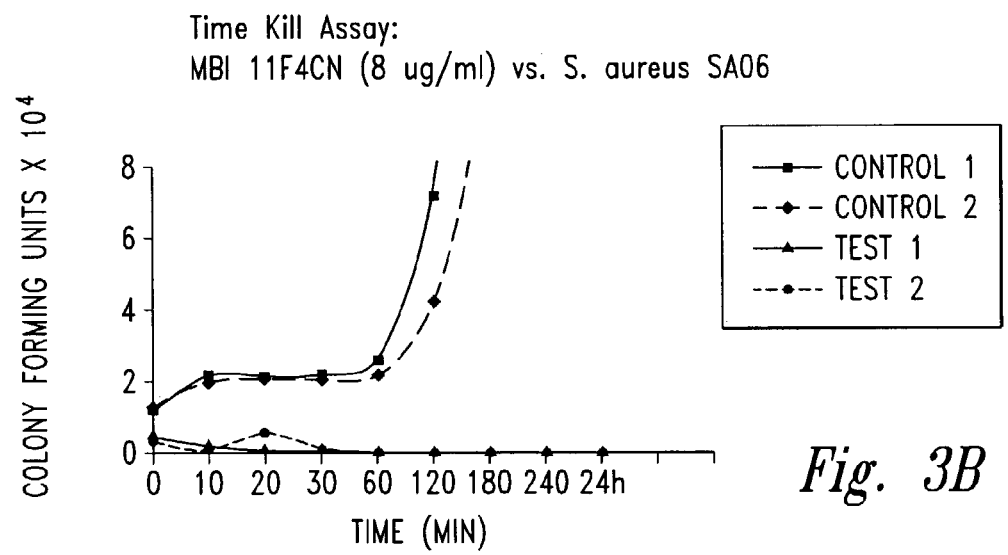
Figure 3C:
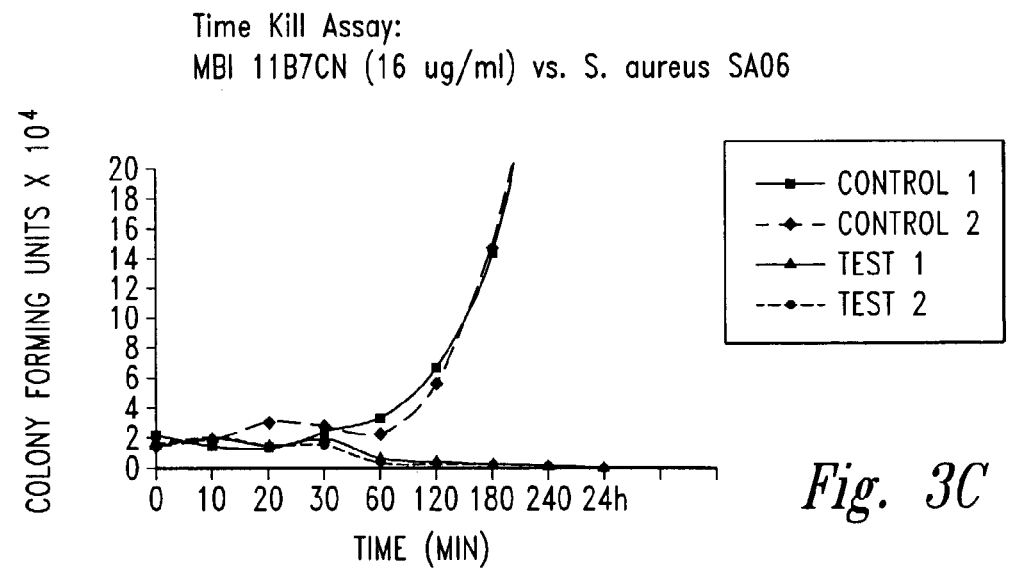

As shown in FIG. 3, all peptides demonstrated a three or more $\log_{10}$ reduction in bacterial counts in the antimicrobial suspension compared to the growth controls indicating that these peptides have met the criteria for a bactericidal response.

Synergy Assay

Treatment with a combination of peptide analogues and conventional antibiotics can have a synergistic effect. Synergy is assayed using the agarose dilution technique, where an array of plates, each containing a combination of peptide and antibiotic in a unique concentration mix, is inoculated with the bacterial isolates. Synergy is investigated for peptide analogues in combination with a number of conventional antibiotics including, but not limited to, penicillins, cephalosporins, carbapenems, monobactams, aminoglycosides, macrolides, fluoroquinolones.

Synergy is expressed as a Fractional Inhibitory Concentration (FIC), which is calculated according to the equation below. An FIC of less than or equal to 0.5 is evidence of synergy, although combinations with higher values may be therapeutically useful.

$$FIC = \frac{MIC(\text{peptide in combination})}{MIC(\text{peptide alone})} + \frac{MIC(\text{antibiotic in combination})}{MIC(\text{antibiotic alone})}$$

Table 7 shows exemplary synergy data for combinations of indolicidin analogues and Mupirocin.

TABLE 7

| Peptide | Organism | Mupirocin MIC (μg/ml) | Mupirocin Comb. MIC (μg/ml) | Peptide MIC (μg/ml) | Peptide Comb. MIC (μg/ml) | FIC |
|---|---|---|---|---|---|---|
| MBI 11A1CN | E. coli ECO1 | >100 | 10 | 32 | 4 | 0.14 |
| MBI 11A1CN | E. faecalis EFS8 | 100 | 100 | >128 | >128 | 2 |
| MBI 11A1CN | P. aeruginosa PA3 | >100 | >100 | >128 | >128 | 2 |
| MBI 11A1CN | S. aureus SBSA3 | 100 | 100 | >128 | >128 | 2 |
| MBI 11A1CN | S. aureus SBSA5 | 30 | 10 | 128 | 32 | 0.58 |
| MBI 11A1CN | S. marcescens SBSM1 | >100 | >100 | >128 | >128 | 2 |
| MBI 11A3CN | E. coli SBECO1 | 100 | 30 | 64 | 8 | 0.43 |
| MBI 11A3CN | E. faecalis EFS8 | 100 | 100 | >128 | >128 | 2 |
| MBI 11A3CN | P. aeruginosa PA3 | >100 | >100 | >128 | >128 | 2 |
| MBI 11A3CN | S. aureus SBSA2 | >100 | >100 | 128 | 128 | 2 |
| MBI 11A3CN | S. marcescens SBSM2 | >100 | >100 | >128 | >128 | 2 |
| MBI 11B4CN | E. coli ECO1 | >100 | 10 | 16 | 4 | 0.26 |
| MBI 11B4CN | E. faecalis EFS8 | 100 | 100 | 64 | 64 | 2 |
| MBI 11B4CN | S. aureus SBSA3 | 100 | 10 | 32 | 16 | 0.60 |
| MBI 11B4CN | S. aureus SBSA4 | >100 | >100 | 8 | 8 | 2 |
| MBI 11B4CN | S. marcescens SBSM1 | >100 | >100 | >128 | >128 | 2 |
| MBI 11D18CN | E. coli SBEC02 | >100 | 10 | 16 | 1 | 0.07 |
| MBI 11D18CN | E. faecalis EFS8 | 100 | 100 | 16 | 16 | 2 |
| MBI 11D18CN | P. aeruginosa PA2 | >100 | 30 | 128 | 64 | 0.53 |

TABLE 7-continued

| Peptide | Organism | Mupirocin MIC (μg/ml) | Mupirocin Comb. MIC (μg/ml) | Peptide MIC (μg/ml) | Peptide Comb. MIC (μg/ml) | FIC |
|---|---|---|---|---|---|---|
| MBI 11D18CN | P. aeruginosa PA24 | >100 | >100 | >128 | >128 | 2 |
| MBI 11D18CN | P. vulgaris SBPV1 | 3 | 3 | 32 | 4 | 1.13 |
| MBI 11D18CN | S. aureus SBSA4 | >100 | 0.1 | 16 | 2 | 0.13 |
| MBI 11D18CN | S. marcescens SBSM1 | >100 | 30 | >128 | 64 | 0.28 |
| MBI 11G13CN | E. coli ECO5 | 100 | 30 | 64 | 8 | 0.43 |
| MBI 11G13CN | P. vulgaris SBPV1 | 3 | 3 | >128 | >128 | 2 |
| MBI 11G13CN | P. vulgaris SBPV1 | 3 | 3 | >128 | 64 | 1.25 |
| MBI 11G13CN | S. aureus SBSA3 | 100 | 100 | 64 | 64 | 2 |
| MBI 11G13CN | S. marcescens SBSM1 | >100 | >100 | >128 | >128 | 2 |

The MIC values of Mupirocin against strains of E. coli, S. aureus, P. aeruginosa are reduced by at least three fold in combination with indolicidin analogues at concentrations that are ≦½ MIC value of the peptide alone.

Table 9 shows exemplary synergy data for combinations of indolicidin analogues and Ciprofloxacin.

TABLE 9

| Peptide | Organism | Ciprofloxacin MIC (μg/ml) | Ciprofloxacin Comb. MIC (μg/ml) | Peptide MIC (μg/ml) | Peptide Comb MIC (μg/ml) | FIC |
|---|---|---|---|---|---|---|
| MBI 11D18CN | S. aureus SA14 | 16 | 8 | 8 | 4 | 1.00 |
| MBI 11D18CN | P. aeruginosa PA24 | 16 | 4 | >128 | 16 | 0.31 |
| MBI 11D18CN | S. aureus SA10 | 32 | 32 | 2 | 2 | 2.00 |

The MIC values of Ciprofloxacin against strains of S. aureus and P. aeruginosa are reduced by at least two fold in combination with indolicidin analogues at concentrations that are ≦½ MIC value of the peptide alone.

Example 5

Biochemical Characterization of Peptide Analogues

Solubility in Formulation Buffer

The primary factor affecting solubility of a peptide is its amino acid sequence. Polycationic peptides are preferably freely soluble in aqueous solutions, especially under low pH conditions. However, in certain formulations, polycationic peptides may form an aggregate that is removed in a filtration step. As peptide solutions for in vivo assays are filtered prior to administration, the accuracy and reproducibility of dosing levels following filtration are examined.

Peptides dissolved in formulations are filtered through a hydrophilic 0.2 μm filter membrane and then analyzed for total peptide content using reversed-phase HPLC. A 100% soluble standard for each concentration is prepared by dissolving the peptide in MilliQ water. Total peak area for each condition is measured and compared with the peak area of the standard in order to provide a relative recovery value for each concentration/formulation combination.

MBI 11CN was prepared in four different buffer systems (A, B, C, and C1) (Table 10, below) at 50, 100, 200 and 400 μg/ml peptide concentrations. With formulations A or B, both commonly used for salvation of peptides and proteins, peptide was lost through filtration in a concentration dependent manner (FIG. 4). Recovery only reached a maximum of 70% at a concentration of 400 μg/ml. In contrast, peptides dissolved in formulations C and C1 were fully recovered. Buffers containing polyanionic ions appear to encourage aggregation, and it is likely that the aggregate takes the form of a matrix which is trapped by the filter. Monoanionic counterions are more suitable for the maintenance of peptides in a non-aggregated, soluble form, while the addition of other solubilizing agents may further improve the formulation.

TABLE 10

| Code | Formulation Buffer |
|---|---|
| A | PBS 200 mM, pH 7.1 |
| B | Sodium Citrate 100 mM, pH 5.2 |
| C | Sodium Acetate 200 mM, pH 4.6 |
| C1 | Sodium Acetate 200 mM/0.5% Polysorbate 80, pH 4.6 |
| D | Sodium Acetate 100 mM/0.5% Activated Polysorbate 80, pH 7.5: Lyophilized/Reconstituted |

Solubility in Broth

The solubility of peptide analogues is assessed in calcium and magnesium supplemented Mueller Hinton broth by visual inspection. The procedure employed is that used for the broth dilution assay except that bacteria are not added to the wells. The appearance of the solution in each well is evaluated according to the scale: (a) clear, no precipitate, (b) light diffuse precipitate and (c) cloudy, heavy precipitate. Results show that, for example, MBI 10CN is less soluble than MBI 11CN under these conditions and that MBI 11BCN analogues are less soluble than MBI 11ACN analogues.

Reversed Phase HPLC Analysis of Peptide Analogue Formulations

Reversed-phase HPLC, which provides an analytical method for peptide quantification, is used to examine peptides in two different formulations. A 400 μg/mL solution of MBI 11CN prepared in formulations C1 and D is analyzed by using a stepwise gradient to resolve free peptide from other species. Standard chromatographic conditions are used as follows:

Solvent A: 0.1% trifluoroacetic acid (TFA) in water
Solvent B: 0.1% TFA/95% acetonitrile in water
Media: POROSO® R2-20 (polystyrene divinylbenzene)

As shown in FIG. 5, MBI 11CN could be separated in two forms, as free peptide in formulation C1, and as a principally formulation-complex peptide in formulation D. This complex survives the separation protocol in gradients containing acetonitrile, which might be expected to disrupt the stability of the complex. A peak corresponding to a small amount (<10%) of free peptide is also observed in formulation D. If the shape of the elution gradient is changed, the associated peptide elutes as a broad low peak, indicating that complexes of peptide in the formulation are heterogeneous.

Example 6

Structural Analysis of Indolicidin Variants Using Circular Dichroism Spectroscopy Circular dichroism (CD) is a spectroscopic technique that measures secondary structures of peptides and proteins in solution, see for example, R. W. Woody, (*Methods in Enzymology*, 246: 34, 1995). The CD spectra of α-helical peptides is most readily interpretable due to the characteristic double minima at 208 and 222 nm. For peptides with other secondary structures however, interpretation of CD spectra is more complicated and less reliable. The CD data for peptides is used to relate solution structure to in vitro activity.

CD measurements of indolicidin analogues are performed in three different aqueous environments, (1) 10 mM sodium phosphate buffer, pH 7.2, (2) phosphate buffer and 40% (v/v) trifluoroethanol (TFE) and (3) phosphate buffer and large (100 nm diameter) unilamellar phospholipid vesicles (liposomes) (Table 11). The organic solvent TFE and the liposomes provide a hydrophobic environment intended to mimic the bacterial membrane where the peptides are presumed to adopt an active conformation.

Figure 6:
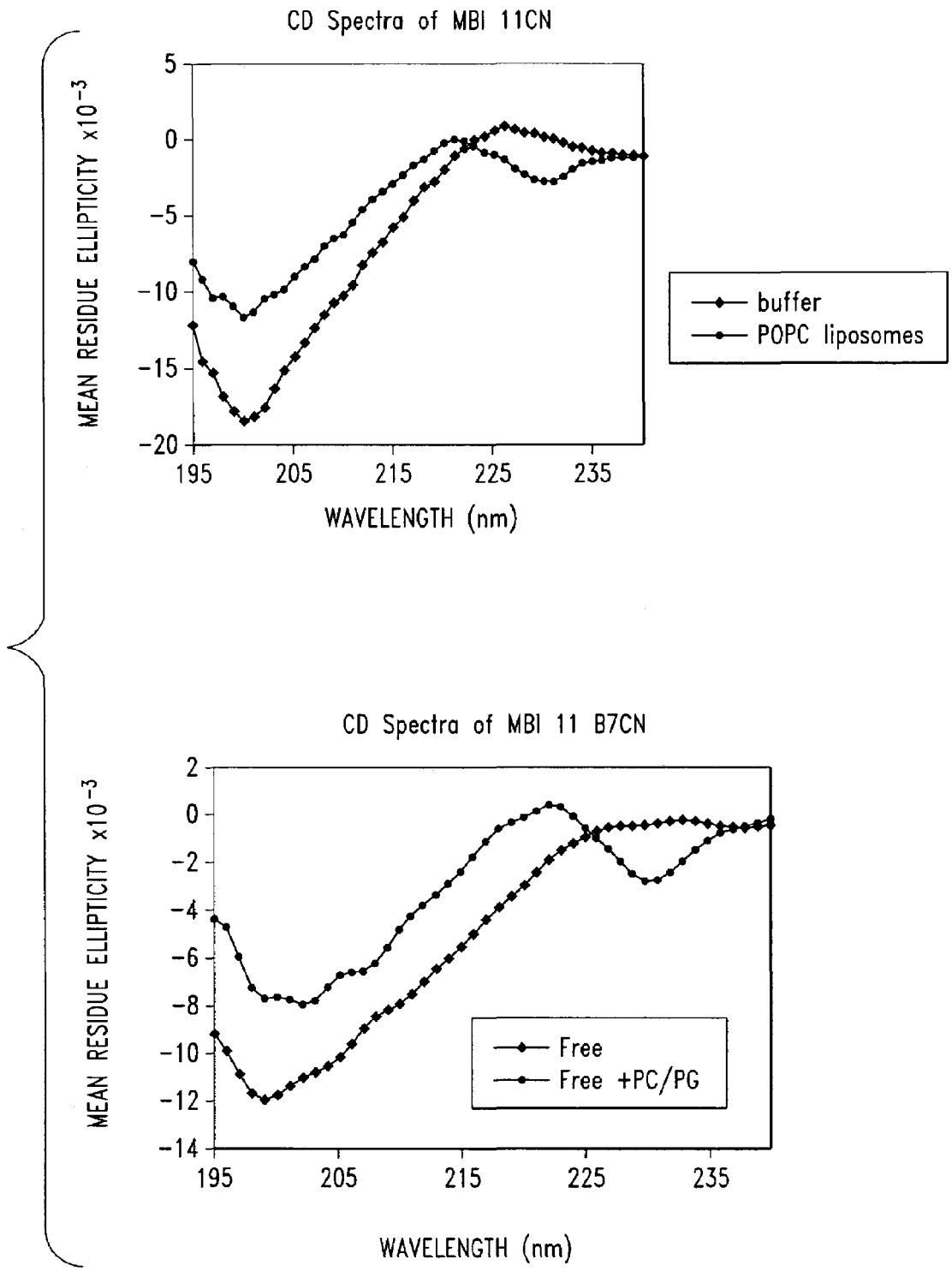
FIG. 6 presents CD spectra of MBI 11CN and MBI 11B7CN.

The results indicate that the peptides are primarily unordered in phosphate buffer (a negative minima at around 200 nm) with the exception of MBI 11F4CN, which displays an additional minima at 220 nm (see below). The presence of TFE induces β-turn structure in MBI 11 and MBI 11G4CN, and increases α-helicity in MBI 11F4CN, although most of the peptides remain unordered. In the presence of liposomes, peptides MBI 11CN and MBI 11B7CN, which are unordered in TFE, display β-turn structure (a negative minima at around 230 nm) (FIG. 6). Hence, liposomes appear to induce more ordered secondary structure than TFE.

A β-turn is the predominant secondary structure that appears in a hydrophobic environment, suggesting that it is the primary conformation in the active, membrane-associated form. In contrast, MBI 11F4CN displays increased α-helical conformation in the presence of TFE. Peptide MBI 11F4CN is also the most insoluble and hemolytic of the peptides tested, suggesting that α-helical secondary structure may introduce unwanted properties in these analogues.

Additionally CD spectra are recorded for APS-modified peptides (Table 11). The results show that these compounds have significant β-turn secondary structure in phosphate buffer, which is only slightly altered in TFE.

Again, the CD results suggest that a β-turn structure (i.e. membrane-associated) is the preferred active conformation among the indolicidin analogues tested.

TABLE 11

| Peptide | Phosphate buffer | | Conformation | TFE | | Conformation |
|---|---|---|---|---|---|---|
| | min λ | max λ | in buffer | min λ | max λ | in TFE |
| MBI 10CN | 201 | — | Unordered | 203 | ~219 | Unordered |
| MBI 11 | 199 | — | Unordered | 202, 227 | 220 | β-turn |
| MBI 11ACN | 199 | — | Unordered | 203 | 219 | Unordered |
| MBI 11CN | 200 | — | Unordered | 200 | — | Unordered |
| MBI 11CNY1 | 200 | — | Unordered | 200 | — | Unordered |
| MBI 11B1CNW1 | 201 | — | Unordered | 201 | — | Unordered |
| MBI 11B4ACN | 200 | — | Unordered | 200 | — | Unordered |
| MBI 11B7CN | 200 | — | Unordered | 204, ~219 | | Unordered |
| MBI 11B9ACN | 200 | — | Unordered | 200 | — | Unordered |
| MBI 11B9CN | 200 | — | Unordered | 200 | — | Unordered |
| MBI 11D1CN | 200 | — | Unordered | 204 | — | Unordered |
| MBI 11E1CN | 201 | — | Unordered | 201 | — | Unordered |
| MBI 11E2CN | 200 | — | Unordered | 201 | — | Unordered |
| MBI 11E3CN | 202 | 226 | ppII helix | 200 | — | Unordered |
| MBI 11F3CN | 199 | 228 | ppII helix | 202 | — | Unordered |
| MBI 11F4CN | 202, 220 | — | Unordered | 206, 222 | — | slight α-helix |
| MBI 11G4CN | 199, 221 | — | Unordered | 201, 226 | 215 | β-turn |
| MBI 11G6ACN | 200 | — | Unordered | 199 | — | Unordered |
| MBI 11G7ACN | 200 | — | Unordered | 202 | 221 | Unordered |

TABLE 12

| APS-modified peptide | Phosphate buffer | | Conformation | TFE | | Conformation |
|---|---|---|---|---|---|---|
| | min λ | max λ | in buffer | min λ | max λ | in TFE |
| MBI 11CN | 202, 229 | 220 | β-turn | 203 | 223 | β-turn |
| MBI 11BCN | 200, 229 | — | β-turn | 202 | 222 | β-turn |
| MBI 11B7CN | 202, 230 | 223 | β-turn | 199 | 230 | β-turn |
| MBI 11E3CN | 202, 229 | 220 | β-turn | 199 | — | β-turn |
| MBI 11F3CN | 205 | — | ppII helix | 203 | 230 | ppII helix |

Example 7

Membrane Permeabilization Assays

Liposome Dye Release

A method for measuring the ability of peptides to permeabilize phospholipid bilayers is described (Parente et al., *Biochemistry*, 29, 8720, 1990) Briefly, liposomes of a defined phospholipid composition are prepared in the presence of a fluorescent dye molecule. In this example, a dye pair consisting of the fluorescent molecule 8-aminonapthalene-1,3,6-trisulfonic acid (ANTS) and its quencher molecule p-xylene-bis-pyridinium bromide (DPX) are used. The mixture of free dye molecules, dye free liposomes, and liposomes containing encapsulated ANTS-DPX are separated by size exclusion chromatography. In the assay, the test peptide is incubated with the ANTS-DPX containing liposomes and the fluorescence due to ANTS release to the outside of the liposome is measured over time.

Using this assay, peptide activity, measured by dye release, is shown to be extremely sensitive to the composition of the liposomes at many liposome to peptide ratios (L/P) (FIG. 7). Specifically, addition of cholesterol to liposomes composed of egg phosphotidylcholine (PC) virtually abolishes membrane permeabilizing activity of MBI 11CN, even at very high lipid to peptide molar ratios (compare with egg PC liposomes containing no cholesterol). This in vitro selectivity may mimic that observed in vitro for bacterial cells in the presence of mammalian cells.

In addition, there is a size limitation to the membrane disruption induced by MBI 11CN. ANTS/DPX can be replaced with fluorescein isothiocyanate-labeled dextran (FD-4), molecular weight 4,400, in the egg PC liposomes. No increase in FD-4 fluorescence is detected upon incubation with MBI 11CN. These results indicate that MBI 11CN-mediated membrane disruption allows the release of the relatively smaller ANTS/DPX molecules (~400 Da), but not the bulkier FD-4 molecules.

*E. coli* ML-35 Inner Membrane Assay

An alternative method for measuring peptide-membrane interaction uses the *E. coli* strain ML-35 (Lehrer et al., *J. Clin. Invest.*, 84: 553, 1989), which contains a chromosomal copy of the lacZ gene encoding β-galactosidase and is permease deficient. This strain is used to measure the effect of peptide on the inner membrane through release of β-galactosidase into the periplasm. Release of β-galactosidase is measured by spectrophotometrically monitoring the hydrolysis of its substrate o-nitrophenol β-D-galactopyranoside (ONPG). The maximum rate of hydrolysis ($V_{max}$) is determined for aliquots of cells taken at various growth points.

A preliminary experiment to determine the concentration of peptide required for maximal activity against mid-log cells, diluted to $4 \times 10^7$ CFU/ml, yields a value of 50 μg/ml, which is used in all subsequent experiments. Cells are grown in two different growth media, Terrific broth (TB) and Luria broth (LB) and equivalent amounts of cells are assayed during their growth cycles. The resulting activity profile of MBI 11B7CN is shown in FIG. 8. For cells grown in the enriched TB media, maximum activity occurs at early mid-log (140 min), whereas for cells grown in LB media, the maximum occurs at late mid-log (230 min). Additionally, only in LB, a dip in activity is observed at 140 min. This drop in activity may be related to a transition in metabolism, such as a requirement for utilization of a new energy source due to depletion of the original source, which does not occur in the more enriched TB media. A consequence of a metabolism switch would be changes in the membrane potential.

Figure 9:
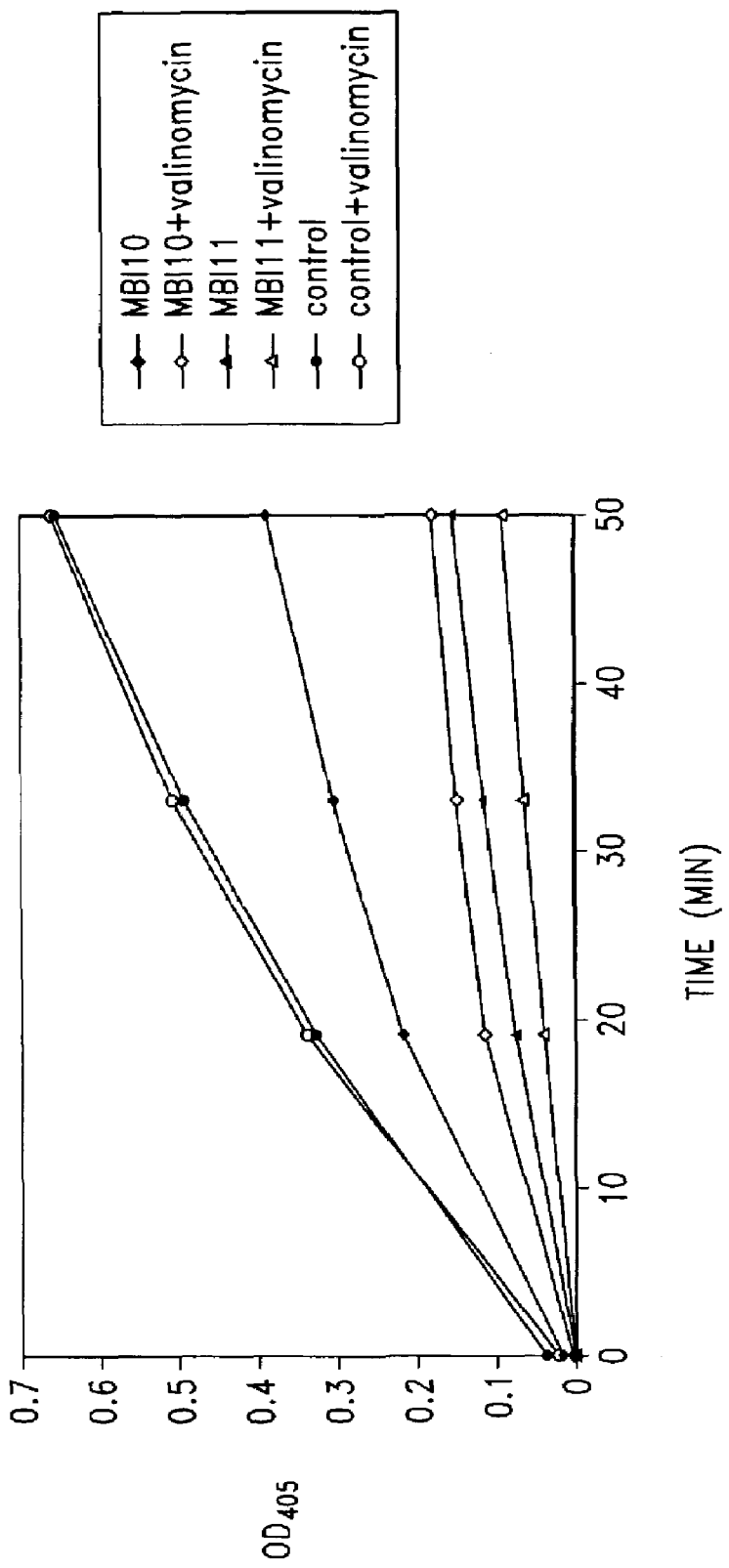
FIG. 9 shows results of treatment of bacteria with MBI 10CN, MBI 11CN, or a control peptide alone or in combination with valinomycin.

To test whether membrane potential has an effect on peptide activity, the effect of disrupting the electrochemical gradient using the potassium ionophore valinomycin is examined. Cells pre-incubated with valinomycin are treated with peptide and for MBI 10CN and MBI 11CN ONPG hydrolysis diminished by approximately 50% compared to no pre-incubation with valinomycin (FIG. 9). Another cationic peptide that is not sensitive to valinomycin is used as a positive control.

Figure 10:
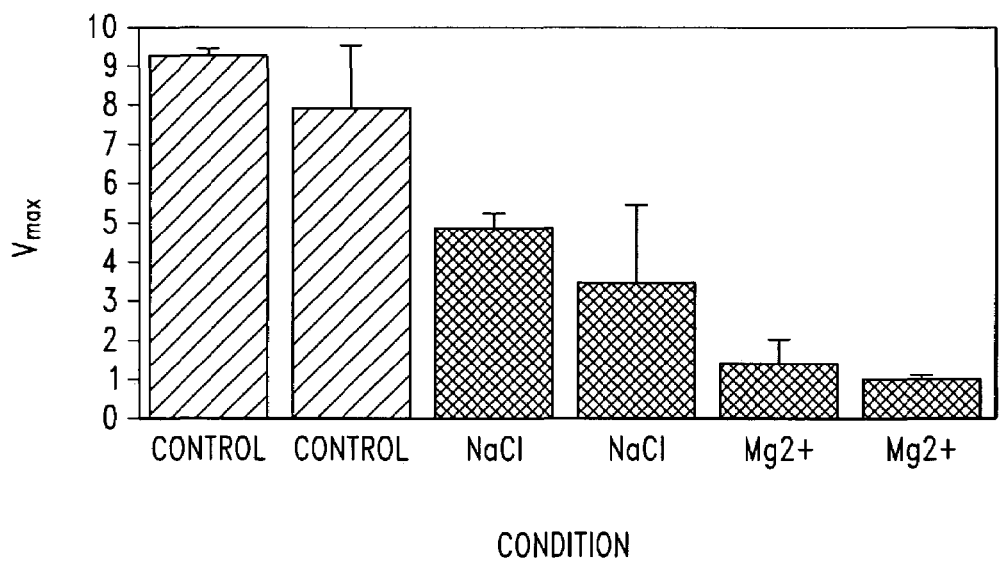
FIG. 10 is a graph showing treatment of bacteria with MBI 11B7CN in the presence of NaCl or $Mg^{2+}$.

Further delineation of the factors influencing membrane permeabilizing activity are tested. In an exemplary test, MBI 11B7CN is pre-incubated with isotonic HEPES/sucrose buffer containing either 150 mM sodium chloride (NaCl) or 5 mM magnesium ions ($Mg^{2+}$) and assayed as described earlier. In FIG. 10, a significant inhibition is observed with either solution, suggesting involvement of electrostatic interactions in the permeabilizing action of peptides.

Example 8

Erythtocyte Lysis by Indolicidin Analogues

A red blood cell (RBC) lysis assay is used to group peptides according to their ability to lyse RBC under standardized conditions compared with MBI 11CN and Gramicidin-S. Peptide samples and washed sheep RBC are prepared in isotonic saline with the final pH adjusted to between 6 and 7. Peptide samples and RBC suspension are mixed together to yield solutions that are 1% (v/v) RBC and 5, 50 or 500 μg/ml peptide. Assay mixtures are incubated for 1 hour at 37° C. with constant shaking, centrifuged, and the supernatant is measured for absorbance at 540 nm, which detects released hemoglobin. The percentage of released hemoglobin is determined by comparison with a set of known standards lysed in water. Each set of assays also includes MBI 11CN (500 μg/ml) and Gramicidin-S (5 μg/ml) as "low lysis" and "high lysis" controls, respectively.

MBI-11B7CN-HCl, MBI-11F3CN-HCl and MBI-11F4CN-HCl are tested using this procedure and the results are presented in Table 13 below.

TABLE 13

| Peptide | % lysis at 5 μg/ml | % lysis at 50 μg/ml | % lysis at 500 μg/ml |
|---|---|---|---|
| MBI 11B7CN-HCl | 4 | 13 | 46 |
| MBI 11F3CN-HCl | 1 | 6 | 17 |
| MBI 11F4CN-HCl | 4 | 32 | 38 |
| MBI 11CN-TFA | N/D | N/D | 9 |
| Gramicidin-S | 30 | N/D | N/D |

N/D = not done

Peptides that at 5 μg/ml lyse RBC to an equal or greater extent than Gramicidin-S, the "high lysis" control, are considered to be highly lytic. Peptides that at 500 μg/ml lyse RBC to an equal to or lesser extent than MBI 11CN, the "low lysis"

control, are considered to be non-lytic. The three analogues tested are all "moderately lytic" as they cause more lysis than MBI 11CN and less than Gramicidin-S. In addition one of the analogues, MBI-11F3CN-HCl, is significantly less lytic than the other two variants at all three concentrations tested.

Example 9

Production of Antibodies to Peptide Analogues

Multiple antigenic peptides (MAPs), which contain four or eight copies of the target peptide linked to a small non-immunogenic peptidyl core, are prepared as immunogens. Alternatively, the target peptide is conjugated to bovine serum albumin (BSA) or ovalbumin. For example, MBI 11CN and its seven amino acid N-terminal and C-terminal fragments are used as target peptide sequences. The immunogens are injected subcutaneously into rabbits using standard protocols (see, Harlow and Lane, *Antibodies: A Laboratory Mantial*, Cold Spring Harbor Laboratory Press, Cold Spring Harbor, N.Y., 1988). After repeated boosters (usually monthly), serum from a blood sample is tested in an ELISA against the target peptide. A positive result indicates the presence of antibodies and further tests determine the specificity of the antibody binding to the target peptide. Purified antibodies can then be isolated from this serum and used in ELISAs to selectively identify and measure the amount of the target peptide in research and clinical samples.

Example 10

Pharmacology of Peptide Analogues in Plasma and Blood

The in vitro lifetime of free peptide analogues in plasma and in blood is determined by measuring the amount of peptide present after set incubation times. Blood is collected from sheep, treated with an anticoagulant (not heparin) and, for plasma preparation, centrifuged to remove cells. Formulated peptide is added to either the plasma fraction or to whole blood and incubated. Following incubation, peptide is identified and quantified directly by reversed phase HPLC. Extraction is not required as the free peptide peak does not overlie any peaks from blood or plasma.

Figure 11:
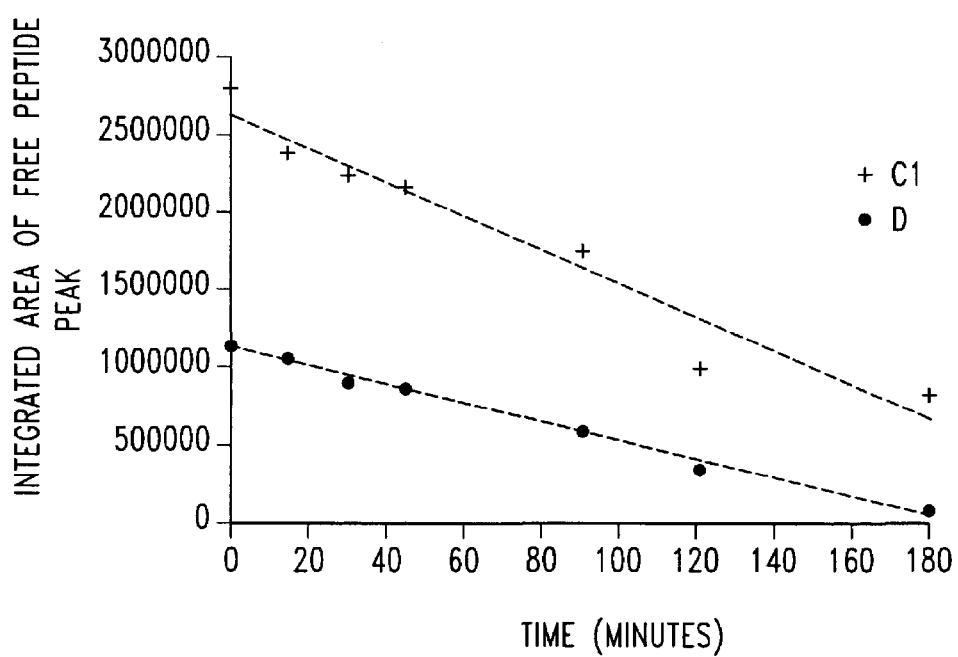
FIG. 11 is a graph presenting the in vitro amount of free MBI 11CN in plasma over time. Data is shown for peptide in formulation C1 and formulation D.

A 1 mg/mL solution of MBI 11CN in formulations C1 and D is added to freshly prepared sheep plasma at a final peptide concentration of 100 µg/mL and incubated at 37° C. At various times, aliquots of plasma are removed and analyzed for free peptide by reversed phase HPLC. From each chromatogram, the area of the peak corresponding to free peptide is integrated and plotted against time of incubation. As shown in FIG. 11, peptide levels diminish over time. Moreover, when administered in formulation D, up to 50% of the peptide is immediately released from formulation-peptide complex on addition to the blood. The decay curve for free peptide yields an apparent half-life in blood of 90 minutes for both formulation C1 and D. These results indicate that in sheep's blood MBI 11CN is relatively resistant to plasma peptidases and proteases. New peaks that appeared during incubation may be breakdown products of the peptide.

Figure 12:
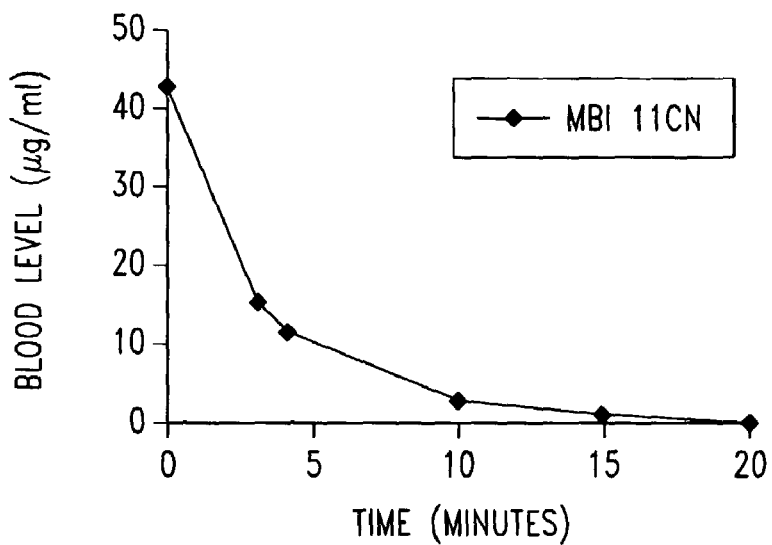
FIG. 12 is a graph presenting change in in vivo MBI 11CN levels in blood at various times after intravenous injection.

Peptide levels in plasma in vivo are measured after iv or ip administration of 80-100% of the maximum tolerated dose of peptide analogue in either formulation C1 or D. MBI 11CN in formulation C1 is injected intravenously into the tail vein of CD1 ICRBR strain mice. At various times post-injection, mice are anesthetized and blood is drawn by cardiac puncture. Blood from individual mice is centrifuged to separate plasma from cells. Plasma is then analyzed by reversed phase HPLC column. The resulting elution profiles are analyzed for free peptide content by UV absorbance at 280 nm, and these data are converted to concentrations in blood based upon a calibrated standard. Each data point represents the average blood level from two mice. In this assay, the detection limit is approximately 1 µg/ml, less than 3% of the dose administered The earliest time point at which peptide can be measured is three minutes following injection, thus, the maximum observed concentration (in µg/ml) is extrapolated back to time zero (FIG. 12). The projected initial concentration corresponds well to the expected concentration of between 35 and 45 µg/ml. Decay is rapid, however, and when the curve is fitted to the equation for exponential decay, free circulating peptide is calculated to have a half life of 2.1 minutes. Free circulating peptide was not detectable in the blood of mice that were injected with MBI 11CN in formulation D, suggesting that peptide is not released as quickly from the complex as in vitro.

In addition, MBI 11CN is also administered to CD1 ICRBR strain mice by a single ip injection at an efficacious dose level of 40 mg/kg. Peptide is administered in both formulations C1 and D to determine if peptide complexation has any effect on blood levels. At various times post injection, mice are anesthetized and blood is drawn by cardiac puncture. Blood is collected and analyzed as for the iv injection.

Figure 13:
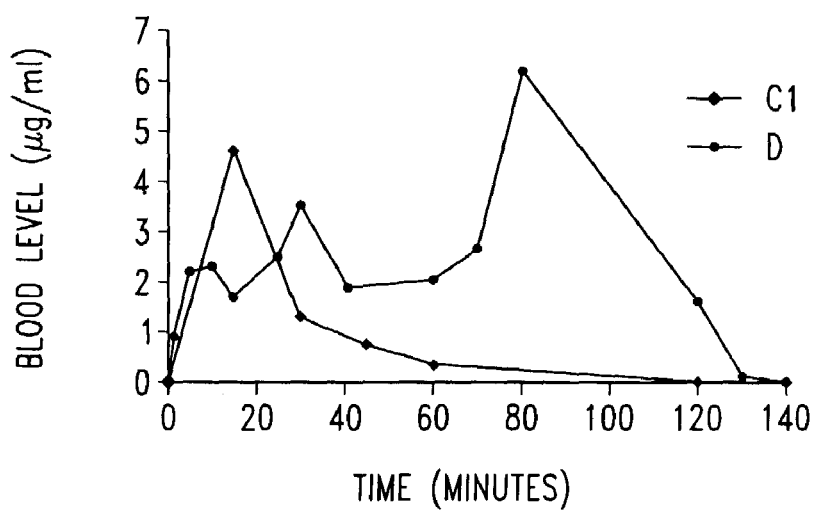
FIG. 13 is a graph presenting change in in vivo MBI 11CN levels in plasma at various times after intraperitoneal injection.

MBI 11CN administered by this route demonstrated a quite different pharmacologic profile (FIG. 13). In formulation C1, peptide entered the blood stream quickly, with a peak concentration of nearly 5 µg/ml after 15 minutes, which declined to non-detectable levels after 60 minutes. In contrast, peptide in formulation D is present at a level above 2 µg/ml for approximately two hours. Therefore, formulation affects entry into, and maintenance of levels of peptide in the blood.

Example 11

Toxicity of Peptide Analogues In vivo

The acute, single dose toxicity of various indolicidin analogues is tested in Swiss CD1 mice using various routes of administration. In order to determine the inherent toxicities of the peptide analogues in the absence of any formulation/delivery vehicle effects, the peptides are all administered in isotonic saline with the final pH between 6 and 7.

Intraperitoneal route. Groups of 6 mice are injected with peptide doses of between 80 and 5 mg/kg in 500 µl dose volumes. After peptide administration, the mice are observed for a period of 5 days, at which time the dose causing 50% mortality ($LD_{50}$), the dose causing 90-100% mortality ($LD_{90-100}$) and maximum tolerated dose (MTD) levels are determined. The $LD_{50}$ values are calculated using the method of Reed and Muench (*J. of Amer. Hyg.* 27: 493-497, 1938). The results presented in Table 14 show that the $LD_{50}$ values for MBI 11CN and analogues range from 21 to 52 mg/kg.

TABLE 14

| Peptide | $LD_{50}$ | $LD_{90-100}$ | MTD |
|---|---|---|---|
| MBI 11CN | 34 mg/kg | 40 mg/kg | 20 mg/kg |
| MBI 11B7CN | 52 mg/kg | >80 mg/kg | 30 mg/kg |
| MBI 11E3CN | 21 mg/kg | 40 mg/kg | <20 mg/kg |
| MBI 11F3CN | 52 mg/kg | 80 mg/kg | 20 mg/kg |

Intravenous route. Groups of 6 mice are injected with peptide doses of 20, 16, 12, 8, 4 and 0 mg/kg in 100 μl volumes (4 ml/kg). After administration, the mice are observed for a period of 5 days, at which time the $LD_{50}$, $LD_{90-100}$ and MTD levels are determined. The results from the IV toxicity testing of MBI 11CN and three analogues are shown in Table 15. The $LD_{50}$, $LD_{90-100}$ and MTD values range from 5.8 to 15 mg/kg, 8 to 20 mg/kg and <4 to 12 mg/kg respectively.

TABLE 15

| Peptide | $LD_{50}$ | $LD_{90-100}$ | MTD |
|---|---|---|---|
| MBI 11CN HCl | 5.8 mg/kg | 8.0 mg/kg | <4 mg/kg |
| MBI 11B7CN HCl | 7.5 mg/kg | 16 mg/kg | 4 mg/kg |
| MBI 11F3CN HCl | 10 mg/kg | 12 mg/kg | 8 mg/kg |
| MBI 11F4CN HCl | 15 mg/kg | 20 mg/kg | 12 mg/kg |

Subcutaneous route. The toxicity of MBI 11CN is also determined after subcutaneous (SC) administration. For SC toxicity testing, groups of 6 mice are injected with peptide doses of 128, 96, 64, 32 and 0 mg/kg in 300 μL dose volumes (12 mL/kg). After administration, the mice are observed for a period of 5 days. None of the animals died at any of the dose levels within the 5 day observation period. Therefore, the $LD_{50}$, $LD_{90-100}$ and MTD are all taken to be greater than 128 mg/kg. Mice receiving higher dose levels showed symptoms similar to those seen after IV injection suggesting that peptide entered the systemic circulation. These symptoms are reversible, disappearing in all mice by the second day of observations.

The single dose toxicity of MBI 10CN and MBI 11CN in different formulations is also examined in outbred ICR mice (Table 16). Intraperitoneal injection (groups of 2 mice) of MBI 10CN in formulation D show no toxicity up to 29 mg/kg and under the same conditions MBI 11CN show no toxicity up to 40 mg/kg.

Intravenous injection (groups of 10 mice) of MBI 10CN in formulation D show a maximum tolerated dose (MTD) of 5.6 mg/kg (Table 16). Injection of 11 mg/kg gave 40% toxicity and 22 mg/kg result in 100% toxicity. Intravenous injection of MBI 11CN in formulation C (lyophilized) show a MTD of 3.0 mg/kg. Injection at 6.1 mg/kg result in 10% toxicity and at 12 mg/kg 100% toxicity.

TABLE 16

| Peptide | Route | # Animals | Formulation | MTD (mg/kg) |
|---|---|---|---|---|
| MBI 10CN | ip | 2 | formulation D | >29 |
| MBI 11CN | ip | 2 | formulation D | >40 |
| MBI 10CN | iv | 10 | formulation D | 5.6 |
| MBI 11CN | iv | 10 | formulation C (lyophilized) | 3.0 |

These results are obtained using peptide/buffer solutions that are lyophilized after preparation and reconstituted with water. If the peptide solution is not lyophilized before injection, but used immediately after preparation, an increase in toxicity is seen, and the maximum tolerated dose can decrease by up to four-fold. For example, an intravenous injection of MBI 11CN as a non-lyophilized solution, formulation C1, at 1.5 mg/kg results in 20% toxicity and at 3.0 mg/kg gave 100% toxicity. HPLC analyses of the non-lyophilized and lyophilized formulations indicate that the MBI 11CN forms a complex with polysorbate, and this complexation of the peptide reduces its toxicity in mice.

In addition, mice are multiply injected by an intravenous route with MBI 11CN (Table 17). In one representative experiment, peptide administered in 10 injections of 0.84 mg/kg at 5 minute intervals is not lethal. However, two injections of peptide at 4.1 mg/kg administered with a 10 minute interval results in 60% mortality.

TABLE 17

| Peptide | Route | Formulation | Dose Level* | # Injections | Time Interval | Result |
|---|---|---|---|---|---|---|
| MBI 11CN | iv | formulation D | 0.84 | 10 | 5 min | no mortality |
| MBI 11CN | iv | formulation D | 4.1 | 2 | 10 min | 66% mortality |

*(mg/kg)

To assess the impact of dosing mice with peptide analogue, a series of histopathology investigations can be carried out. Groups of mice are administered analogue at dose levels that are either at, or below the MTD, or above the MTD, a lethal dose. Multiple injections may be used to mimic possible treatment regimes. Groups of control mice are not injected or injected with buffer only.

Following injection, mice are sacrificed at specified times and their organs immediately placed in a 10% balanced formalin solution. Mice that die as a result of the toxic effects of the analogue also have their organs preserved immediately. Tissue samples are taken and prepared as stained microsections on slides which are then examined microscopically. Damage to tissues is assessed and this information can be used to develop improved analogues, improved methods of administration or improved dosing regimes.

Example 12

In vivo Efficacy of Peptide Analogues

Analogues are tested for their ability to rescue mice from lethal bacterial infections. The animal model used is an intraperitoneal (ip) inoculation of mice with $10^6$-$10^8$ Gram-positive organisms with subsequent administration of peptide. The three pathogens investigated, methicillin-sensitive *S. aureus* (MSSA), methicillin-resistant *S. aureus* (MRSA), or *S. epidermidis* are injected ip into mice. For untreated mice, death occurs within 12-18 hours with MSSA and *S. epidermis* and within 6-10 hours with MRSA.

Peptide is administered by two routes, intraperitoneally, at one hour post-infection, or intravenously, with single or multiple doses given at various times pre- and post-infection.

MSSA infection. In a typical protocol, groups of 10 mice are infected intraperitoneally with a $LD_{90-100}$ dose ($5.2 \times 10^6$ CFU/mouse) of MSSA (Smith, ATCC #19640) injected in brain-heart infusion containing 5% mucin. This strain of *S. aureus* is not resistant to any common antibiotics. At 60 minutes post-infection, MBI 10CN or MBI 11CN, in formulation D, is injected intraperitoneally at the stated dose levels. An injection of formulation alone serves as a negative control and administration of ampicillin serves as a positive control. The survival of the mice is monitored at 1, 2, 3 and 4 hrs post-infection and twice daily thereafter for a total of 8 days.

Figure 14:
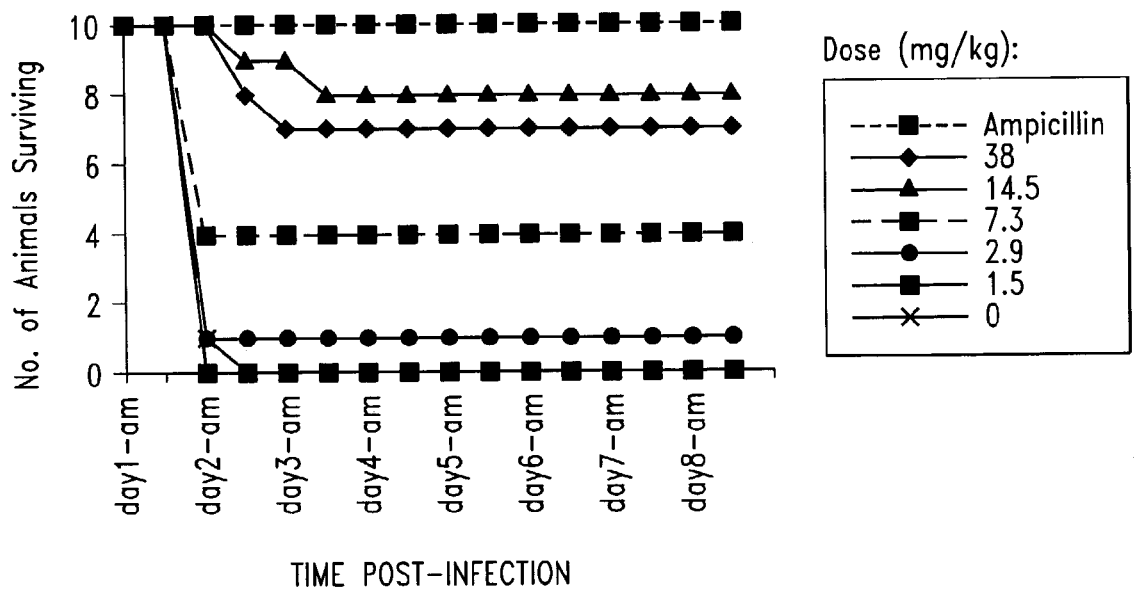
FIG. 14 is a graph showing the number of animals surviving an MSSA infection after intraperitoneal injection of MBI 10CN, ampicillin, or vehicle.
Figure 15:
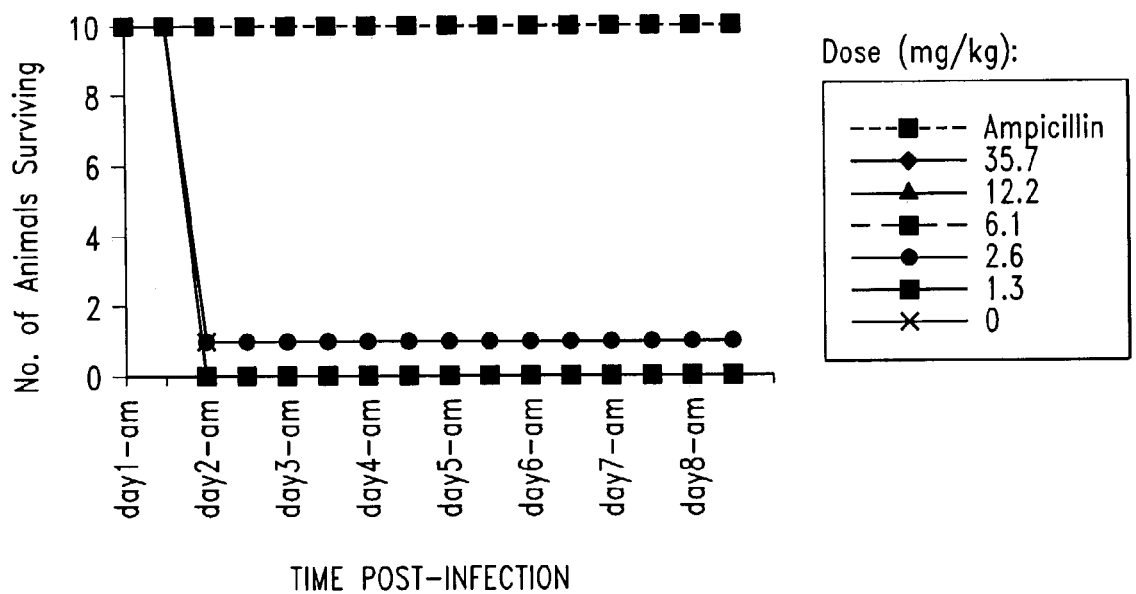
FIG. 15 is a graph showing the number of animals surviving an MSSA infection after intraperitoneal injection of MBI 11CN, ampicillin, or vehicle.
Figure 16:
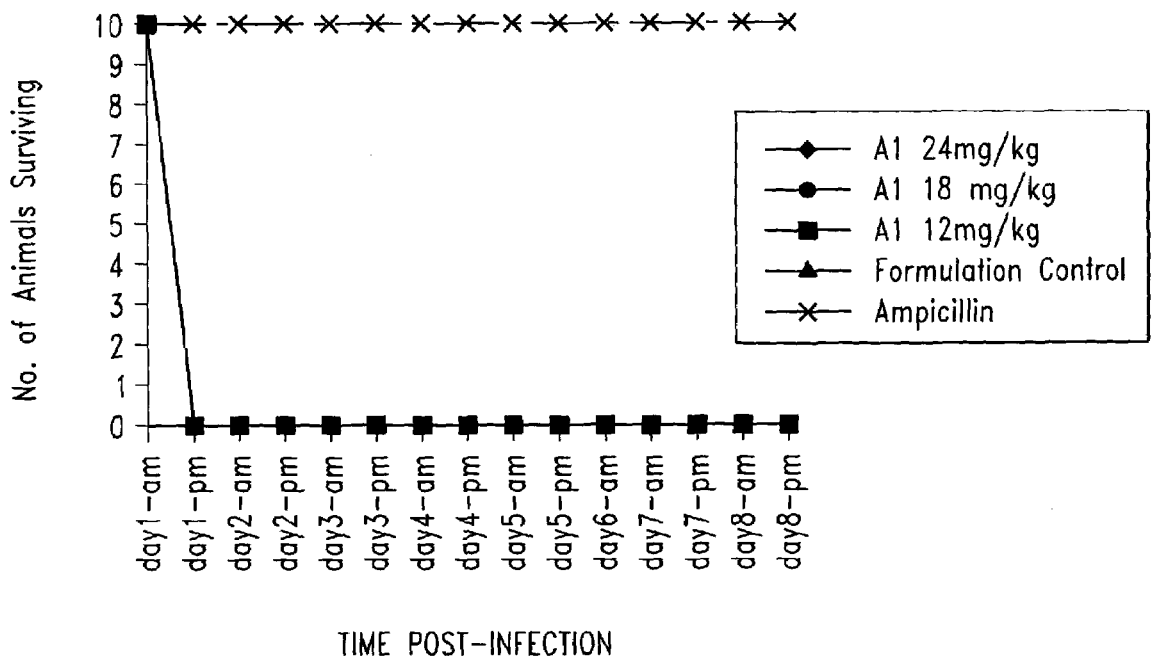
FIG. 16 is a graph showing the results of in vivo testing of MBI-11A1CN against S. aureus (Smith). Formulated peptide at various concentrations is administered by ip injection one hour after infection with S. aureus (Smith) by ip injection.
Figure 17:
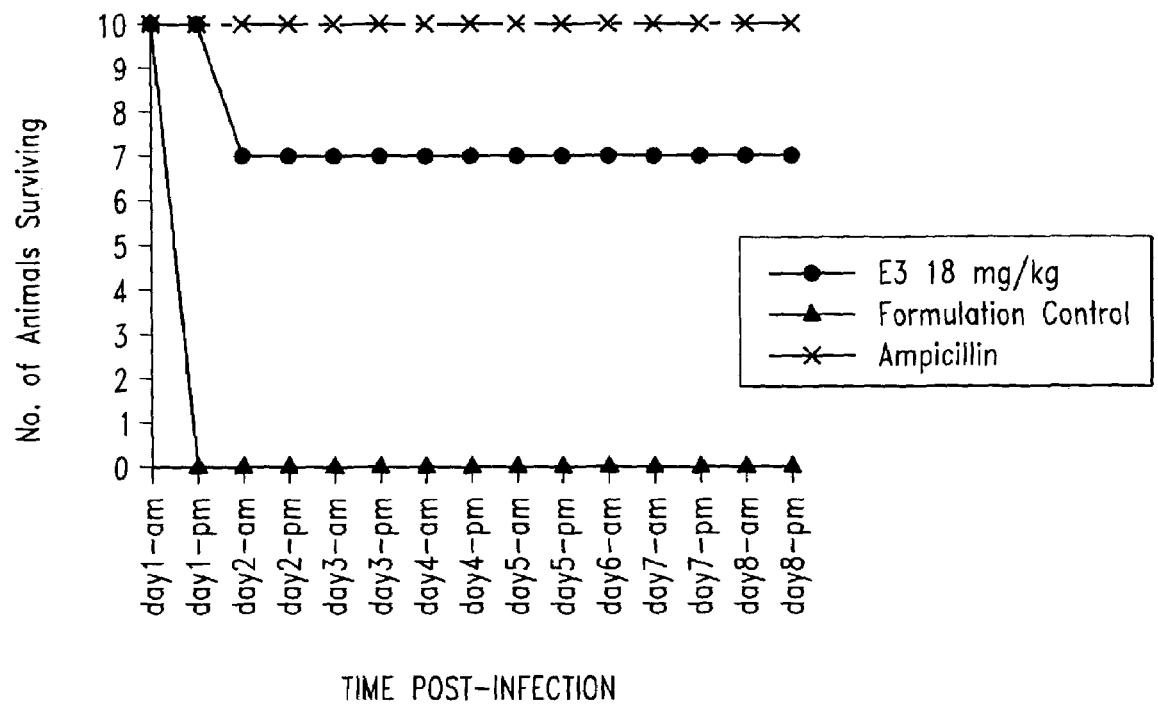
FIG. 17 is a graph showing the results of in vivo testing of MBI-11E3CN against S. aureus (Smith). Formulated peptide at various concentrations is administered by ip injection one hour after infection with S. aureus (Smith) by ip injection.
Figure 18:
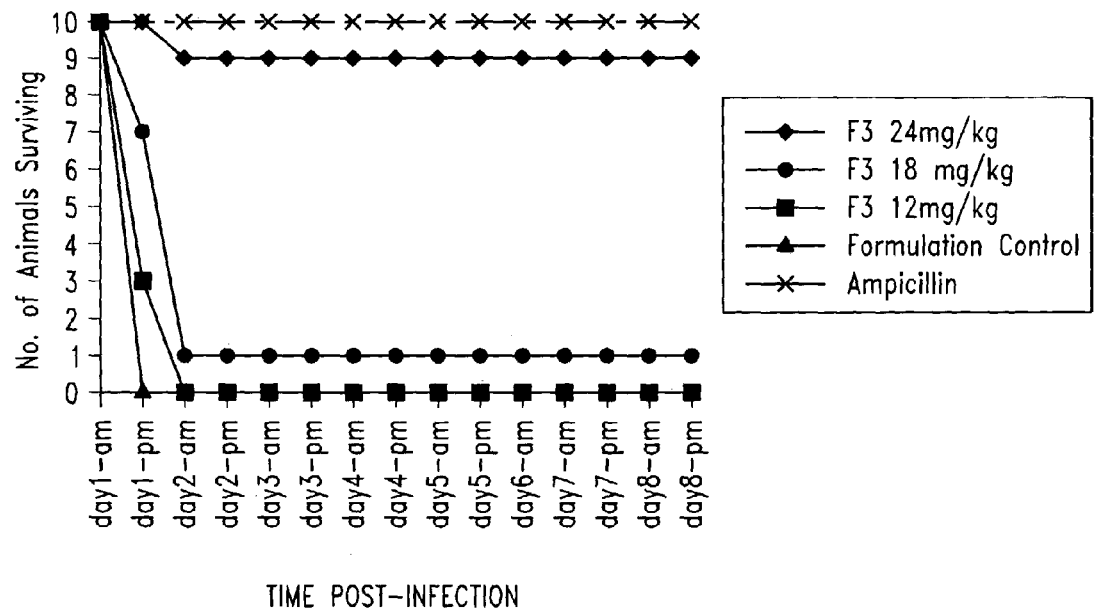
FIG. 18 is a graph showing the results of in vivo testing of: MBI-11F3CN against S. aureus (Smith). Formulated peptide at various concentrations is administered by ip injection one hour after infection with S. aureus (Smith) by ip injection.
Figure 19:
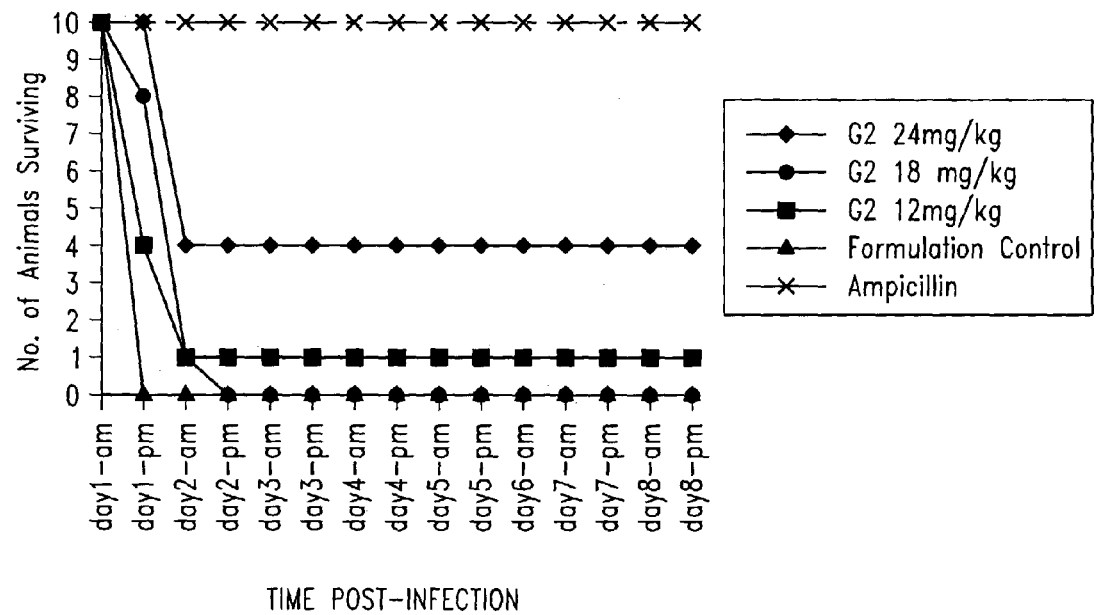
FIG. 19 is a graph showing the results of in vivo testing of MBI-11G2CN against S. aureus (Smith). Formulated peptide at various concentrations is administered by ip injection one hour after infection with S. aureus (Smith) by ip injection.
Figure 20:
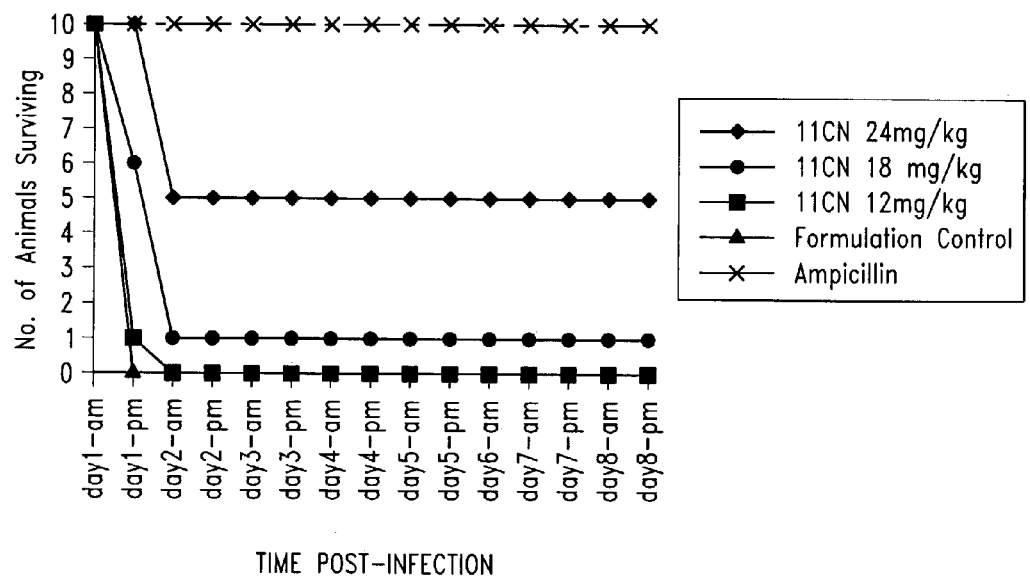
FIG. 20 is a graph showing the results of in viva testing of MBI-11CN against S. aureus (Smith). Formulated peptide at various concentrations is administered by ip injection one hour after infection with S. aureus (Smith) by ip injection.
Figure 21:
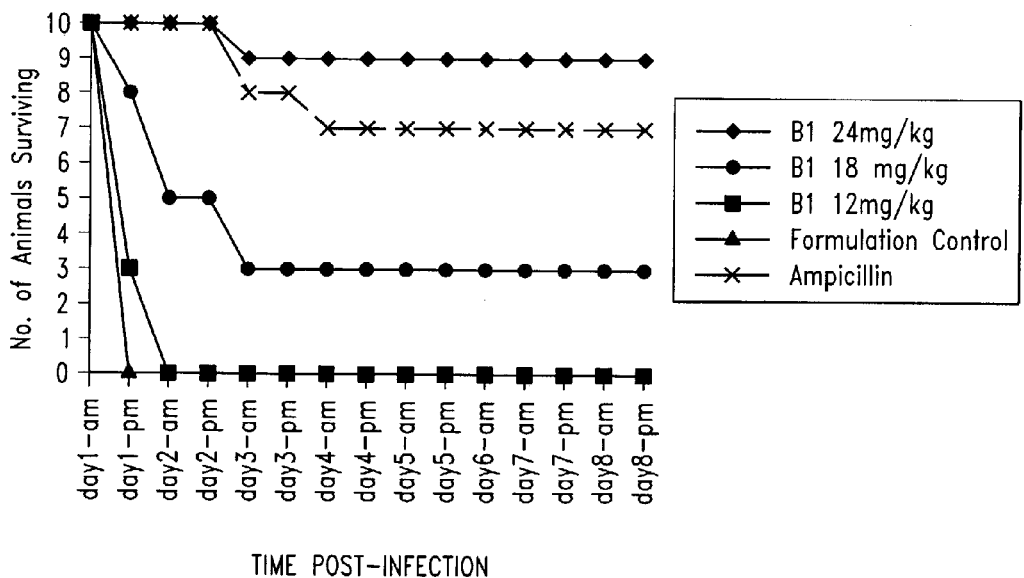
FIG. 21 is a graph showing the results of in vivo testing of MBI-11B1CN against S. aureus (Smith). Formulated peptide at various concentrations is administered by ip injection one hour after infection with S. aureus (Smith) by ip injection.
Figure 22:
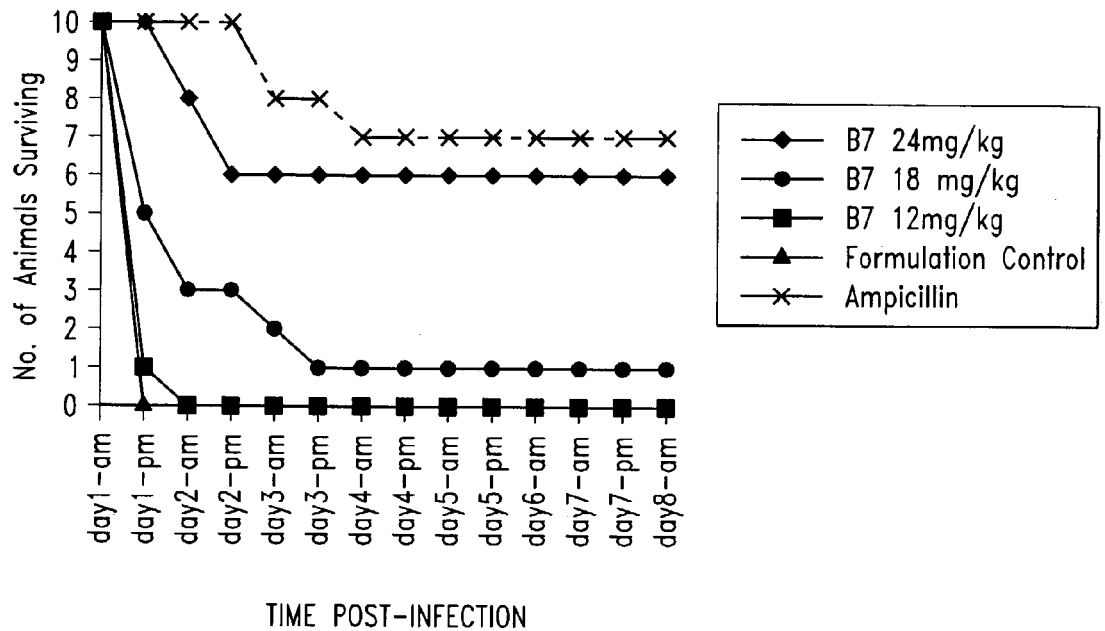
FIG. 22 is a graph showing the results of in vivo testing of MBI-11B7CN against S. aureus (Smith). Formulated peptide at various concentrations is administered by ip injection one hour after infection with S. aureus (Smith) by ip injection.
Figure 23:
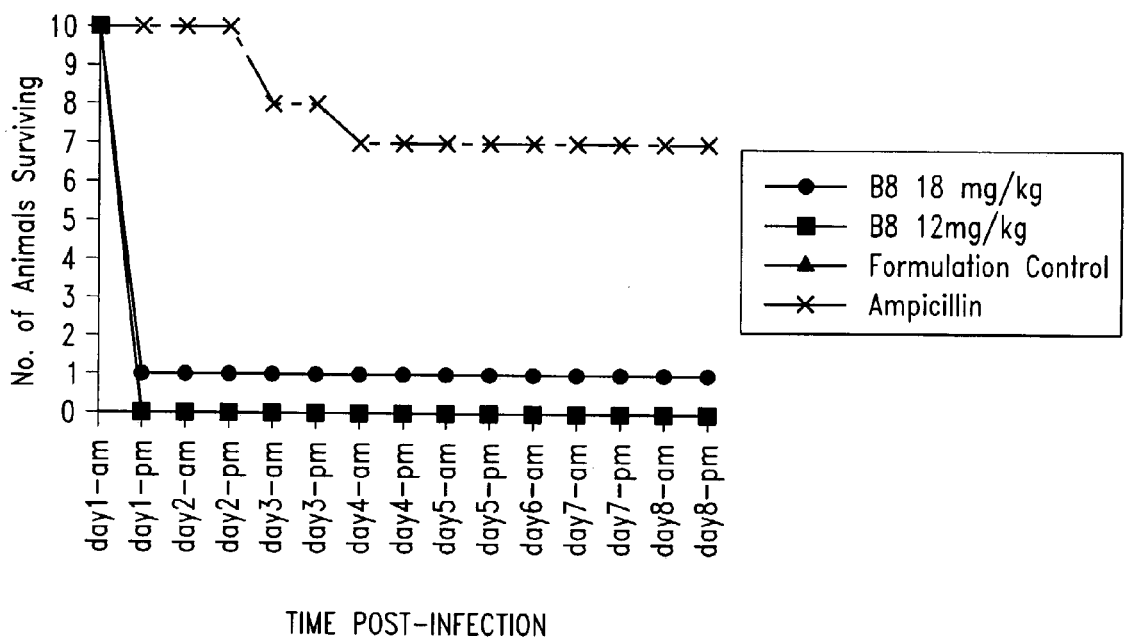
FIG. 23 is a graph showing the results of in vivo testing of MBI-11B8CN against S. aureus (Smith). Formulated peptide at various concentrations is administered by ip injection one hour after infection with S. aureus (Smith) by ip injection.
Figure 24:
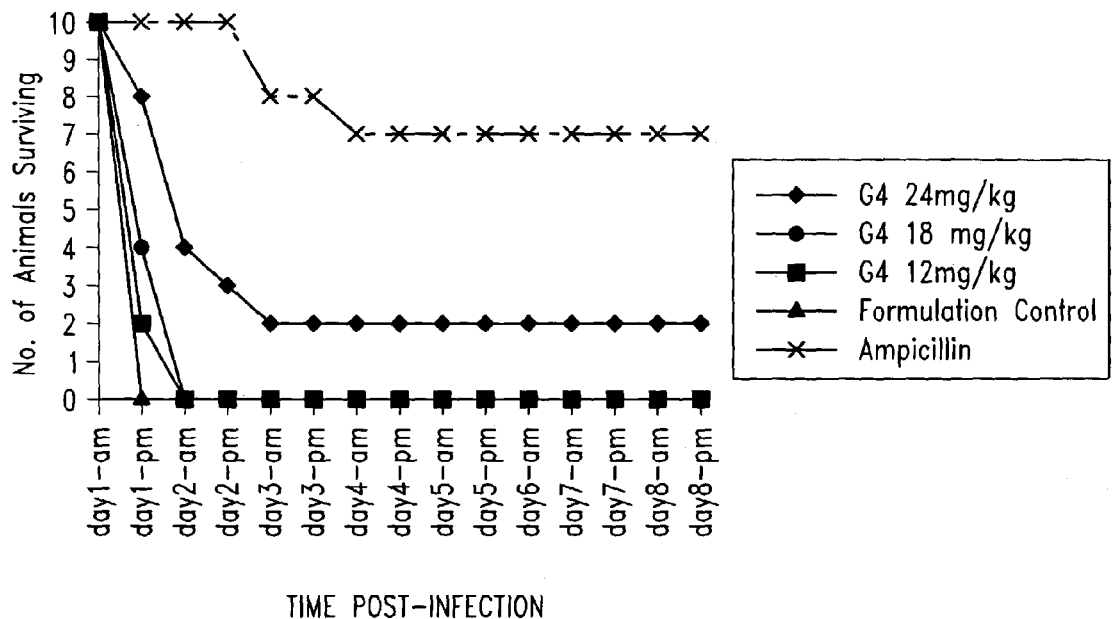
FIG. 24 is a graph showing the results of in vivo testing of MBI-11G4CN against S. aureus (Smith). Formulated peptide at various concentrations is administered by ip injection one hour after infection with S. aureus (Smith) by ip injection.

As shown in FIG. 14, MBI 10CN is maximally active against MSSA (70-80% survival) at doses of 14.5 to 38.0 mg/kg, although 100% survival is not achieved. Below 14.5 mg/kg, there is clear dose-dependent survival. At these lower dose levels, there appears to be an animal-dependent threshold, as the mice either die by day 2 or survive for the full eight day period. As seen in FIG. 15, MBI 11CN, on the other hand, rescued 100% of the mice from MSSA infection at a dose level of 35.7 mg/kg, and was therefore as effective as ampicillin. There was little or no activity at any of the lower dose levels, which indicates that a minimum bloodstream peptide level must be achieved during the time that bacteria are a danger to the host.

As shown above, blood levels of MBI 11CN can be sustained at a level of greater than 2 μ/ml for a two hour period inferring that this is higher than the minimum level.

Additionally, eight variants based on the sequence of MBI 11CN are tested against MSSA using the experimental system described above. Peptides prepared in formulation D are administered at dose levels ranging from 12 to 24 mg/kg and the survival of the infected mice is monitored for eight days (FIGS. 16-24). The percentage survival at the end of the observation period for each variant is summarized in Table 18. As shown in the table, several of the variants showed efficacy greater than or equal to MBI 11CN under these conditions.

TABLE 18

| % Survival | 24 mg/kg | 18 mg/kg | 12 mg/kg |
|---|---|---|---|
| 100 | | | |
| 90 | 11B1CN, 11F3CN | | |
| 80 | | | |
| 70 | | 11E3CN | |
| 60 | 11B7CN | | |
| 50 | 11CN | | |
| 40 | 11G2CN | | |
| 30 | | 11B1CN | |
| 20 | 11G4CN | | |
| 10 | | 11CN, 11B7CN, 11B8CN, 11F3CN | 11G2CN |
| 0 | 11A1CN | 11A1CN, 11G2CN, 11G4CN | 11CN, 11A1CN, 11B1CN, 11B7CN, 11B8CN, 11F3CN, 11G4CN |

*S. epidermidis* infection. Peptide analogues generally have lower MIC values against *S. epidermidis* in vitro, therefore, lower blood peptide levels might be more effective against infection.

In a typical protocol, groups of 10 mice are injected intraperitoneally with an $LD_{90-100}$ dose ($2.0\times10^8$ CFU/mouse) of *S. epidermidis* (ATCC #12228) in brain-heart infusion broth containing 5% mucin. This strain of *S. epidermidis* is 90% lethal after 5 days. At 15 mins and 60 mins post-infection, various doses of MBI 11CN in formulation D are injected intravenously via the tail vein. An injection of formulation only serves as the negative control and injection of gentamicin serves as the positive control; both are injected at 60 minutes post-infection. The survival of the mice is monitored at 1, 2, 3, 4, 6 and 8 hrs post-infection and twice daily thereafter for a total of 8 days.

Figure 25A:
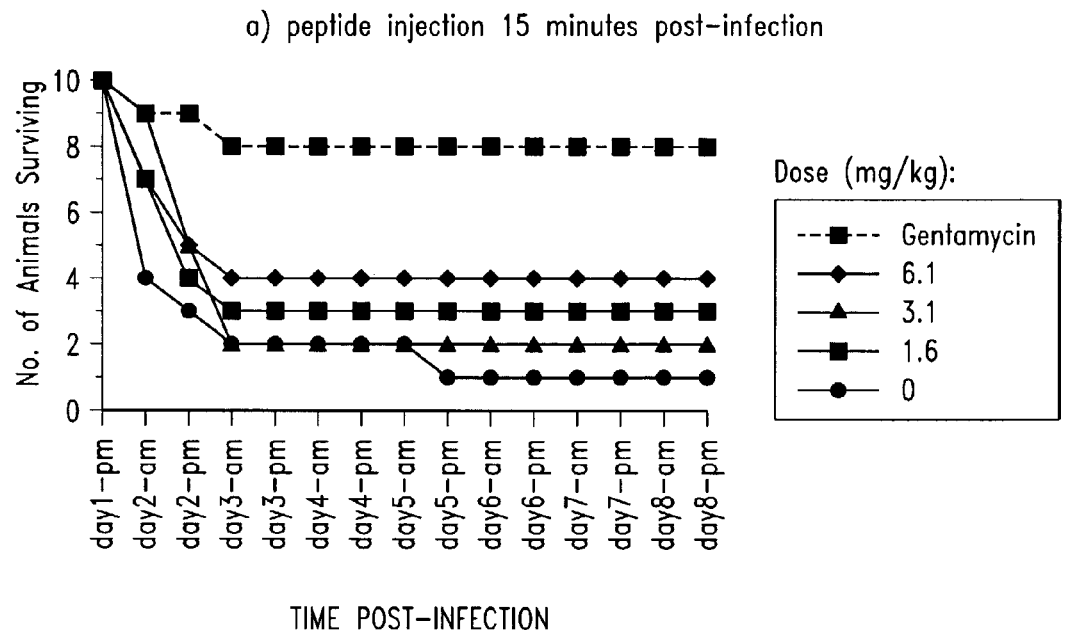
FIGS. 25A and B display a graph showing the number of animals surviving an S. epidermidis infection after intravenous injection of MBI 10CN, gentamicin, or vehicle. Panel A, i.v. injection 15 min post-infection; panel B, i.v. injection 60 min post-infection.
Figure 25B:
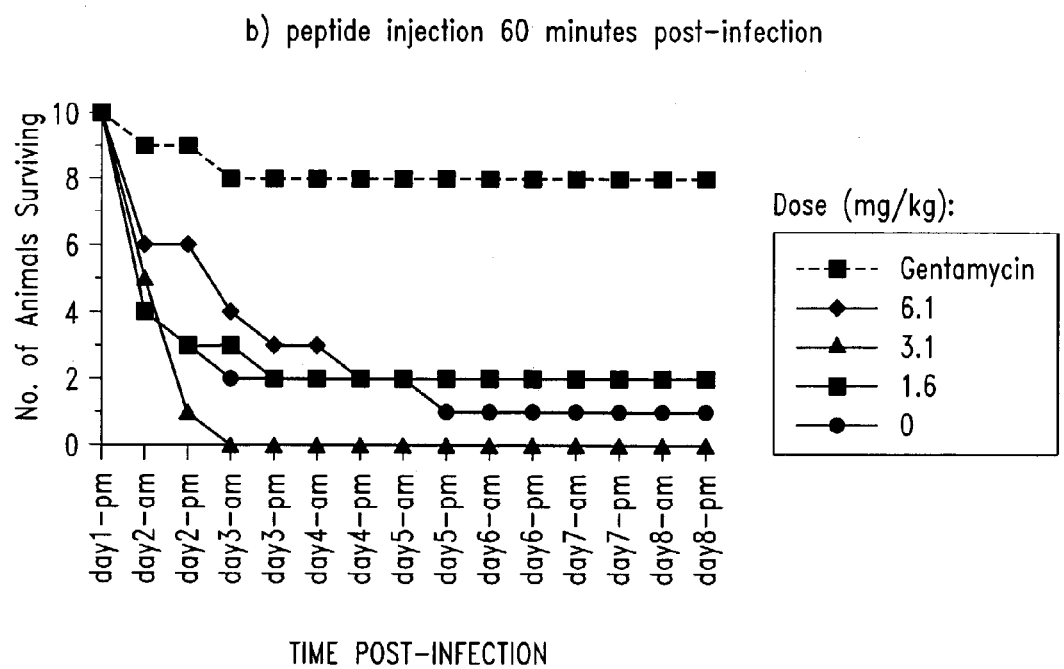

As shown in FIGS. 25A and 25B, MBI 11CN prolongs the survival of the mice. Efficacy is observed at all three dose levels with treatment 15 minutes post-infection, however, there is less activity at 30 minutes post-infection and no significant effect at 60 minutes post-infection. Time of administration appears to be important in this model system, with a single injection of 6.1 mg/kg 15 minutes post-infection giving the best survival rate.

MRSA infection. MRSA infection, while lethal in a short period of time, requires a much higher bacterial load than MSSA. In a typical protocol, groups of 10 mice are injected intraperitoneally with a $LD_{90-100}$ dose ($4.2\times10^7$ CFU/mouse) of MRSA (ATCC #33591) in brain-heart infusion containing 5% mucin. The treatment protocols are as follows, with the treatment times relative to the time of infection:

| | |
|---|---|
| 0 mg/kg | Formulation D alone (negative control), injected at 0 mins |
| 5 mg/kg | Three 5.5 mg/kg injections at −5, +55, and +115 mins |
| 1 mg/kg (2 hr) | Five 1.1 mg/kg injections at −5, +55, +115, +175 and +235 mins |
| 1 mg/kg (20 min) | Five 1.1 mg/kg injections at −10, −5, 0, +5, and +10 mins |
| Vancomycin | (positive control) injected at 0 mins |

Figure 26:
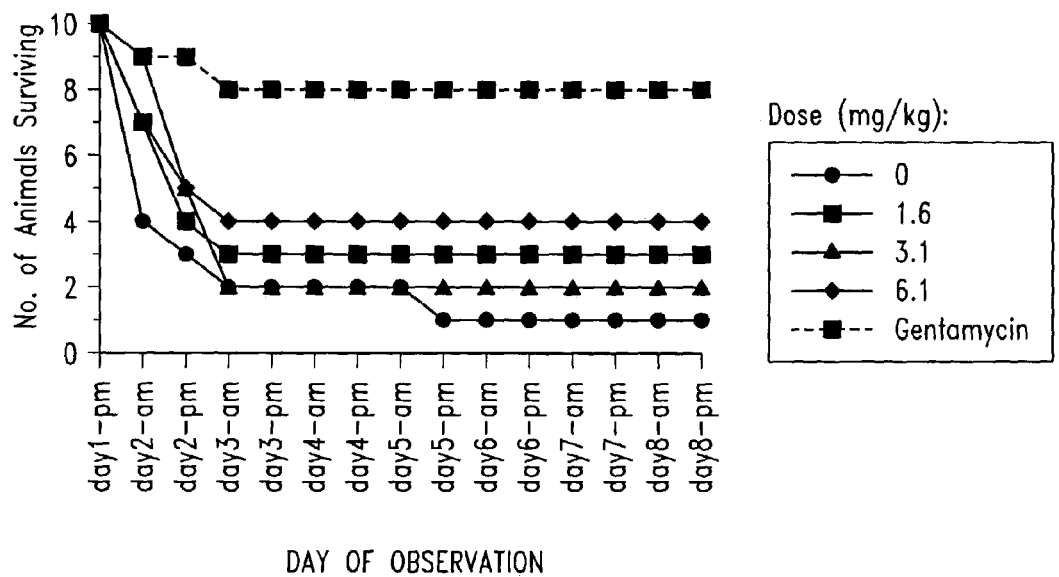
FIG. 26 is a graph showing the number of animals surviving an MRSA infection mice after intravenous injection of MBI 11CN, gentamicin, or vehicle.

MBI 11CN is injected intravenously in the tail vein in formulation D. Survival of mice is recorded at 1, 2, 3, 4, 6, 8, 10, 12, 20, 24 and 30 hrs post-infection and twice daily thereafter for a total of 8 days. There was no change in the number of surviving mice after 24 hrs (FIG. 26).

The 1 mg/kg (20 min) treatment protocol, with injections 5 minutes apart centered on the infection time, delayed the death of the mice to a significant extent with one survivor remaining at the end of the study. The results presented in Table 19 suggest that a sufficiently high level of MBI 11CN maintained over a longer time period would increase the number of mice surviving. The 5 mg/kg and 1 mg/kg (2 hr) results, where there is no improvement in survivability over the negative control, indicates that injections 1 hour apart, even at a higher level, are not effective against MRSA.

TABLE 19

| Time of Observation | Percentage of Animals Surviving | |
|---|---|---|
| (Hours post-infection) | No Treatment | Treatment |
| 6 | 50% | 70% |
| 8 | 0 | 40% |
| 10 | 0 | 30% |
| 12 | 0 | 20% |

Example 13

Activation of Polysorbate 80 by Ultraviolet Light

A solution of 2% (w/w) polysorbate 80 is prepared in water and placed in a suitable reaction vessel, such as a quartz cell. Other containers that are UV translucent or even opaque can be used if provision is made for a clear light path or an extended reaction time. In addition, the vessel should allow the exchange of air but minimize evaporation.

The solution is irradiated with ultraviolet light using a lamp emitting at 254 nm. Irradiation can also be performed using a lamp emitting at 302 nm. The activation is complete in 1-14 days depending upon the container, the depth of the solution, and air exchange rate. The reaction is monitored by a reversed-phased HPLC assay, which measures the formation of APS-modified MBI 11CN when the light-activated polysorbate is reacted with MBI 11CN.

Figure 27A:
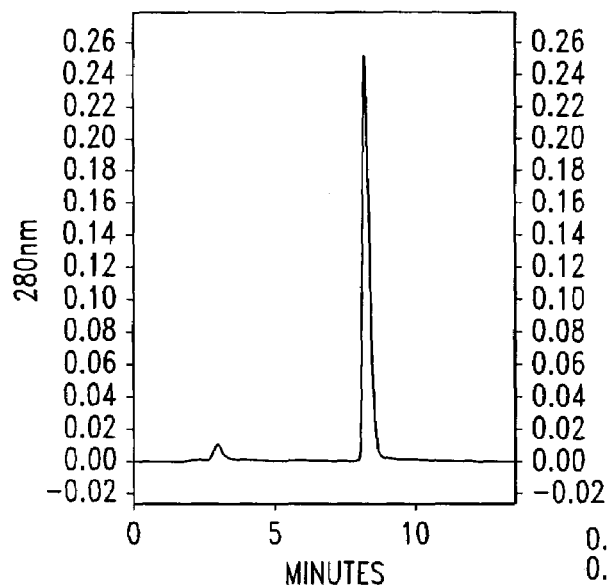
FIG. 27 presents RP-HPLC traces analyzing samples for APS-peptide formation after treatment of activated polysorbate with a reducing agent. APS-MBI-11CN peptides are formed via lyophilization in 200 mM acetic acid-NaOH, pH 4.6, 1 mg/ml MBI 11CN, and 0.5% activated polysorbate 80. The stock solution of activated 2.0% polysorbate is treated with (a) no reducing agent, (b) 150 mM 2-mercaptoethanol, or (c) 150 mM sodium borohydride for 1 hour immediately before use.
Figure 27B:
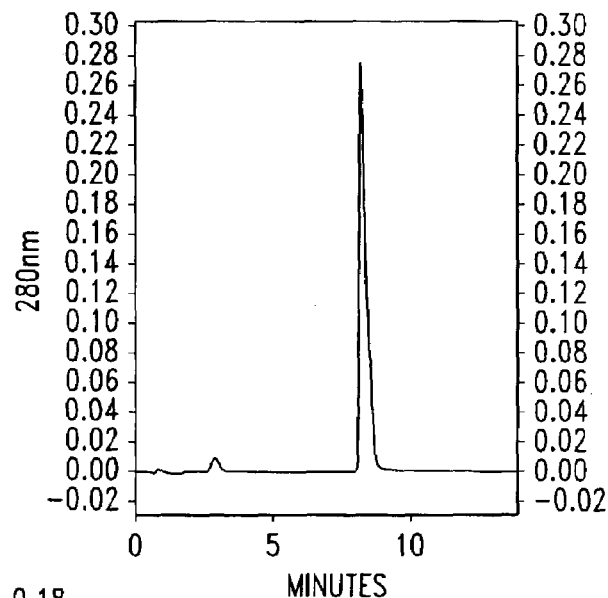
Figure 27C:
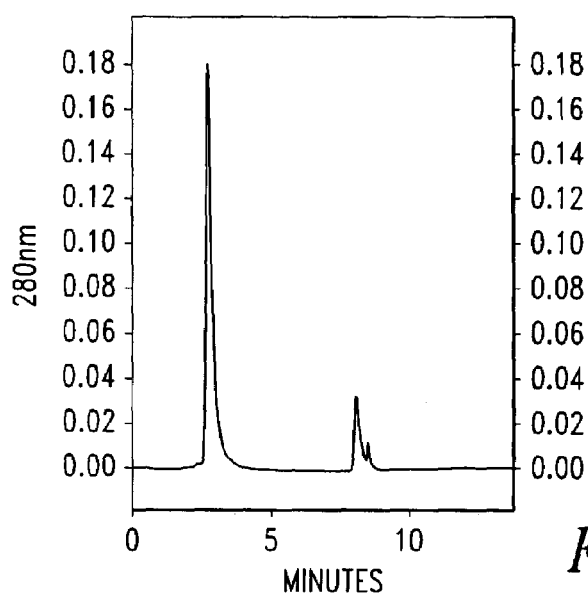

Some properties of activated polysorbate are determined. Because peroxides are a known by-product of exposing ethers to UV light, peroxide formation is examined through the effect of reducing agents on the activated polysorbate. As seen in FIG. 27A, activated polysorbate readily reacts with MBI 11CN. Pre-treatment with 2-mercaptoethanol (FIG. 27B), a mild reducing agent, eliminates detectable peroxides, but does not cause a loss of conjugate forming ability. Treatment with sodium borohydride (FIG. 27C), eliminates peroxides and eventually eliminates the ability of activated polysorbate to modify peptides. Hydrolysis of the borohydride in water raises the pH and produces borate as a hydrolysis product. However, neither a pH change nor borate are responsible.

These data indicate that peroxides are not involved in the modification of peptides by activated polysorbate. Sodium borohydride should not affect epoxides or esters in aqueous media, suggesting that the reactive group is an aldehyde or ketone. The presence of aldehydes in the activated polysorbate is confirmed by using a formaldehyde test, which is specific for aldehydes including aldehydes other than formaldehyde.

Furthermore, activated polysorbate is treated with 2,4-dinitrophenylhydrazine (DNPH) in an attempt to capture the reactive species. Three DNPH-tagged components are purified and analyzed by mass spectroscopy. These components are polysorbate-derived with molecular weights between 1000 and 1400. This indicates that low molecular weight aldehydes, such as formaldehyde or acetaldehyde, are involved.

Example 14

Formation of APS-Modified Peptides

APS-modified peptides are prepared either in solid phase or liquid phase. For solid phase preparation, 0.25 ml of 4 mg/ml of MBI 11CN is added to 0.5 ml of 0.4 M Acetic acid-NaOH pH 4.6 followed by addition of 0.25 ml of UV-activated polysorbate. The reaction mix is frozen by placing it in a −80° C. freezer. After freezing, the reaction mix is lyophilized overnight.

Figure 28:
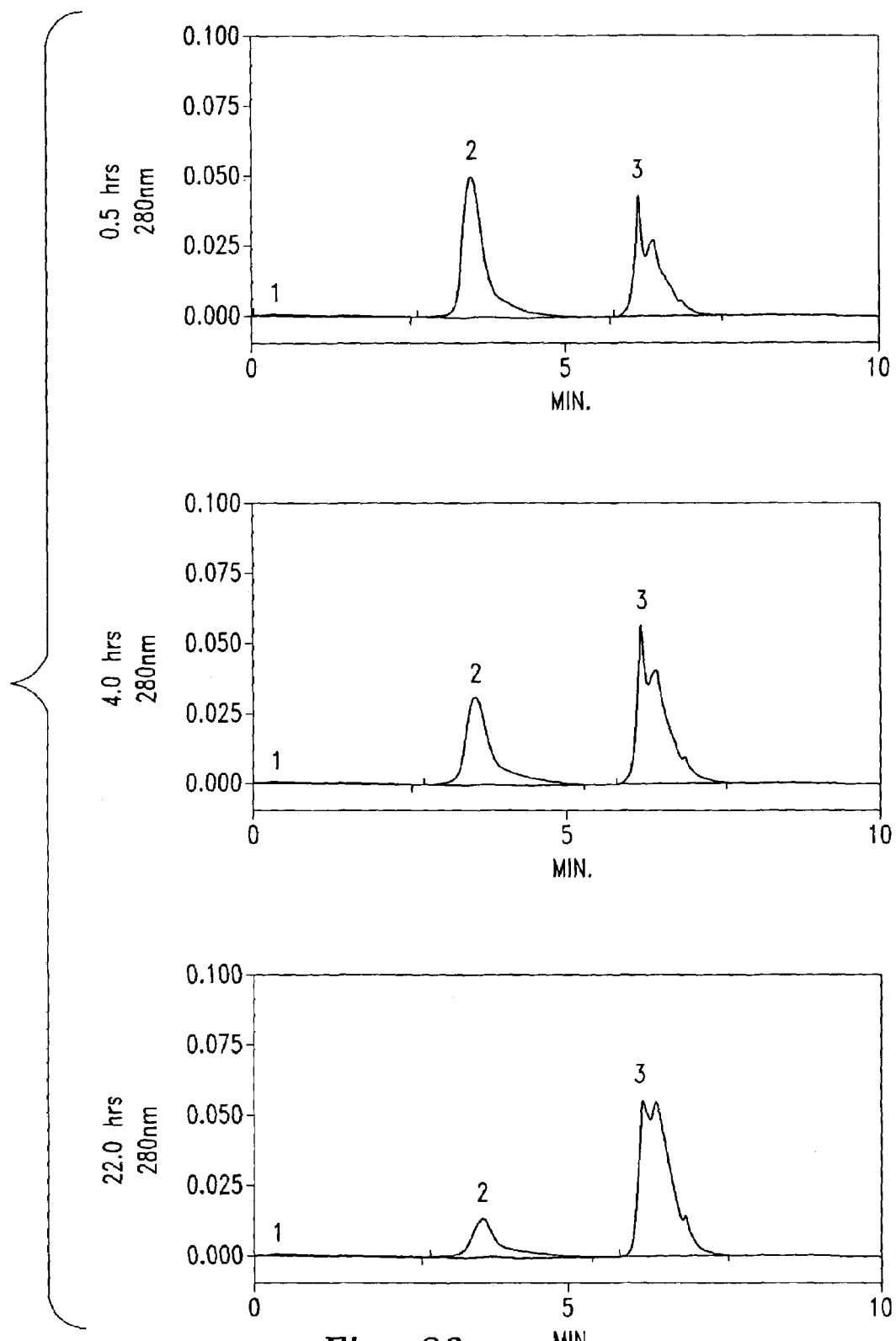
FIG. 28 presents RP-HPLC traces monitoring the formation of APS-MBI 11CN over time in aqueous solution. The reaction occurs in 200 mM sodium carbonate buffer pH 10.0, 1 mg/ml MBI 11CN, 0.5% activated polysorbate 80. Aliquots are removed from the reaction vessel at the indicated time points and immediately analyzed by RP-HPLC.

For preparing the conjugates in an aqueous phase, a sample of UV activated polysorbate 80 is first adjusted to a pH of 7.5 by the addition of 0.1 M NaOH. This pH adjusted solution (0.5 ml) is added to 1.0 ml of 100 mM sodium carbonate, pH 10.0, followed immediately by the addition of 0.5 ml of 4 mg/ml of MBI 11CN. The reaction mixture is incubated at ambient temperature for 22 hours. The progress of the reaction is monitored by analysis at various time points using RP-HPLC (FIG. 28). In FIG. 28, peak 2 is unreacted peptide, peak 3 is APS-modified peptide. Type 1 is the left-most of peak 3 and Type 2 is the right-most of peak 3.

Table 20 summarizes data from several experiments. Unless otherwise noted in table 20, the APS-modified peptides are prepared via the lyophilization method in 200 mM acetic acid-NaOH buffer, pH 4.6.

TABLE 20

| | | COMPLEX | |
|---|---|---|---|
| SEQUENCE | NAME | TYPE 1 | TYPE 2 |
| ILKKWPWWPWRRKamide (SEQ ID NO: 30) | 11CN | | |
| Solid phase, pH 2.0 | | Yes | Low |
| Solid phase, pH 4.6 | | Yes | Yes |
| Solid phase, pH 5.0 | | Yes | Yes |
| Solid phase, pH 6.0 | | Yes | Yes |
| Solid phase, pH 8.3 | | Yes | Yes |
| Solution, pH 2.0 | | Trace | Trace |
| Solution, pH 10.0 | | Yes | Yes-Slow |
| (Ac)$_4$-ILKKWPWWPWRRKamide (SEQ ID NO: 30) | 11CN-Y1 | No | No |
| ILRRWPWWPWRRKamide (SEQ ID NO: 38) | 11B1CN | Yes | Lowered |
| ILRWPWWPWRRKamide (SEQ ID NO: 42) | 11B7CN | Yes | Lowered |
| ILWPWWPWRRKamide (SEQ ID NO: 44) | 11B8CN | Yes | Lowered |
| ILRRWPWWPWRRRamide (SEQ ID NO: 25) | 11B9CN | Yes | Trace |
| ILKKWPWWPWKKKamide (SEQ ID NO: 45) | 11B10CN | Yes | Yes |
| ILKKWPWWPWRRkamide (SEQ ID NO: 64) | 11E3CN | Yes | Yes |
| ILKKWVWWPWRRKamide (SEQ ID NO: 67) | 11F3CN | Yes | Yes |
| ILKKWPWWPWKamide (SEQ ID NO: 28) | 11G13CN | Yes | Yes |
| ILKKWPWWPWRamide (SEQ ID NO: 75) | 11G14CN | Yes | Trace |

The modification of amino groups is further analyzed by determining the number of primary amino groups lost during attachment. The unmodified and modified peptides are treated with 2,4,6-trinitrobenzenesulfonic acid (TNBS) (R. L. Lundblad in *Techniques in Protein Modification and Analysis* pp. 151-154, 1995) (Table 21).

Briefly, a stock solution of MBI 11CN at 4 mg/ml and an equimolar solution of APS-modified MBI 11CN are prepared. A 0.225 ml aliquot of MBI 11CN or APS-modified MBI 11CN is mixed with 0.225 ml of 200 mM sodium phosphate buffer, pH 8.8. A 0.450 ml aliquot of 1% TNBS is added to each sample, and the reaction is incubated at 37° C. for 30 minutes. The absorbance at 367 nm is measured, and the number of modified primary amino groups per molecule is calculated using an extinction coefficient of 10,500 $M^{-1}$ $cm^{-1}$ for the trinitrophenyl (TNP) derivatives.

The primary amino group content of the parent peptide is then compared to the corresponding APS-modified peptide. As shown below, the loss of a single primary amino group occurs during formation of modified peptide. Peptides possessing a 3,4 lysine pair consistently give results that are 1 residue lower than expected, which may reflect steric hindrance after titration of one member of the doublet.

TABLE 21

| PEPTIDE SEQUENCE | TNP/PEPTIDE | TNP/APS-modified peptide | CHANGE |
|---|---|---|---|
| ILKKWPWWPWRRKamide (SEQ ID NO: 30) | 2.71 | 1.64 | 1.07 |
| ILRRWPWWPWRRKamide (SEQ ID NO: 38) | 1.82 | 0.72 | 1.10 |
| IlKKWPWWPWRRKamide (SEQ ID NO: 30) | 2.69 | 1.61 | 1.08 |
| ILKKWVWWPWRRKamide (SEQ ID NO: 67) | 2.62 | 1.56 | 1.06 |

Stability of APS-modified Peptide Analogues

APS-modified peptides demonstrate a high degree of stability under conditions that promote the dissociation of ionic or hydrophobic complexes. APS-modified peptide in formulation D is prepared as 800 µg/ml solutions in water, 0.9% saline, 8M urea, 8M guanidine-HCl, 67% 1-propanol, 1M HCl and 1M NaOH and incubated for 1 hour at room temperature. Samples are analyzed for the presence of free peptide using reversed phase HPLC and the following chromatographic conditions:

Solvent A: 0.1% trifluoroacetic acid (TFA) in water
Solvent B: 0.1% TFA/95% acetonitrile in water
Media: POROS R2-20 (polystyrene divinylbenzene)
Elution: 0% B for 5 column volumes
    0-25% B in 3 column volumes
    25% B for 10 column volumes
    25-95% B in 3 column volumes
    95% B for 10 column volumes Under these conditions, free peptide elutes exclusively during the 25% B step and formulation-peptide complex during the 95% B step. None of the dissociating conditions mentioned above, with the exception of 1M NaOH in which some degradation is observed, are successful in liberating free peptide from APS-modified peptide. Additional studies are carried out with incubation at 55° C. or 85° C. for one hour. APS-modified peptide is equally stable at 55° C. and is only slightly less stable at 85° C. Some acid hydrolysis, indicated by the presence of novel peaks in the HPLC chromatogram, is observed with the 1M HCl sample incubated at 85° C. for one hour.

Example 15

Purification of APS-Modified MBI 11CN

A large scale preparation of APS-modified MBI 11CN is purified. Approximately 400 mg of MBI 11CN is APS-modified and dissolved in 20 ml of water. Unreacted MBI 11CN is removed by RP-HPLC. The solvent is then evaporated from the APS-modified MBI 11CN pool, and the residue is dissolved in 10 ml methylene chloride. The modified peptide is then precipitated with 10 ml diethyl ether. After 5 min at ambient temperature, the precipitate is collected by centrifugation at 5000×g for 10 minutes. The pellet is washed with 5 ml of diethyl ether and again collected by centrifugation at 5000×g for 10 minutes. The supernatants are pooled for analysis of unreacted polysorbate by-products. The precipitate is dissolved in 6 ml of water and then flushed with nitrogen by bubbling for 30 minutes to remove residual ether. The total yield from the starting MBI 11CN was 43%.

Example 16

Biological Assays Using APS-Modified Peptide

All biological assays that compare APS-modified peptides with unmodified peptides are performed on an equimolar ratio. The concentration of APS-modified peptides can be determined by spectrophotometric measurement, which is used to normalize concentrations for biological assays. For example, a 1 mg/ml APS-modified MBI 11CN solution contains the same amount of peptide as a 1 mg/ml MBI 11CN solution, thus allowing direct comparison of toxicity and efficacy data.

APS-modified peptides are at least as potent as the parent peptides in in vitro assays performed as described herein. MIC values against gram positive bacteria are presented for several APS-modified peptides and compared with the values obtained using the parent peptides (Table 22). The results indicate that the modified peptides are at least as potent in vitro as the parent peptides and may be more potent than the parent peptides against *E. faecalis* strains.

TABLE 22

| | | | Corrected MIC (µg/ml) | |
|---|---|---|---|---|
| Organism | Organism # | Peptide | APS-peptide | Peptide |
| *A. calcoaceticus* | AC002 | MBI 11B1CN | 4 | 2 |
| *A. calcoaceticus* | AC002 | MBI 11B7CN | 8 | 4 |
| *A. calcoaceticus* | AC002 | MBI 11CN | >64 | 4 |
| *A. calcoaceticus* | AC002 | MBI 11E3CN | 8 | 2 |
| *A. calcoaceticus* | AC002 | MBI 11F3CN | 8 | 2 |
| *E. cloacae* | ECL007 | MBI 11B1CN | 128 | >128 |
| *E. cloacae* | ECL007 | MBI 11B7CN | 128 | 128 |
| *E. cloacae* | ECL007 | MBI 11CN | 64 | >128 |
| *E. cloacae* | ECL007 | MBI 11E3CN | 128 | >128 |
| *E. cloacae* | ECL007 | MBI 11F3CN | 128 | >128 |
| *E. coli* | ECO005 | MBI 11B1CN | 16 | 8 |
| *E. coli* | ECO005 | MBI 11B7CN | 64 | 8 |
| *E. coli* | ECO005 | MBI 11CN | 64 | 16 |
| *E. coli* | ECO005 | MBI 11E3CN | 64 | 8 |
| *E. coli* | ECO005 | MBI 11F3CN | 128 | 16 |
| *E. faecalis* | EFS001 | MBI 11B1CN | 4 | 32 |
| *E. faecalis* | EFS001 | MBI 11B7CN | 8 | 8 |
| *E. faecalis* | EFS001 | MBI 11CN | 8 | 32 |
| *E. faecalis* | EFS001 | MBI 11E3CN | 4 | 8 |
| *E. faecalis* | EFS001 | MBI 11F3CN | 8 | 32 |
| *E. faecalis* | EFS004 | MBI 11B1CN | 4 | 8 |
| *E. faecalis* | EFS004 | MBI 11B7CN | 8 | 8 |
| *E. faecalis* | EFS004 | MBI 11CN | 4 | 8 |
| *E. faecalis* | EFS004 | MBI 11E3CN | 4 | 2 |
| *E. faecalis* | EFS004 | MBI 11F3CN | 4 | 16 |

TABLE 22-continued

| Organism | Organism # | Peptide | Corrected MIC (µg/ml) APS-peptide | Peptide |
|---|---|---|---|---|
| E. faecalis | EFS008 | MBI 11B1CN | 8 | 32 |
| E. faecalis | EFS008 | MBI 11B7CN | 8 | 32 |
| E. faecalis | EFS008 | MBI 11CN | 64 | 64 |
| E. faecalis | EFS008 | MBI 11E3CN | 8 | 16 |
| E. faecalis | EFS008 | MBI 11F3CN | 4 | 128 |
| K. pneumoniae | KP001 | MBI 11B1CN | 32 | 128 |
| K. pneumoniae | KP001 | MBI 11B7CN | 64 | 16 |
| K. pneumoniae | KP001 | MBI 11CN | 64 | 128 |
| K. pneumoniae | KP001 | MBI 11E3CN | 64 | 8 |
| K. pneumoniae | KP001 | MBI 11F3CN | 128 | 64 |
| P. aeruginosa | PA004 | MBI 11B1CN | 128 | 128 |
| P. aeruginosa | PA004 | MBI 11B7CN | 128 | 128 |
| P. aeruginosa | PA004 | MBI 11CN | 64 | >128 |
| P. aeruginosa | PA004 | MBI 11E3CN | 128 | 128 |
| P. aeruginosa | PA004 | MBI 11F3CN | 128 | 128 |
| S. aureus | SA010 | MBI 11B1CN | 4 | 1 |
| S. aureus | SA010 | MBI 11B7CN | 4 | 1 |
| S. aureus | SA010 | MBI 11CN | 4 | 2 |
| S. aureus | SA010 | MBI 11E3CN | 2 | 1 |
| S. aureus | SA010 | MBI 11F3CN | 4 | 2 |
| S. aureus | SA011 | MBI 11B1CN | 16 | 4 |
| S. aureus | SA011 | MBI 11B7CN | 16 | 4 |
| S. aureus | SA011 | MBI 11CN | 16 | 8 |
| S. aureus | SA011 | MBI 11E3CN | 16 | 4 |

TABLE 22-continued

| Organism | Organism # | Peptide | Corrected MIC (µg/ml) APS-peptide | Peptide |
|---|---|---|---|---|
| S. aureus | SA011 | MBI 11F3CN | 16 | 8 |
| S. aureus | SA014 | MBI 11B1CN | 4 | 8 |
| S. aureus | SA014 | MBI 11B7CN | 8 | 4 |
| S. aureus | SA014 | MBI 11CN | 8 | 16 |
| S. aureus | SA014 | MBI 11E3CN | 4 | 4 |
| S. aureus | SA014 | MBI 11F3CN | 8 | 8 |
| S. aureus | SA018 | MBI 11B1CN | 32 | 16 |
| S. aureus | SA018 | MBI 11B7CN | 32 | 16 |
| S. aureus | SA018 | MBI 11CN | 64 | 64 |
| S. aureus | SA018 | MBI 11E3CN | 32 | 16 |
| S. aureus | SA018 | MBI 11F3CN | 64 | 16 |
| S. aureus | SA025 | MBI 11B1CN | 4 | 1 |
| S. aureus | SA025 | MBI 11B7CN | 2 | 1 |
| S. aureus | SA025 | MBI 11CN | 2 | 4 |
| S. aureus | SA025 | MBI 11E3CN | 2 | 1 |
| S. aureus | SA025 | MBI 11F3CN | 4 | 2 |
| S. aureus | SA093 | MBI 11B1CN | 2 | 1 |
| S. aureus | SA093 | MBI 11B7CN | 2 | 1 |
| S. aureus | SA093 | MBI 11CN | 2 | 2 |
| S. aureus | SA093 | MBI 11E3CN | 2 | 1 |
| S. aureus | SA093 | MBI 11F3CN | 2 | 1 |
| S. maltophilia | SMA002 | MBI 11B1CN | 64 | 128 |
| S. maltophilia | SMA002 | MBI 11B7CN | 128 | 32 |
| S. maltophilia | SMA002 | MBI 11CN | >64 | 128 |
| S. maltophilia | SMA002 | MBI 11E3CN | 128 | 64 |
| S. maltophilia | SMA002 | MBI 11F3CN | 128 | 64 |
| S. marcescens | SMS003 | MBI 11B1CN | 128 | >128 |
| S. marcescens | SMS003 | MBI 11B7CN | 128 | >128 |
| S. marcescens | SMS003 | MBI 11CN | 64 | >128 |
| S. marcescens | SMS003 | MBI 11E3CN | 128 | >128 |
| S. marcescens | SMS003 | MBI 11F3CN | 128 | >128 |

Toxicities of APS-modified MBI 11CN and unmodified MBI 11CN are examined in Swiss CD-1 mice. Groups of 6 mice are injected iv with single doses of 0.1 ml peptide in 0.9% saline. The dose levels used are 0, 3, 5, 8, 10, and 13 mg/kg. Mice are monitored at 1, 3, and 6 hrs post-injection for the first day, then twice daily for 4 days. The survival data for MBI 11CN mice are presented in Table 23. For APS-modified MBI 11CN, 100% of the mice survived at all doses, including the maximal dose of 13 mg/kg.

TABLE 23

| Peptide administered (mg/kg) | No. Dead/Total | Cumulative No. Dead | No. Surviving | Cumulative No. Dead/Total | % Dead |
|---|---|---|---|---|---|
| 13 | 6/6 | 18 | 0 | 18/18 | 100 |
| 10 | 6/6 | 12 | 0 | 12/12 | 100 |
| 8 | 6/6 | 6 | 0 | 6/6 | 100 |
| 5 | 0/6 | 0 | 6 | 0/6 | 0 |
| 3 | 0/6 | 0 | 12 | 0/12 | 0 |
| 0 | 0/6 | 0 | 18 | 0/18 | 0 |

As summarized below, the $LD_{50}$ for MBI 11CN is 7 mg/kg (Table 24), with all subjects dying at a dose of 8 mg/ml. The highest dose of MBI 11CN giving 100% survival was 5 mg/kg. The data show that APS-modified peptides are significantly less toxic than the parent peptides.

TABLE 24

| Test Peptide | $LD_{50}$ | $LD_{90-100}$ | MTD |
|---|---|---|---|
| MBI-11CN-TFA | 7 mg/kg | 8 mg/kg | 5 mg/kg |
| APS-MBI-11CN | >13 mg/kg* | >13 mg/kg* | >13 mg/kg* |

*could not be calculated with available data.

It will be appreciated that, although specific embodiments of the invention have been described herein for purposes of illustration, various modifications may be made without departing from the spirit and scope of the invention. Accordingly, the invention is not limited except as by the appended claims.

We claim:

1. An indolicidin analogue of up to 35 amino acids that comprises one of the following sequences:
  Ile Leu Lys Lys Trp Pro Trp Pro Trp Arg Arg Lys (SEQ ID NO: 33);
  Ile Leu Lys Lys Tyr Pro Trp Tyr Pro Trp Arg Arg Lys (SEQ ID NO: 34);
  Ile Leu Lys Trp Pro Trp Trp Pro Trp Arg Arg Lys (SEQ ID NO: 40);
  Ile Leu Trp Pro Trp Trp Pro Arg Arg Lys (SEQ ID NO: 44);
  Ile Leu Arg Trp Pro Trp Trp Pro Trp Arg Arg Lys Ile Met Ile Leu Lys Lys Ala Gly Ser (SEQ ID NO: 46);
  Ile Leu Arg Trp Pro Trp Trp Pro Trp Arg Arg Lys Met Ile Leu Lys Lys Ala Gly Ser (SEQ ID NO: 47);
  Ile Leu Arg Trp Pro Trp Trp Pro Trp Arg Arg Lys Asp Met Ile Leu Lys Lys Ala Gly Ser (SEQ ID NO: 48);
  Leu Lys Lys Trp Pro Trp Trp Pro Trp Arg Arg Lys (SEQ ID NO: 52);
  Ile Leu Lys Lys Trp Pro Trp Trp Pro Trp Arg Arg Met Ile Leu Lys Lys Ala Gly Ser (SEQ ID NO: 55);
  Ile Leu Lys Lys Trp Pro Trp Trp Pro Trp Arg Arg Ile Met Ile Leu Lys Lys Ala Gly Ser (SEQ ID NO: 56);
  Ile Leu Lys Lys Trp Pro Trp Trp Pro Trp Arg Arg Met (SEQ ID NO: 58);
  Ile Leu Lys Lys Trp Pro Trp Trp Pro Trp Arg Arg Ile Met (SEQ ID NO: 59);
  Ile Leu Lys Lys Trp Trp Trp Pro Trp Arg Lys (SEQ ID NO: 60);
  Ile Leu Lys Lys Trp Pro Trp Trp Trp Arg Lys (SEQ ID NO: 61);
  Ile Leu Lys Lys Trp Val Trp Trp Val Trp Arg Arg Lys (SEQ ID NO: 65);
  Ile Leu Lys Lys Trp Pro Trp Trp Val Trp Arg Arg Lys (SEQ ID NO:66);
  Ile Leu Lys Lys Trp Val Trp Trp Pro Trp Arg Arg Lys (SEQ ID NO: 67);
  Ile Lys Lys Trp Pro Trp Trp Pro Trp Arg Arg Lys (SEQ ID NO: 69);
  Ile Leu Lys Lys Pro Trp Trp Pro Trp Arg Arg Lys (SEQ ID NO: 70);
  Ile Leu Lys Lys Trp Trp Trp Pro Trp Arg Arg Lys (SEQ ID NO: 71);
  Ile Leu Lys Lys Trp Pro Trp Trp Trp Arg Arg Lys (SEQ ID NO: 72);
  Ile Leu Lys Lys Trp Pro Trp Trp Pro Arg Arg Lys (SEQ ID NO: 73);
  Ala Leu Arg Trp Pro Trp Trp Pro Trp Arg Arg Lys (SEQ ID NO: 76);
  Ile Ala Arg Trp Pro Trp Trp Pro Trp Arg Arg Lys (SEQ ID NO: 77);
  Ile Leu Ala Trp Pro Trp Trp Pro Trp Arg Arg Lys (SEQ ID NO: 78);
  Ile Leu Arg Ala Pro Trp Trp Pro Trp Arg Arg Lys (SEQ ID NO: 79);
  Ile Leu Arg Trp Ala Trp Trp Pro Trp Arg Arg Lys (SEQ ID NO: 80);
  Ile Leu Arg Trp Pro Ala Trp Pro Trp Arg Arg Lys (SEQ ID NO: 81); or
  Ile Leu Arg Trp Pro Trp Ala Pro Trp Arg Arg Lys (SEQ ID NO: 82).

2. The indolicidin analogue according to claim 1 wherein the analogue has at least one amino acid altered to a corresponding D-amino acid.

3. The indolicidin analogue according to claim 2 wherein the N-terminal and/or C-terminal amino acid is a D-amino acid.

4. The indolicidin analogue according to claim 1 wherein the analogue is acetylated at the N-terminal amino acid.

5. The indolicidin analogue according to claim 1 wherein the analogue is amidated at the C-terminal amino acid.

6. The indolicidin analogue according to claim 1 wherein the analogue is esterified at the C-terminal amino acid.

7. The indolicidin analogue according to claim 1 wherein the analogue is modified by incorporation of homoserine/homoserine lactone at the C-terminal amino acid.

8. An indolicidin analogue the amino acid sequence of which consists of Ile Leu Arg Trp Pro Trp Trp Pro Trp Arg Arg Lys (SEQ ID NO: 42).

9. The indolicidin analogue of claim 8, wherein the analogue has at least one amino acid altered to a corresponding D-amino acid.

10. The indolicidin analogue of claim 9, wherein the N-terminal and/or C-terminal amino acid is a D-amino acid.

11. A pharmaceutical composition comprising a physiologically acceptable buffer and an indolicidin analogue the amino acid sequence of which consists of Ile Leu Arg Trp Pro Trp Trp Pro Trp Arg Arg Lys (SEQ ID NO: 42).

12. A pharmaceutical composition comprising a physiologically acceptable buffer and at least one indolicidin analogue of up to 35 amino acids that comprises one of the following sequences:
  Ile Leu Lys Lys Trp Pro Trp Pro Trp Arg Arg Lys (SEQ ID NO: 33);
  Ile Leu Lys Lys Tyr Pro Trp Tyr Pro Trp Arg Arg Lys (SEQ ID NO: 34);
  Ile Leu Lys Trp Pro Trp Trp Pro Trp Arg Arg Lys (SEQ ID NO: 40);
  Ile Leu Trp Pro Trp Trp Pro Arg Arg Lys (SEQ ID NO: 44);
  Ile Leu Arg Trp Pro Trp Trp Pro Trp Arg Arg Lys Ile Met Ile Leu Lys Lys Ala Gly Ser (SEQ ID NO: 46);
  Ile Leu Arg Trp Pro Trp Trp Pro Trp Arg Arg Lys Met Ile Leu Lys Lys Ala Gly Ser (SEQ ID NO: 47);
  Ile Leu Arg Trp Pro Trp Trp Pro Trp Arg Arg Lys Asp Met Ile Leu Lys Lys Ala Gly Ser (SEQ ID NO: 48);
  Leu Lys Lys Trp Pro Trp Trp Pro Trp Arg Arg Lys (SEQ ID NO: 52);
  Ile Leu Lys Lys Trp Pro Trp Trp Pro Trp Arg Arg Met Ile Leu Lys Lys Ala Gly Ser (SEQ ID NO: 55);

Ile Leu Lys Lys Trp Pro Trp Trp Pro Trp Arg Arg Ile Met Ile Leu Lys Lys Ala Gly Ser (SEQ ID NO: 56);

Ile Leu Lys Lys Trp Pro Trp Trp Pro Trp Arg Arg Met (SEQ ID NO: 58);

Ile Leu Lys Lys Trp Pro Trp Trp Pro Trp Arg Arg Ile Met (SEQ ID NO: 59);

Ile Leu Lys Lys Trp Trp Trp Pro Trp Arg Lys (SEQ ID NO: 60);

Ile Leu Lys Lys Trp Pro Trp Trp Trp Arg Lys (SEQ ID NO: 61);

Ile Leu Lys Lys Trp Val Trp Trp Val Trp Arg Arg Lys (SEQ ID NO: 65);

Ile Leu Lys Lys Trp Pro Trp Trp Val Trp Arg Arg Lys (SEQ ID NO: 66);

Ile Leu Lys Lys Trp Val Trp Trp Pro Trp Arg Arg Lys (SEQ ID NO: 67);

Ile Lys Lys Trp Pro Trp Trp Pro Trp Arg Arg Lys (SEQ ID NO: 69);

Ile Leu Lys Lys Pro Trp Trp Pro Trp Arg Arg Lys (SEQ ID NO: 70);

Ile Leu Lys Lys Trp Trp Trp Pro Trp Arg Arg Lys (SEQ ID NO: 71);

Ile Leu Lys Lys Trp Pro Trp Trp Trp Arg Arg Lys (SEQ ID NO: 72);

Ile Leu Lys Lys Trp Pro Trp Trp Pro Arg Arg Lys (SEQ ID NO: 73);

Ala Leu Arg Trp Pro Trp Trp Pro Trp Arg Arg Lys (SEQ ID NO: 76);

Ile Ala Arg Trp Pro Trp Trp Pro Trp Arg Arg Lys (SEQ ID NO: 77);

Ile Leu Ala Trp Pro Trp Trp Pro Trp Arg Arg Lys (SEQ ID NO: 78);

Ile Leu Arg Ala Pro Trp Trp Pro Trp Arg Arg Lys (SEQ ID NO: 79);

Ile Leu Arg Trp Ala Trp Trp Pro Trp Arg Arg Lys (SEQ ID NO: 80);

Ile Leu Arg Trp Pro Ala Trp Pro Trp Arg Arg Lys (SEQ ID NO: 81); or

Ile Leu Arg Trp Pro Trp Ala Pro Trp Arg Arg Lys (SEQ ID NO: 82).

13. The pharmaceutical composition according to claim 12, wherein said at least one analogue has one or more amino acids altered to a corresponding D-amino acid.

14. The pharmaceutical composition according to claim 13, wherein the N-terminal and/or C-terminal amino acid of said at least one analogue is a D-amino acid.

15. The pharmaceutical composition according to claim 12, wherein said at least one analogue is acetylated at the N-terminal amino acid.

16. The pharmaceutical composition according to claim 12, wherein said at least one analogue is amidated at the C-terminal amino acid.

17. The pharmaceutical composition according to claim 12, wherein said at least one analogue is esterified at the C-terminal amino acid.

18. The pharmaceutical composition according to claim 12, wherein said at least one analogue is modified by incorporation of homoserine/homoserine lactone at the C-terminal amino acid.

19. The pharmaceutical composition according to claim 12, wherein the composition is incorporated in a liposome or a slow-release vehicle.

20. A method of treating a microbial infection, comprising administering to a patient a therapeutically effective amount of a pharmaceutical composition according to any one of claims 12-19.

21. The method of claim 20, wherein the infection is due to a microorganism selected from the group consisting of a bacterium, a fungus, and a protozoa.

22. The method of claim 20, wherein the microorganism is a bacterium, wherein the bacterium is a Gram-negative or a Gram-positive bacterium.

23. The method of claim 20, wherein the pharmaceutical composition is administered by intravenous injection, intraperitoneal injection or implantation, intramuscular injection or implantation, intrathecal injection, subcutaneous injection or implantation, intradermal injection, lavage, bladder wash-out, suppositories, pessaries, oral ingestion, topical application, enteric application, inhalation, or nasal route.

24. The method of claim 20, wherein the pharmaceutical composition is administered by local application.

25. The method of claim 20, wherein the method is for treating a microbial infection associated with a medical device.

26. The method according to claim 20, wherein the pharmaceutical composition further comprises an antibiotic.

27. A method of treating a microbial infection, comprising administering to a patient a therapeutically effective amount of a pharmaceutical composition comprising an indolicidin analogue of up to 35 amino acids comprising the sequence of Ile Leu Arg Trp Pro Trp Trp Pro Trp Arg Arg Lys (SEQ ID NO: 42).

28. The method of claim 27, wherein the amino acid sequence consists of Ile Leu Arg Trp Pro Trp Trp Pro Trp Arg Arg Lys (SEQ ID NO: 42).

29. The method of claim 27 or claim 28, wherein the pharmaceutical composition further comprises a physiologically acceptable buffer.

30. The method of claim 27 or claim 28, wherein the pharmaceutical composition is administered by intravenous injection, intraperitoneal injection or implantation, intramuscular injection or implantation, intrathecal injection, subcutaneous injection or implantation, intradermal injection, lavage, bladder wash-out, suppositories, pessaries, oral ingestion, topical application, enteric application, inhalation, or nasal route.

31. The method of claim 27 or claim 28, wherein the pharmaceutical composition is administered by local application.

32. The method of claim 27 or claim 28, wherein the method is for treating a microbial infection associated with a medical device.

33. The method of claim 27 or claim 28, wherein the pharmaceutical composition further comprises an antibiotic.

34. The method of claim 33, wherein said antibiotic is minocycline.

35. The method of claim 33, wherein said antibiotic is rifampin.

36. The method of claim 33, wherein said antibiotic is cefazolin.

37. The method of claim 33, wherein said antibiotic is vancomycin.

38. The method of claim 33, wherein said antibiotic is teicoplanin.

39. The method of claim 33, wherein said antibiotic is a beta lactam.

40. The method of claim 27 or claim 28, wherein the infection is due to a microorganism selected from the group consisting of a bacterium, a fungus, and a protozoa.

41. The method of claim 40, wherein the microorganism is a Gram-negative or a Gram-positive bacterium.

42. The method of claim 40, wherein the fungus is a pathogenic yeast.

43. The method of claim 40, wherein the fungus is a mold that causes wound infections.

44. The method of claim 41, wherein said Gram-negative bacterium is selected from the group consisting of *Enterobacter sp.*, *E. coli* and *Acinetobacter* sp.

45. The method of claim 41, wherein said Gram-positive bacterium is selected from the group consisting of *S. aureus*, coagulase negative staphylococci, *S. epidermidis*, *S. pneumoniae*, and Viridans Streptococci.

* * * * *